United States Patent
Hess et al.

(10) Patent No.: US 10,801,540 B2
(45) Date of Patent: Oct. 13, 2020

(54) LOCKING MECHANISMS WITH DEFLECTABLE LOCK MEMBER

(71) Applicant: Enduralock, LLC, Lenexa, KS (US)

(72) Inventors: Harold Hess, Leawood, KS (US); Tracy Hockenhull, Lenexa, KS (US); Warren Moore, Lenexa, KS (US); Armando Perez, III, Los Angeles, CA (US); Zoltan Kalman Furu-Szekely, Cypress, TX (US); Igor Komsitsky, Los Angeles, CA (US); Deeptesh Selvaraj, Overland Park, KS (US)

(73) Assignee: Enduralock, LLC, Lenexa, KS (US)

( * ) Notice: Subject to any disclaimer, the term of this patent is extended or adjusted under 35 U.S.C. 154(b) by 0 days.

(21) Appl. No.: 16/160,068

(22) Filed: Oct. 15, 2018

(65) Prior Publication Data
US 2019/0048919 A1     Feb. 14, 2019

Related U.S. Application Data

(63) Continuation-in-part of application No. 15/258,847, filed on Sep. 7, 2016, now Pat. No. 10,125,807, and
(Continued)

(51) Int. Cl.
*F16B 39/282* (2006.01)
*A61B 17/70* (2006.01)
(Continued)

(52) U.S. Cl.
CPC ........ *F16B 39/282* (2013.01); *A61B 17/7032* (2013.01); *F16B 39/108* (2013.01); *F16B 39/24* (2013.01); *F16B 39/28* (2013.01)

(58) Field of Classification Search
CPC ........ F16B 39/10; F16B 39/108; F16B 39/12; F16B 39/24; F16B 39/26; F16B 39/28; F16B 39/282; A61B 17/7032
(Continued)

(56) References Cited

U.S. PATENT DOCUMENTS

| 307,671 A | 11/1884 | McTighe |
| 545,516 A | 9/1895 | Mershon |

(Continued)

FOREIGN PATENT DOCUMENTS

| CN | 105003518 A | 10/2015 |
| JP | S48-44540 Y | 12/1973 |

(Continued)

OTHER PUBLICATIONS

TineLok: Overview, www.tinelok.com (2013).
(Continued)

*Primary Examiner* — Roberta S Delisle
(74) *Attorney, Agent, or Firm* — Armstrong Teasdale LLP

(57) ABSTRACT

A fastener assembly includes a lock nut configured to threadably engage a threaded body portion, and a first lock member including a plurality of radially extending ratchet teeth. The fastener assembly also includes a second lock member including a base portion and at least one tab extending axially from the base portion. The base portion defines an aperture sized to receive the threaded body portion. The at least one tab has a proximal end joined to the base portion and a free end opposite the proximal end. The second lock member is positionable between a locked configuration in which the free end of the at least one tab is configured to engage the plurality of radially extending ratchet teeth and an unlocked configuration in which the free end of the at least one tab is spaced from the plurality of radially extending ratchet teeth. The base portion and the at least one tab are a single piece.

19 Claims, 76 Drawing Sheets

Related U.S. Application Data a continuation-in-part of application No. 15/447,570, filed on Mar. 2, 2017, now Pat. No. 10,215,217, which is a continuation-in-part of application No. 15/099,763, filed on Apr. 15, 2016, now Pat. No. 9,841,046.

(60) Provisional application No. 62/215,631, filed on Sep. 8, 2015, provisional application No. 62/220,867, filed on Sep. 18, 2015, provisional application No. 62/148,846, filed on Apr. 17, 2015, provisional application No. 62/193,437, filed on Jul. 16, 2015.

(51) Int. Cl.
*F16B 39/24* (2006.01)
*F16B 39/10* (2006.01)
*F16B 39/28* (2006.01)

(58) Field of Classification Search
USPC .......................................... 411/204, 205, 221
See application file for complete search history.

(56) References Cited

U.S. PATENT DOCUMENTS

| | | | |
|---|---|---|---|
| 599,690 A * | 3/1898 | Deadman | F16B 39/24 411/138 |
| 646,337 A | 3/1900 | Wilson et al. | |
| 687,774 A * | 12/1901 | Oliver | F16B 39/32 411/326 |
| 689,173 A * | 12/1901 | Everett et al. | F16B 39/10 411/128 |
| 771,733 A * | 10/1904 | Johnson | F16B 39/12 411/245 |
| 779,632 A | 1/1905 | Wolf | |
| 826,591 A | 7/1906 | Mohr | |
| 848,176 A | 3/1907 | Jordan | |
| 892,507 A | 7/1908 | Dorsey | |
| 898,003 A | 9/1908 | Posson | |
| 907,473 A | 12/1908 | Tray | |
| 955,054 A | 4/1910 | Darby et al. | |
| 961,371 A | 6/1910 | Posey | |
| 964,813 A * | 7/1910 | Roedler | F16B 39/24 411/118 |
| 1,011,871 A | 12/1911 | Smoke | |
| 1,057,209 A | 3/1913 | Andrews | |
| 1,075,925 A | 10/1913 | Maxwell | |
| 1,140,974 A | 5/1915 | Formby | |
| 1,225,626 A | 5/1917 | Hannon et al. | |
| 1,246,353 A | 11/1917 | Thigpen | |
| 1,249,336 A | 12/1917 | Cook | |
| 1,276,882 A | 8/1918 | Davis | |
| 1,287,371 A | 12/1918 | McClay et al. | |
| 1,289,710 A | 12/1918 | Ervin | |
| 1,323,188 A * | 11/1919 | Humphris | F16B 39/24 411/164 |
| 1,337,424 A | 4/1920 | Word | |
| 1,371,742 A * | 3/1921 | Dringman | F16B 39/24 411/133 |
| 1,403,902 A | 1/1922 | Fields | |
| 1,418,050 A * | 5/1922 | Bable | F16B 39/282 411/204 |
| 1,509,948 A | 9/1924 | Hall | |
| 1,526,914 A | 2/1925 | Kibler | |
| 2,018,574 A | 10/1935 | Richter | |
| 2,131,812 A | 10/1938 | Maguire | |
| 2,141,701 A | 12/1938 | Uherkovich | |
| 2,398,965 A | 4/1946 | Rounds | |
| 3,275,055 A * | 9/1966 | Gutshall | F16B 39/282 411/134 |
| 3,294,140 A | 12/1966 | Cosenza | |
| 3,712,355 A | 1/1973 | Schenk | |
| 5,190,423 A | 3/1993 | Ewing | |
| 5,224,806 A | 7/1993 | Duran | |
| 5,460,468 A | 10/1995 | DiStacio | |
| 5,533,852 A | 7/1996 | Matthews | |
| 5,538,378 A | 7/1996 | Van Der Drift | |
| 5,575,602 A | 11/1996 | Savage et al. | |
| 5,597,278 A | 1/1997 | Peterkort | |
| 5,618,143 A | 4/1997 | Cronin, II | |
| 5,702,214 A | 12/1997 | Duran | |
| 5,713,708 A | 2/1998 | Van Der Drift et al. | |
| 5,735,853 A | 4/1998 | Olerud | |
| 5,772,373 A * | 6/1998 | Cronin, II | B25B 13/48 411/120 |
| 5,951,224 A | 9/1999 | DiStasio | |
| 6,010,289 A | 1/2000 | DiStasio et al. | |
| 6,082,941 A | 7/2000 | Dupont et al. | |
| 6,139,550 A | 10/2000 | Michelson | |
| 6,258,089 B1 | 7/2001 | Campbell et al. | |
| 6,261,291 B1 | 7/2001 | Talaber et al. | |
| 6,361,257 B1 | 3/2002 | Grant | |
| 6,383,186 B1 | 5/2002 | Michelson | |
| 6,398,783 B1 | 6/2002 | Michelson | |
| 6,413,259 B1 | 7/2002 | Lyons et al. | |
| 6,434,792 B1 | 8/2002 | Williamson | |
| 6,602,255 B1 | 8/2003 | Campbell et al. | |
| 6,626,907 B2 | 9/2003 | Campbell et al. | |
| 6,695,846 B2 | 2/2004 | Richelsoph et al. | |
| 6,755,833 B1 | 6/2004 | Paul et al. | |
| 6,935,822 B2 | 8/2005 | Hartmann et al. | |
| 6,976,816 B2 | 12/2005 | Slesinski et al. | |
| 6,976,817 B1 | 12/2005 | Grainger | |
| 7,128,511 B2 | 10/2006 | Hewgill | |
| 7,189,044 B2 | 3/2007 | Ball | |
| 7,270,509 B2 | 9/2007 | Disantis et al. | |
| 7,318,825 B2 | 1/2008 | Butler et al. | |
| 7,374,495 B2 | 5/2008 | Ball | |
| 7,621,943 B2 | 11/2009 | Michelson | |
| 7,763,056 B2 | 7/2010 | Dalton | |
| 7,857,839 B2 | 12/2010 | Duong et al. | |
| 7,887,547 B2 | 2/2011 | Campbell et al. | |
| 7,909,859 B2 | 3/2011 | Mosca et al. | |
| 7,955,037 B2 | 6/2011 | Disantis et al. | |
| 8,123,788 B2 | 2/2012 | Michelson | |
| 8,262,711 B2 | 9/2012 | Hess | |
| 8,366,365 B2 | 2/2013 | Disantis et al. | |
| 8,727,684 B1 | 5/2014 | Woods | |
| 8,784,027 B2 | 7/2014 | Hess | |
| 2005/0207865 A1 | 9/2005 | Disantis et al. | |
| 2005/0209599 A1 | 9/2005 | Brunsvold | |
| 2006/0015104 A1 | 1/2006 | Dalton | |
| 2009/0060682 A1 | 3/2009 | Yeh et al. | |
| 2009/0192553 A1 | 7/2009 | Maguire et al. | |
| 2010/0121383 A1 | 5/2010 | Stanaford et al. | |
| 2011/0188970 A1 | 8/2011 | Dillon et al. | |
| 2012/0063864 A1 | 3/2012 | Hess | |
| 2014/0190315 A1 | 7/2014 | Kiser | |
| 2014/0356097 A1 | 12/2014 | Hess | |
| 2016/0084291 A1 | 3/2016 | Stewart | |
| 2016/0305465 A1 | 10/2016 | Hess et al. | |

FOREIGN PATENT DOCUMENTS

| | | |
|---|---|---|
| JP | S51-19172 U | 2/1976 |
| JP | S52-151269 U | 11/1977 |
| JP | H07217634 A | 8/1995 |
| JP | H084743 A | 1/1996 |
| JP | 2000-310213 A | 11/2000 |
| KR | 200241791 | 10/2001 |
| KR | 100863200 B1 | 10/2008 |
| KR | 2011-0099247 A | 9/2011 |

OTHER PUBLICATIONS

TineLok, The Revolutionary Vibration-Proof Fastener System, www.tinelok.com (2013).

International Search Report and Written opinion for PCT/US 16/50534, dated Feb. 6, 2017, 11 pages.

(56) References Cited

OTHER PUBLICATIONS

English translation of Office Action dated Apr. 28, 2020 in corresponding Japanese Application No. 2017-546147.

* cited by examiner

LOCKING MECHANISMS WITH DEFLECTABLE LOCK MEMBER

CROSS REFERENCE TO RELATED APPLICATIONS

This application is a continuation-in-part application of U.S. patent application Ser. No. 15/258,847 filed Sep. 7, 2016, and U.S. patent application Ser. No. 15/447,570 filed Mar. 2, 2017. The '847 application claims priority to U.S. Provisional Patent Application Ser. No. 62/215,631, filed Sep. 8, 2015, and U.S. Provisional Patent Application Ser. No. 62/220,867, filed Sep. 18, 2015. The '570 application is a continuation-in-part application of U.S. patent application Ser. No. 15/099,763 filed Apr. 15, 2016, and claims priority to U.S. Provisional Patent Application Ser. No. 62/148,846 filed Apr. 17, 2015, and U.S. Provisional Patent Application Ser. No. 62/193,437 filed Jul. 16, 2015. Each of the preceding patent applications is incorporated herein by reference in its entirety.

BACKGROUND

The field of the disclosure relates generally to fasteners, and more specifically to locking mechanisms for threaded fasteners.

Fasteners commonly include mechanisms or design features for ensuring that fastener elements do not loosen over time, potentially allowing joined elements to loosen or separate. Examples of mechanisms include thread bore inserts and screw thread profiles that deform when tightened. Fasteners accessories like lock washers, cotter pins, and lock wires are also commonly used with fasteners to prevent fastener elements from loosening. Adhesive materials, like epoxy, can be applied to fastener threads to stake fastener elements to prevent fastener elements from loosening. However, conventional fastener mechanisms, accessories, and adhesive materials may not be suitable for some applications, such as high temperature environments or with structures subject to extreme vibration.

Moreover, the time and cost required to manufacture fastener assemblies could be reduced. For example, at least some fastener mechanisms or accessories for ensuring that fastener elements do not loosen over time require custom or specialized manufacturing processes such as an injection molding process with custom molds for each fastener mechanism. Such processes can increase the time and cost required to manufacture fastener assemblies.

Accordingly, there is a need for an improved fastener assembly that can be produced using manufacturing processes that are less expensive and quicker than manufacturing processes for conventional fasteners.

BRIEF DESCRIPTION

In one aspect, a fastener assembly is provided. The fastener assembly includes a threaded member including a threaded body portion, a lock nut configured to threadably engage the threaded body portion, and a first lock member including a plurality of radially extending ratchet teeth. The fastener assembly also includes a second lock member including a base portion and at least one tab extending axially from the base portion. The base portion defines an aperture extending therethrough. The aperture is sized to receive the threaded body portion. The at least one tab has a proximal end joined to the base portion and a free end opposite the proximal end. The second lock member is positionable between a locked configuration in which the free end of the at least one tab is configured to engage the plurality of radially extending ratchet teeth and an unlocked configuration in which the free end of the at least one tab is spaced from the plurality of radially extending ratchet teeth. The base portion and the at least one tab are a single piece.

In another aspect, a method of assembling a locking mechanism for a fastener includes a threaded body portion. The method includes providing a first lock member including a plurality of radially extending ratchet teeth. The first lock member defines a first aperture extending therethrough. The first aperture is sized to receive the threaded body portion. The method also includes forming a base portion of a second lock member. The base portion defines a second aperture extending therethrough. The second aperture is sized to receive the threaded body portion. The method further includes forming at least one tab of the second lock member. The at least one tab has a proximal end joined to the base portion and a free end opposite the proximal end. The method also includes bending the at least one tab at an angle relative to the base portion such that the at least one tab extends axially from the base portion. The second lock member is positionable between a locked configuration in which the free end of the at least one tab is configured to engage the plurality of radially extending ratchet teeth and an unlocked configuration in which the free end of the at least one tab is spaced from the plurality of radially extending ratchet teeth. The base portion and the at least one tab are a single piece.

In yet another aspect, a locking mechanism for a fastener is provided. The locking mechanism includes a lock nut having a peripheral surface defining an axially-extending slot. The lock member is releasably coupled to the lock nut for rotation therewith. The lock member includes at least one axially-extending tab and a radially-extending detent member on the at least one axially-extending tab. The at least one axially-extending tab at least partially engages the axially-extending slot. The locking mechanism further includes a lock washer including an axially-extending wall about a periphery of the lock washer. The axially-extending wall defines an inner cavity for receiving the radially-extending detent member of the lock member. The axially-extending wall includes an inner surface defining a plurality of radially-extending notches configured to receive the radially-extending detent member.

In still another aspect, a fastener assembly is provided. The fastener assembly includes a threaded member comprising a threaded body portion. The fastener assembly also includes a lock nut configured to threadably engage the threaded body portion. The lock nut includes a body having an outer surface with a plurality of radially extending ratchet teeth. The fastener assembly further includes a lock washer including a base portion and at least one tab extending axially from the base portion. The base portion includes an aperture extending therethrough. The base portion includes at least one anti-rotation structure configured to rotationally fix the lock washer with respect to the threaded member. The at least one tab includes an end having a plurality of teeth. The plurality of teeth extend toward the base portion and are configured to engage the plurality of radially extending teeth of the lock nut.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Figure 1:
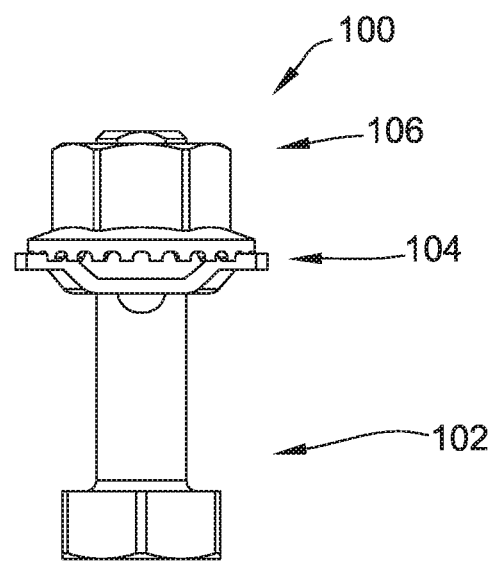
FIG. 1 is a side view of an exemplary embodiment of a fastener assembly.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms such as "about," "approximately," and "substantially" are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Relative descriptions herein such as upward, downward, left, right, up, down, length, height, width, thickness and the like are with reference to the Figures, and not meant in a limiting sense. Additionally, the illustrated embodiments can be understood as providing exemplary features of varying detail of certain embodiments, and therefore, features, components, modules, elements, and/or aspects of the illustrations can be otherwise combined, interconnected, sequenced, separated, interchanged, positioned, and/or rearranged without materially departing from the disclosed fastener assemblies. Additionally, the shapes and sizes of components are also exemplary and can be altered without materially affecting or limiting the disclosed technology.

It should be appreciated that the present technology can be implemented and utilized in numerous ways, including without limitation as a process, an apparatus, a system, a device, a method of installation and removal, a method for applications now known and later developed. These and other unique features of the technology disclosed herein will become more readily apparent from the following description and the accompanying drawings.

The fastening devices and systems described herein overcome many of the prior art problems associated with threaded fasteners. In general, threaded fasteners are used to fixedly connect two or more pieces in a variety of applications such as, without limitation, surgical implants, industrial applications, aerospace applications, and building applications. Among other features and benefits, the disclosed fastening devices and systems facilitate one or more of quick and easy installation and/or removal, reduced torque requirements, vibration resistant secured tightness, and/or single end access for blind fastening applications. The advantages, and other features of the technology disclosed herein, will become more readily apparent to those having ordinary skill in the art from the following detailed description of certain preferred embodiments taken in conjunction with the drawings.

Aspects of the present disclosure are directed to a fastener locking mechanism including an elongated bolt member having a threaded segment with a banking feature, a washer member having a circumferential wall with radially inward facing engagement teeth and a banking portion that complements the banking feature of the bolt member, a lock member having an annular body with an upstanding spring finger and a tooth disposed on a radially outward surface of the annular body, and a nut member having a circumferential flat with an axial slot and a threaded bore corresponding to threaded segment of the bolt member. The banking feature of the bolt member cooperates with the banking portion of the washer member to fix the washer member in rotation relative to the bolt member. The spring finger of the lock member cooperates with the axial slot of the nut member to fix the lock member in rotation relative to the nut member. The tooth of the lock member is displaceable radially relative to the bolt member for engaging and disengaging the engagement teeth of the washer member. In a radially outer position, the tooth of the lock member intermeshes with the engagement teeth of the washer member to fix the lock member and nut member in rotation relative to the washer member. In a radially inner position, the tooth of the lock member is rotatable relative to the washer member such that the lock member and nut member are rotatable relative to the washer member and the bolt member.

In accordance with certain embodiments, the bolt member can include a flat or two or more flats or other features designed to prevent rotation of the washer member in relation to the threaded member. The flat can extend axially along a length of bolt member. The banking feature of the bolt member can include the flat. The flat can be radially adjacent to the threaded segment of the bolt member. The flat can be a first flat, and the bolt member can include one or more second flats. The banking feature can include both the first flat and the second flat. The second flat can extend axially along the bolt member. The second flat can be disposed on a side of the bolt member diametrically opposite the first flat. The threaded segment can extend circumferentially about the bolt member and couple the first flat with the second flat.

It is also contemplated that, in accordance with certain embodiments, the washer member can have opposed axial surfaces separated by an axial thickness of the washer member. A circumferential wall can extend from a periphery axially from a surface of washer member. Engagement teeth can be disposed on a radially inner surface of the circumferential wall. The engagement teeth can extend radially inward from the circumferential wall. A central aperture can extend through the thickness of the washer member between the axial surfaces of the washer member. The central aperture can include the banking portion that complements the banking feature of the bolt member. For example, one or more flat segments can bound the central aperture. The flat segment can correspond with the banking feature of the bolt member. The central aperture can include one or more arcuate segments bounding the central aperture. The arcuate segment can correspond to the threaded segment(s) of the bolt member. The central aperture can include both flat and arcuate segments, and a stress reduction feature can be disposed at an intersection of a flat segment and an arcuate segment.

In certain embodiments, the lock member can include a spring finger having a free end and a fixed end. The free end can be disposed radially inward of the fixed end. The fixed end can be connected to the annular body of the lock member. The tooth and the spring finger can be circumferentially aligned with one another. The annular body of the lock member can have a round, oval, square, rectangular, or any suitably shaped axial profile. The annular body can be deformable, for example becoming more round (or more elliptical) in response to inward force exerted on the spring finger at a location between the fixed and free ends of the spring finger. The spring finger can be a first spring finger, and the lock member can include a second spring finger connected to the annular body on a side of the annular body opposite the first spring finger.

In accordance with certain embodiments, the lock member can have first and second teeth that each extend radially outward from the annular body of the lock member. The first and second teeth can be circumferentially adjacent to one another. The first and second teeth can also be circumferentially aligned to the spring tab. The first and second teeth can be disposed on opposite sides of the annular body of the lock member such that each extends radially in a direction opposite the other. The second tooth can be circumferentially aligned with a second spring finger of the lock member. It is also contemplated that more than one circumferentially adjacent tooth can be aligned to a first spring finger, and that more than one circumferentially adjacent tooth can be aligned to the second spring finger.

It is also contemplated that, in accordance with certain embodiments, the nut member can have an annular recess. The annular recess can have a diameter that is less than a diameter of the annular body of the lock member. The nut member can have a circumference with a plurality of faces. The plurality of faces of the nut member can form a hexagonal circumference extending about the nut member. One or more of the faces of the nut member can have an axial slot. The axial slot can extend between the annular recess and an end of the nut member opposite the annular recess of the nut member. It is contemplated that the nut member can have faces with axial slots disposed on faces that are diametrically opposed to one another.

In an aspect, the threaded segment and banking feature of the bolt member, central aperture and engagement teeth of the washer member, tooth and spring finger of the lock member, and axial slot of the nut member can cooperate as a locking mechanism. The locking mechanism can have a locked position wherein the annular body urges the lock member tooth radially outward such that the tooth intermeshes with the engagement teeth of the washer member, fixing the lock member in rotation relative to the washer member and preventing loosening of the nut member from the bolt member. The locking mechanism can have a tighten or release position wherein the annular body of the lock member urges the lock member tooth radially inward, rendering the lock member and nut member rotatable relative to the washer member and bolt member. It is contemplated that lock member can have a spring preload that normally urges the lock member tooth radially outward, and that a force exerted on the spring finger of the lock member can urge the lock member tooth radially inward to reconfigure the locking mechanism from the locked position to the tighten or release position.

In another aspect, a spinal fixation system includes a fastener locking mechanism as described above and a rod. The rod seats in the bolt member and below the washer member. It is contemplated that tightening the nut member exerts force on the washer member which in turn urges the rod against the bolt member.

In certain embodiments, the bolt member can have a head portion coupled to an end of a stem section. The head portion can be fixed relative to the stem portion. A joint can be interposed between the head portion and the stem portion, the head portion thereby being movable relative to the stem portion. The head portion can be pivotable relative to the stem portion, such as in a conical movement envelope. The head portion can have a first threaded segment and the stem portion can have a second threaded segment. The first threaded segment can be a male threaded segment corresponding to a female threaded segment defined by the bore of the nut member. The second threaded segment can taper between an end adjacent to the head member and an end of the stem portion opposite the head portion. It is contemplated that the second threaded segment can have threads adapted for seating the bolt member to a bone structure, such as a pedicle.

In accordance with certain embodiments, the bolt member can include a tulip head. The tulip head can have a slot extending therethrough for seating the rod. The slot can be centrally disposed, extending across the top of the bolt member. The slot can be laterally disposed, extending across a side of the bolt member. Lobes can be defined on opposite sides of the slot. The lobes can have the banking feature of the bolt member defined thereon. The lobes can have the threaded segment of the bolt member defined thereon. In a contemplated exemplary embodiment, each lobe has portions of both the threaded segment and the banking feature defined thereon.

It is also contemplated that, in accordance with certain embodiments, the washer member can include a central bar portion. The central bar portion can extend across the washer member central aperture and divide the central aperture into first and second portions. One lobe of the bolt member tulip head can extend through the first portion of the central aperture, and the another lobe of the bolt member tulip head can extend through the second portion of the central aperture. The central bar portion can extend from the banking portion of the washer member such that, when the central bar portion is seated with the slot of the tulip head, the washer member is fixed in rotation relative to the tulip head. It is contemplated that central bar portion can seat slot of the tulip head, overlay the rod, and can be disposed between the nut member, lock member, and the stem of the bolt member.

In embodiments described herein, a fastener mechanism includes an elongated bolt member and a lock nut. In addition, the locking mechanism includes a lock member that may be integrally formed with or coupled to the lock nut for rotation therewith. Moreover, the locking mechanism includes a lock washer that engages with the lock member to allow rotation of the lock nut relative to the bolt member in a first direction and prevent rotation of the lock nut in a second direction. At least one of the lock member and the lock washer includes at least one tab and is positionable between a locked configuration in which a free end of the at least one tab is configured to engage a plurality of radially extending ratchet teeth and an unlocked configuration in which the free end of the at least one tab is spaced from the plurality of radially extending ratchet teeth. The at least one tab is integrally formed with the lock member or the lock washer and allows the fastener mechanism to be at least partially formed using a stamping process. As a result, the time and cost required to assemble the fastener locking mechanism is reduced in comparison to the manufacturing processes for at least some known fasteners.

Figure 2:
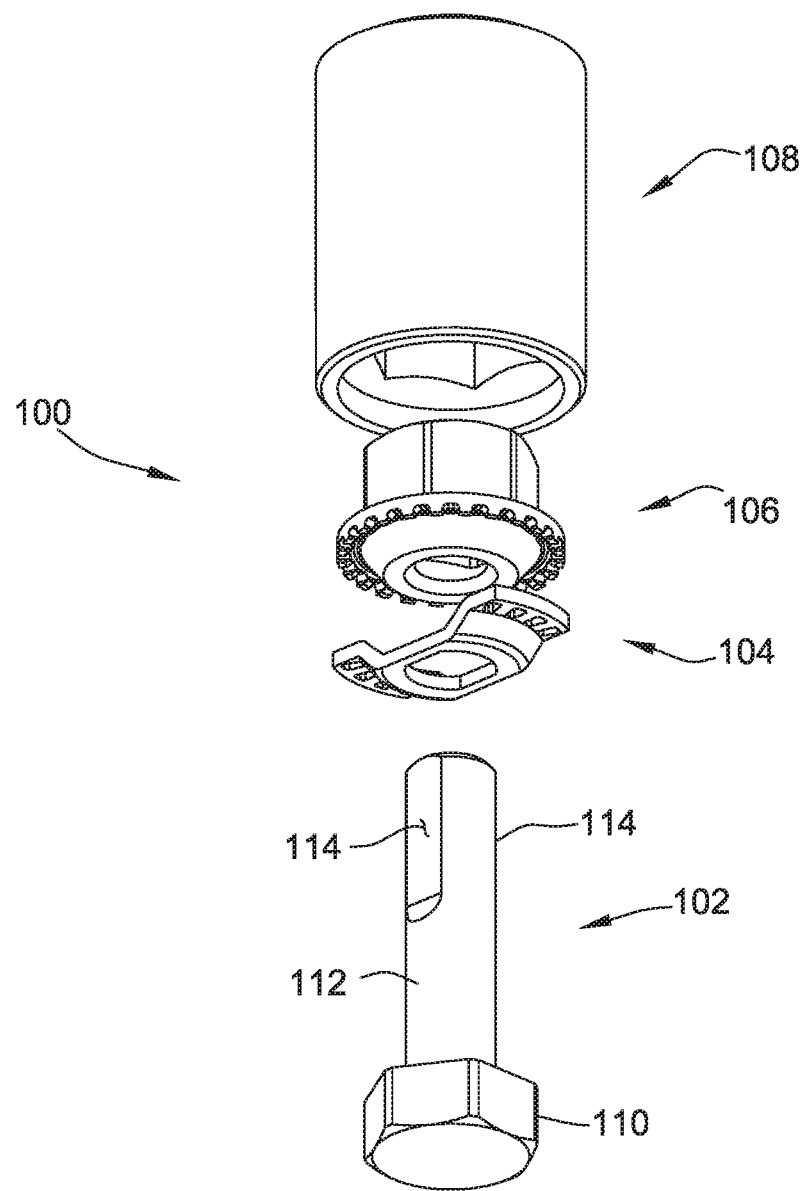
FIG. 2 is an exploded perspective view of the fastener assembly shown in FIG. 1, including a tool for use with the fastener assembly.
Figure 3:
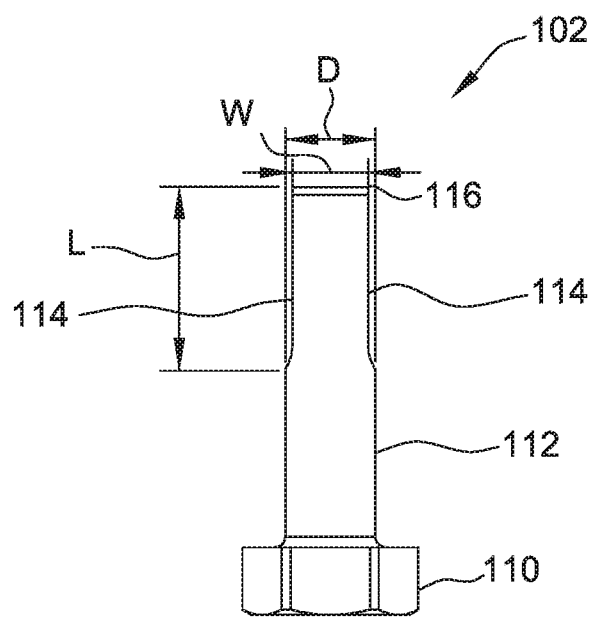
FIG. 3 is a side view of a threaded member of the fastener assembly of FIG. 1.

FIG. 1 is a side view of an exemplary embodiment of a fastener assembly 100. FIG. 2 is an exploded perspective view of fastener assembly 100, including a tool 108 for use with fastener assembly 100. FIG. 3 is a side view of a threaded member 102 of fastener assembly 100 (shown in FIG. 1). In the exemplary embodiment, fastener assembly 100 includes threaded member 102, a lock washer 104, a lock nut 106, and a tool 108. As described with reference to FIGS. 2 and 3, threaded member 102 includes a head portion 110, an elongated threaded body portion 112 extending axially from head portion 110, and at least one banking feature, or anti-rotation feature 114. Alternatively, threaded member 102 may be free of head portion 110. For example, and without limitation, threaded member 102 may be a threaded rod, a bolt, a screw, or any other threaded component that enables fastener assembly 100 to function as described herein.

In the exemplary embodiment, anti-rotation features 114 includes a pair of opposing longitudinally extending sections formed in threaded body portion 112. It is contemplated that anti-rotation features 114 include, for example, and without limitation, flats, notches, grooves, or any other feature that enables threaded member 102 to function as described herein. Threaded body portion 112 has a diameter "D," defining a size of threaded member 102. In the exemplary embodiment, anti-rotation features 114 include a pair of flat portions that are parallel to each other and are spaced apart a width "W," which is smaller than diameter "D." Anti-rotation features 114 are substantially equal in size and shape, and extend along threaded body portion 112 from an end 116 of threaded member 102 a predefined length "L." It is contemplated that anti-rotation features 114 can extend any length "L" along threaded body portion 112, up to and including extending to head portion 110. In the exemplary embodiment, as shown in FIG. 2, head portion 110 is a hexagonal head. Alternatively, head portion 110 is any form, for example, and without limitation, a spline head, a socket cap, a tulip head, and a pan head, that enables fastener assembly 100 to function as described herein.

Figure 4:
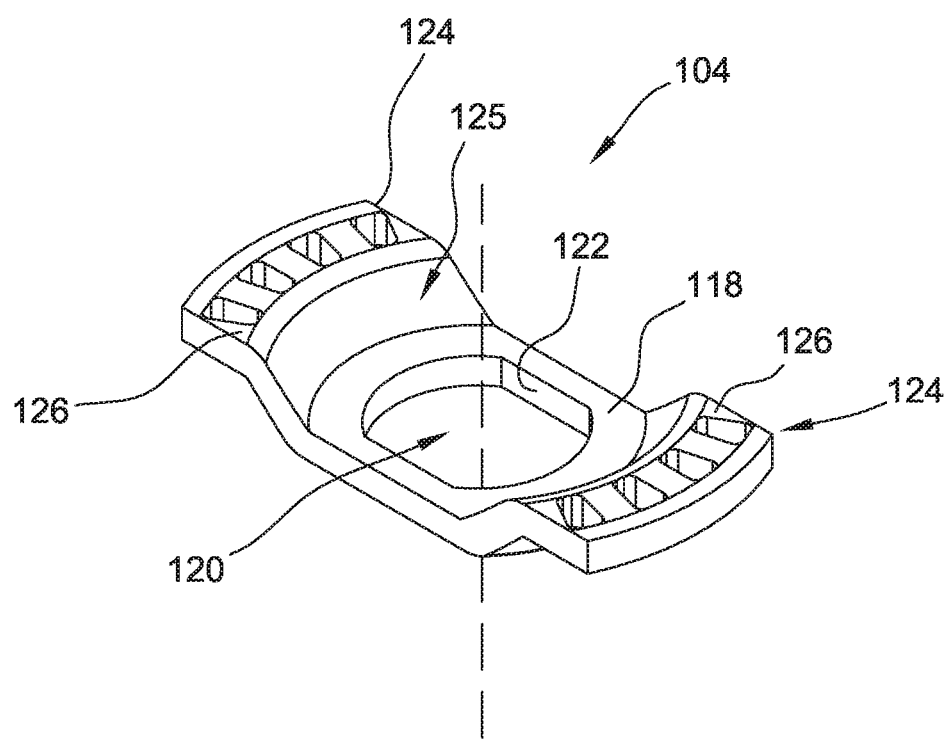
FIG. 4 is a perspective view of a lock washer of the fastener assembly of FIG. 1.
Figure 5:
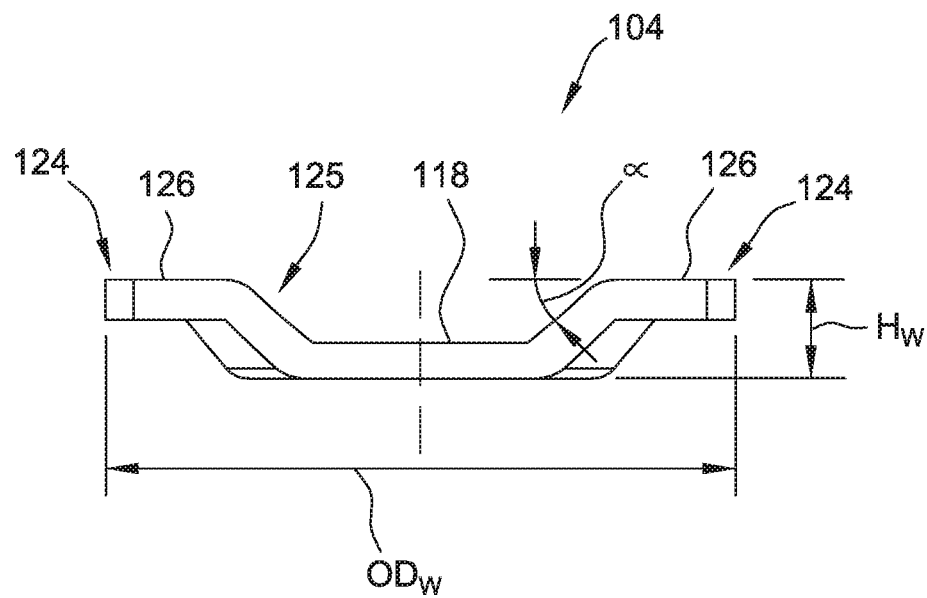
FIG. 5 is a front view of the lock washer of FIG. 4.
Figure 6:
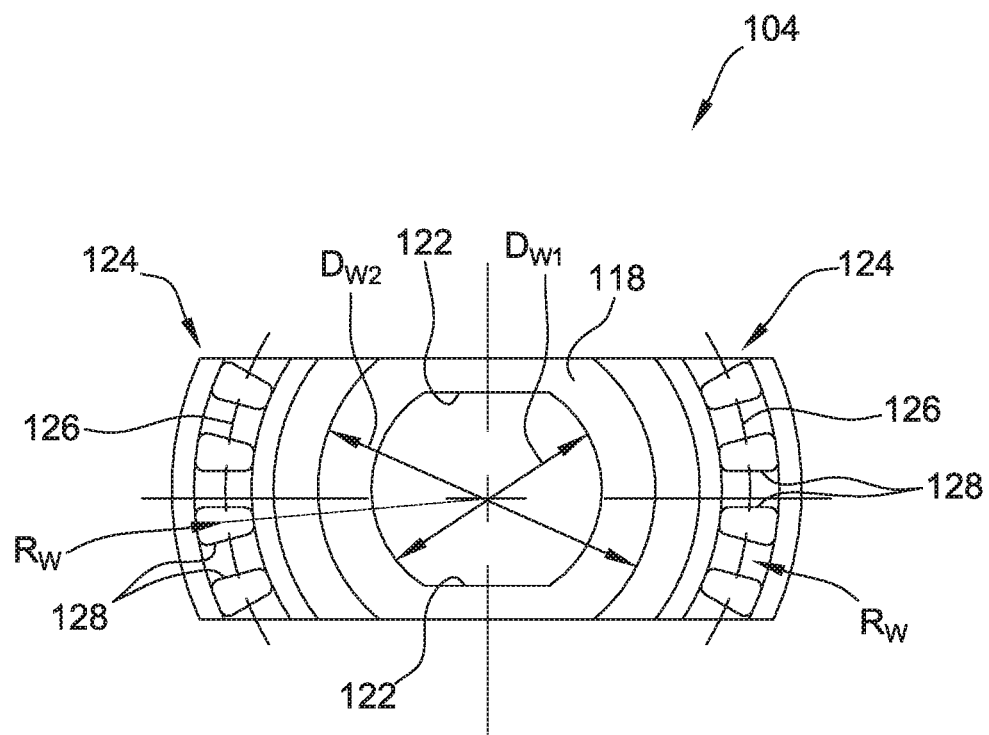
FIG. 6 is a top view of the lock washer of FIG. 4.

With reference to FIGS. 1 and 2, lock washer 104 is configured to slidably couple to anti-rotation features 114 of threaded body portion 112 for axial movement along threaded body portion 112. Anti-rotation features 114 facilitate rotationally fixing lock washer 104 relative to the threaded member 102. With reference to FIGS. 4-6, lock washer 104 includes a central portion 118 defining an axial aperture 120 therethrough. Axial aperture 120 is sized to facilitate freely sliding lock washer 104 onto threaded body portion 112 of threaded member 102. As such, axial aperture 120 has a diameter "$D_{w1}$" slightly greater than diameter "D" of threaded body portion 112. Axial aperture 120 also includes an anti-rotation structure 122 configured to engage anti-rotation feature 114 of threaded member 102. It is contemplated that anti-rotation structure 122 includes, for example, and without limitation, a finger, member or any other component configured to engage anti-rotation feature 114, for example, flats, notches, or grooves. In the exemplary embodiment, anti-rotation structure 122 includes a pair of opposing flat inner surfaces sized and shaped to correspond to the pair of opposing longitudinally extending anti-rotation features 114 of threaded body portion 112. Anti-rotation features 114 slidably couple with anti-rotation structures 122 of lock washer 104 to rotationally fix lock washer 104 when threaded body portion 112 is inserted in axial aperture 120. As such, lock washer 104 moves freely along threaded body portion 112 in the axial direction.

Figure 7:
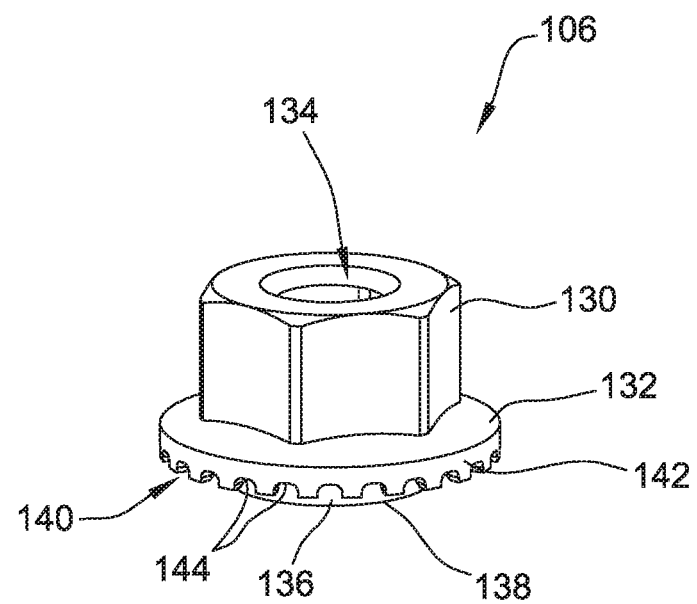
FIG. 7 is a perspective view of a lock nut of the fastener assembly of FIG. 1.
Figure 8:
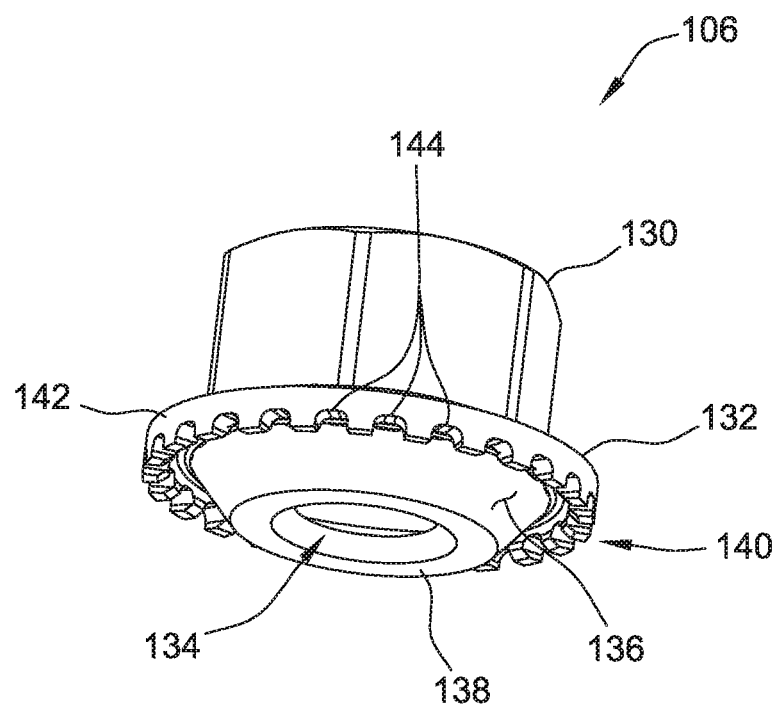
FIG. 8 is a lower perspective view of the lock nut of FIG. 7.

In the exemplary embodiment, lock washer 104 includes an outer portion 124 having an outer diameter or width "$OD_w$." In the exemplary embodiment, outer portion 124 includes a pair of opposing outer portions 124 that generally define an outer circumference of lock washer 104. Alternatively, outer portion 124 can be a full circumferential portion or any number of smaller radial portions or tabs that enable lock washer 104 to function as described herein. In the exemplary embodiment, outer portion 124 includes a pair of opposing outer tabs. Outer portions 124 extend upward from central portion 118. In particular, outer portions 124 extend upward from a boundary diameter "$D_{w2}$" and at an angle "$\alpha$" defined to correspond to a mating surface of lock nut 106 forming a curved tapered portion 125 for receiving a conical bearing surface 136 (shown in FIGS. 7-9) of lock nut 106. As such, diameter "$D_{w2}$" corresponds to a size of lock nut 106, and angle "$\alpha$" is any angle that enables lock washer 104 to couple to conical bearing surface 136 of lock nut 106, as described herein. Outer portions 124 extend upward a predetermined height "$H_w$," which corresponds to a size of lock nut 106, such that lock washer 104 couples to lock nut 106, as described herein. Outer portions 124 include a top surface 126 that is substantially parallel to central portion 118. A plurality of locking apertures 128 are defined at least partially through top surface 126. Locking apertures 128 are circumferentially equally spaced and located on a radial line at radial distance "$R_w$" from a center point of lock washer 104. In the exemplary embodiment, locking apertures 128 are trapezoidal in shape to correspond to teeth 144 (shown in FIGS. 7-9) of lock nut 106. Alternatively, locking apertures 128 have any shape and size that enables fastener assembly 100 to function as described herein.

Figure 9A:
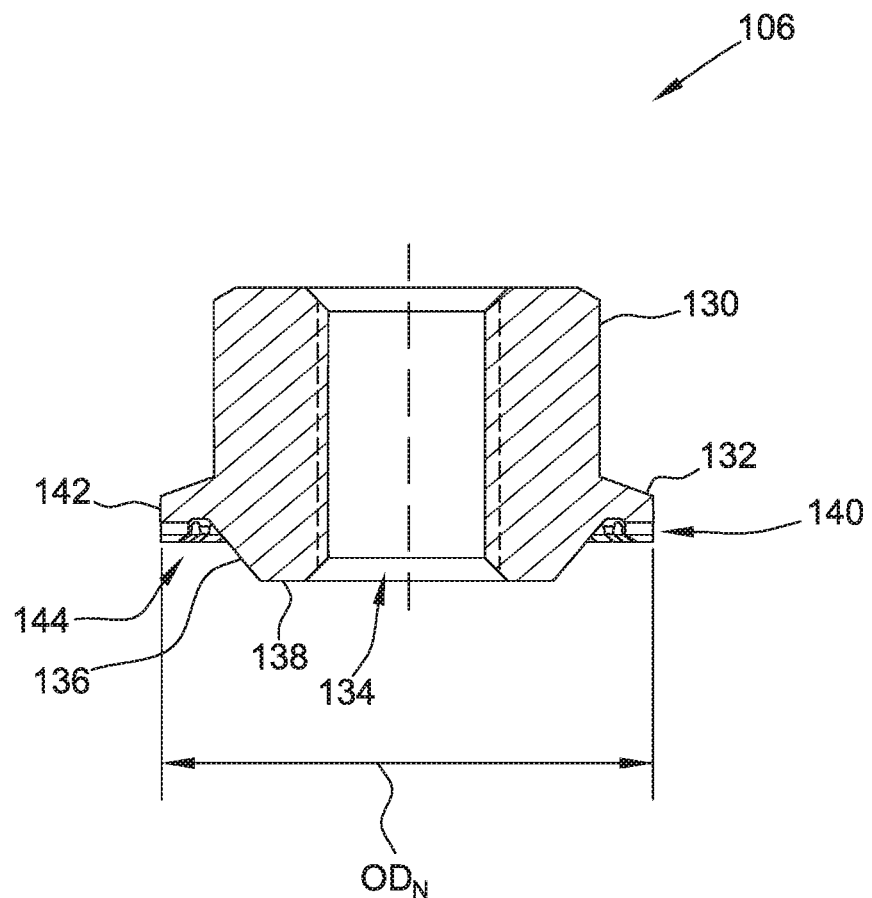
FIG. 9A is a sectional view of the lock nut of FIG. 7.
Figure 9B:
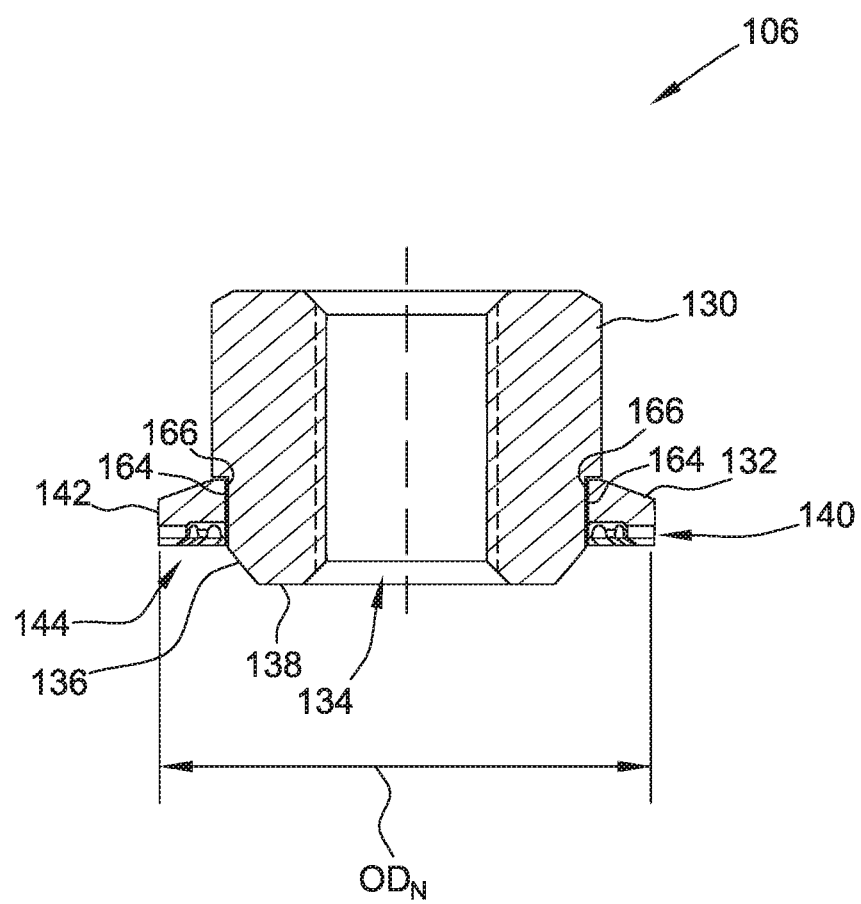
FIG. 9B is a sectional view of an alternative embodiment of the lock nut of FIG. 7.

With reference to FIGS. 1 and 2, lock nut 106 is configured to be threadably received by threaded member 102 over threaded body portion 112 and is rotationally free or rotationally fixed relative to threaded member 102 depending upon whether lock nut 106 is engaged with or disengaged from lock washer 104. With reference to FIGS. 7-9B, lock nut 106 includes a body 130 and a transversely extending flange 132 proximate a first end 138 of lock nut 106. With reference to FIG. 9A, in the exemplary embodiment, flange 132 is integrally formed with body 130. Alternatively, as shown in FIG. 9B, flange 132 is separately formed from body 130 and is releasably coupled to body 130. In such an embodiment, flange 132 is rotationally fixed to body 130 via engagement of one or more anti-rotation features 164 to one or more corresponding anti-rotation structures 166 of body 130 of lock nut 106. For example, and without limitation, anti-rotation features 164 can include a tab configured to couple to a slot formed in body 130, or can include a generally planar surface configured to couple to a corresponding planar surface formed on body 130. In alternative embodiments, lock nut 106 is free of flange 132. With reference to FIGS. 7-9A, in the exemplary embodiment, flange 132 has a diameter "$OD_n$." Body 130 includes a threaded bore 134 extending axially through lock nut 106. Lock nut 106 includes a conical bearing surface 136 formed at first end 138, below flange 132. In the exemplary embodiment, conical bearing surface 136 is configured to engage curved tapered portion 125 of lock washer 104. Body 130 is formed as a hexagonal-shaped body, although other configurations of body 130 are contemplated.

In the exemplary embodiment, flange 132 includes a peripherally extending lip 140 that projects downward from flange 132 generally adjacent a circular outer edge 142 of flange 132. Lock nut 106 includes a plurality of axially extending teeth 144 formed in lip 140. In particular, teeth 144 extend radially inward from circular outer edge 142 of flange 132 in equal, circumferentially-spaced relationships to each other and project downward in an axial direction. Alternatively, in embodiments without flange 132, axially extending teeth 144 are formed in body 130. In the exemplary embodiment, teeth 144 include a plurality of arcuate (in circumferential extension) channels that extend radially inward from circular outer edge 142 through lip 140. It is understood that, in other embodiments, teeth 144 are configured to have any other suitable shape that enables lock nut 106 to function as described herein. In the exemplary embodiment, lock nut 106 includes twenty-four teeth 144. Alternatively, lock nut 106 has any number of teeth 144 that enable lock nut 106 to function as described herein.

In the exemplary embodiment, threaded member 102, lock washer 104, and lock nut 106 are fabricated from a metal, for example, and without limitation, steel, aluminum, titanium, or a superalloy. Alternatively, threaded member 102, lock washer 104, and lock nut 106 are fabricated from any material that enables fastener assembly 100 to function as described herein, such as, without limitation, composite materials, resins, fiber reinforced resins, plastics, and fiber reinforced plastics.

Figure 10:
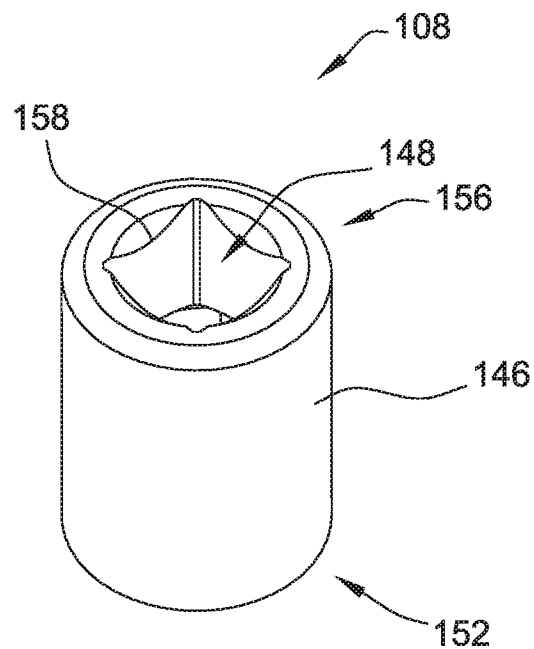
FIG. 10 is an upper perspective view of a tool for use with the fastener assembly of FIG. 1.
Figure 11:
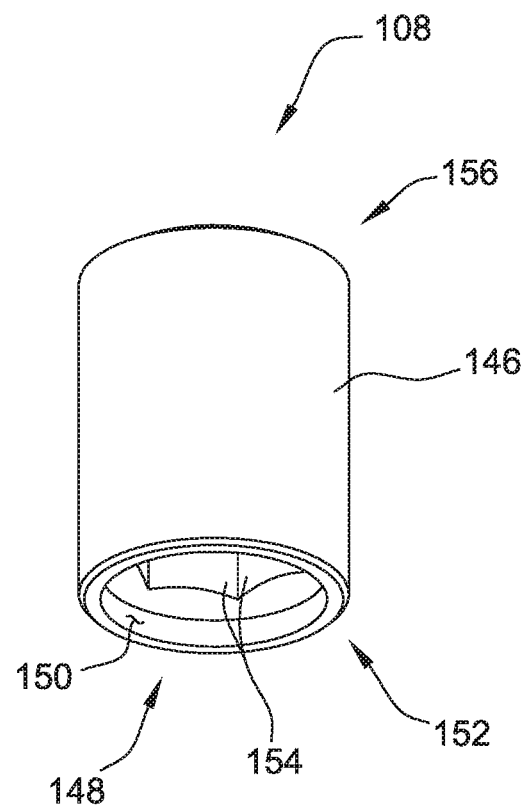
FIG. 11 is a lower perspective view of the tool of FIG. 10.
Figure 12:
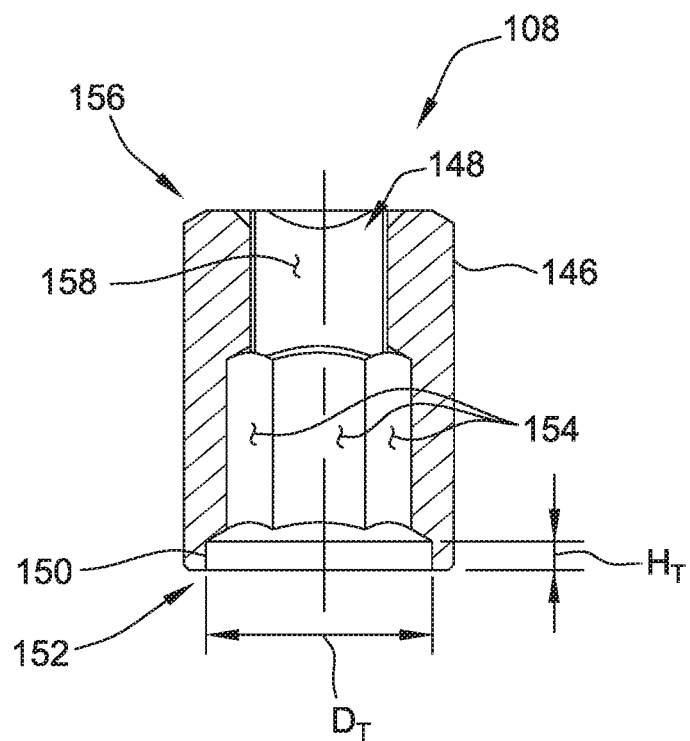
FIG. 12 is a sectional view of the tool of FIG. 10.

With reference to FIG. 2, tool 108 is configured for engaging both lock nut 106 and lock washer 104 to facilitate installation and removal of lock nut 106 from fastener assembly 100. With reference to FIGS. 10-12, in the exemplary embodiment, tool 108 includes a body 146 having a stepped bore 148 extending axially therethrough. Stepped bore 148 includes a cylindrical portion 150 at a first end 152 of body 146. Cylindrical portion 150 has a diameter "$D_t$" configured to receive flange 132 of lock nut 106 therein. In particular, diameter "$D_t$" is greater than diameter "$OD_n$" of outer edge 142 of flange 132 to enable lock nut 106 to slide freely into tool 108 in an axial direction. Cylindrical portion 150 extends axially along stepped bore 148 a predetermined distance "$H_t$" configured to facilitate receiving the entirety of lock nut 106 in stepped bore 148 such that body 146 engages outer portions 124 of lock washer 104, as is described herein. Stepped bore 148 also includes wrenching surfaces 154 extending from cylindrical portion 150 toward a second end 156 of body 146. At second end 156, stepped bore 148 includes a driver connection 158 for receiving driving torque from a driving member (not shown), such as a ratchet. Wrenching surfaces 154 correspond in shape and size, are configured, to engage body 130 of lock nut 106. In the exemplary embodiment, driver connection 158 is a square-shaped bore. Alternatively, driver connection 158 has any shape that enables tool 108 to function as described herein.

Figure 13:
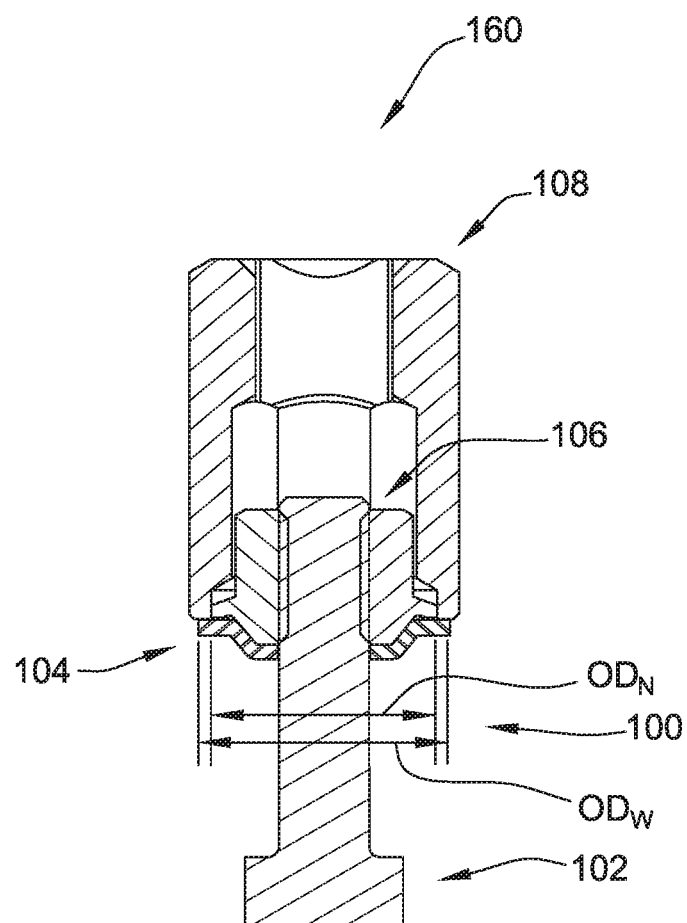
FIG. 13 is a sectional view of the fastener assembly of FIG. 1, showing the lock washer in a first orientation.
Figure 14:
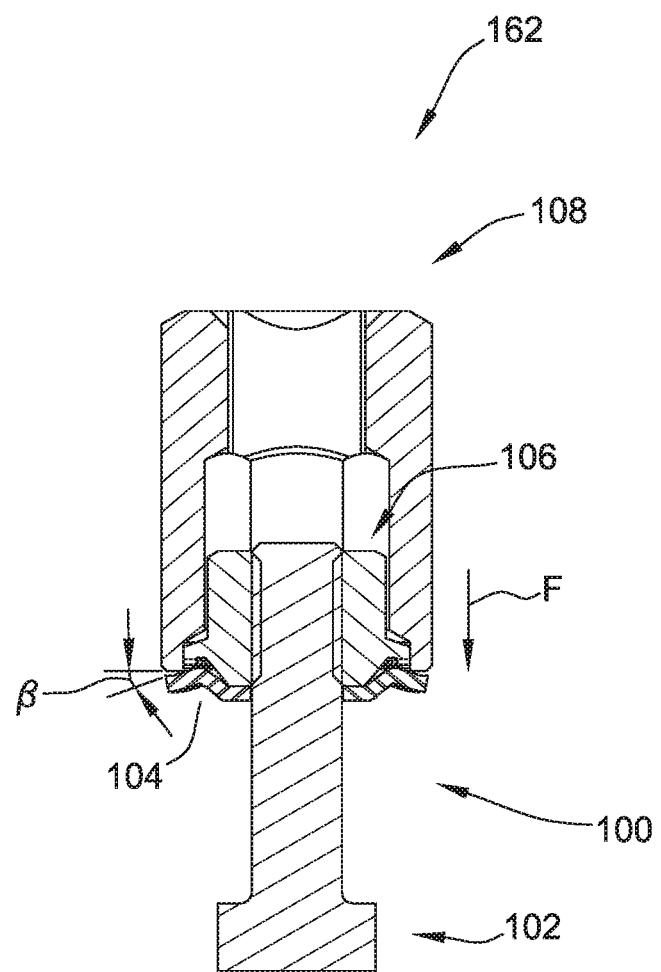
FIG. 14 is a sectional view of the fastener assembly of FIG. 1, showing the lock washer in a second orientation.

FIG. 13 is a sectional view of fastener assembly 100 showing lock washer 104 in a first orientation 160, where lock nut 106 is engaged with lock washer 104 and rotationally fixed. FIG. 14 is a sectional view of fastener assembly 100 showing lock washer 104 in a second orientation 162, where tool 108 is engaged with outer portions 124 of lock washer 104. In the exemplary embodiment, lock washer 104 is movable between first orientation 160 and second orientation 162. In first orientation 160, teeth 144 formed in flange 132 of lock nut 106 engage (i.e., extend into) locking apertures 128 defined in outer portions 124 of lock washer 104. Engaging teeth 144 with locking apertures 128 facilitates rotationally fixing lock nut 106 relative to lock washer 104. In addition, lock washer 104 is rotationally fixed to threaded member 102 via the engagement of anti-rotation structures 122 to the pair of opposing longitudinally extending anti-rotation features 114 of threaded body portion 112 of threaded member 102. Accordingly, lock nut 106 is rotationally fixed relative to threaded member 102 in first orientation 160 of fastener assembly 100.

In the exemplary embodiment, "$OD_w$" is greater than "$OD_n$" such that tool 108 facilitates providing an axial force "F" to outer portions 124. Force "F" facilitates bending or flexing outer portions 124 from first orientation 160 to second orientation 162. Second orientation 162 is offset from first position 160 by an angle "β" of sufficient magnitude to facilitate disengaging teeth 144 from locking apertures 128, thereby allowing lock nut 106 to freely rotate relative to lock washer 104 and threaded member 102.

Figure 15:
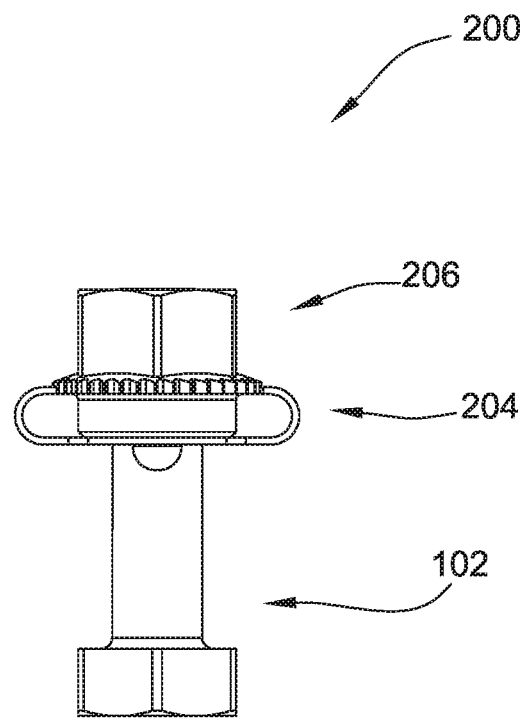
FIG. 15 is a side view of an alternative exemplary embodiment of a fastener assembly.
Figure 16:
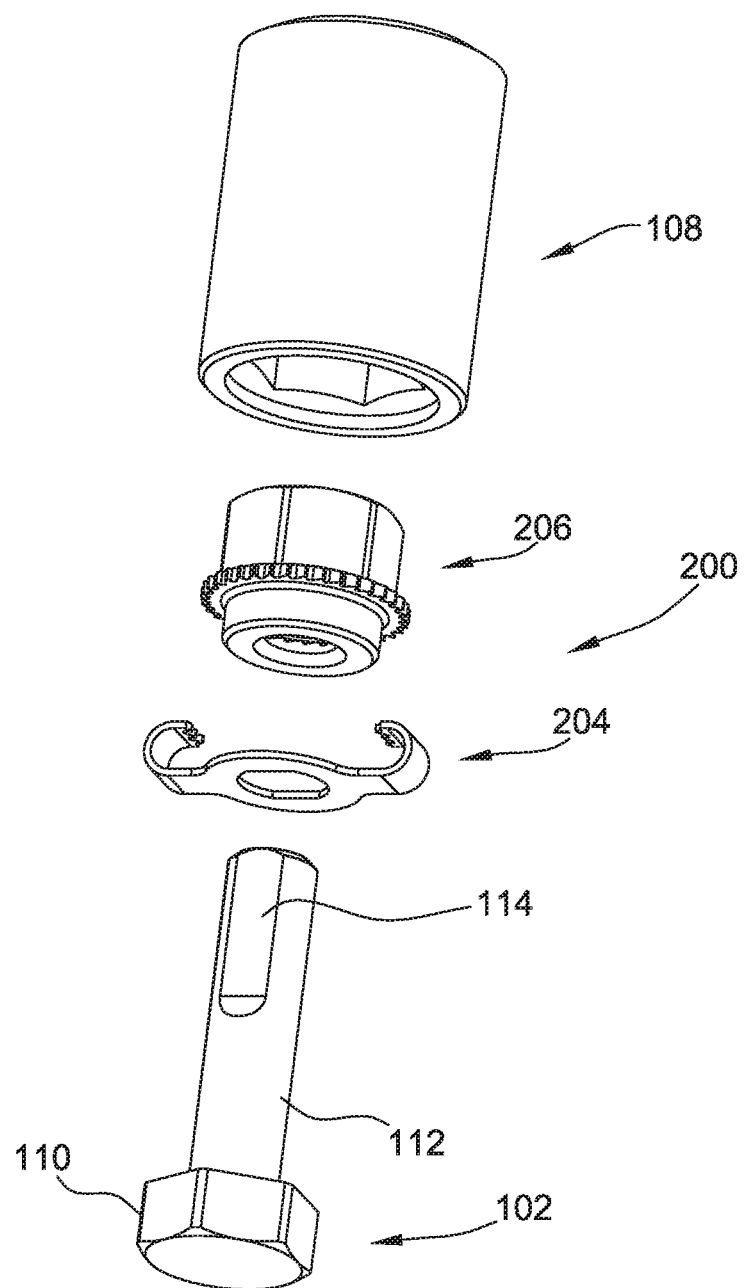
FIG. 16 is an exploded perspective view of the fastener assembly shown in FIG. 15, including a tool for use with the fastener assembly.
Figure 17:
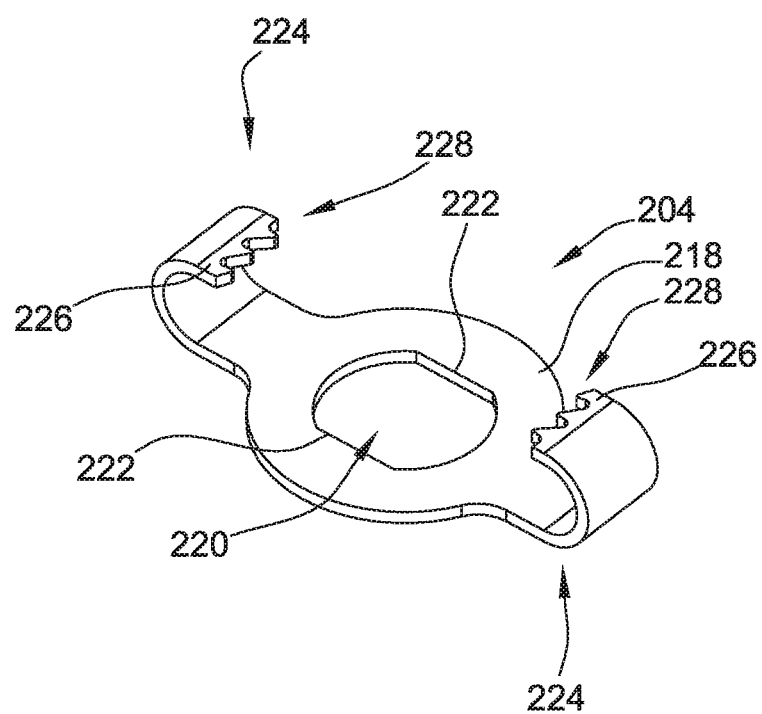
FIG. 17 is a perspective view of a lock washer of the fastener assembly of FIG. 15.
Figure 18:
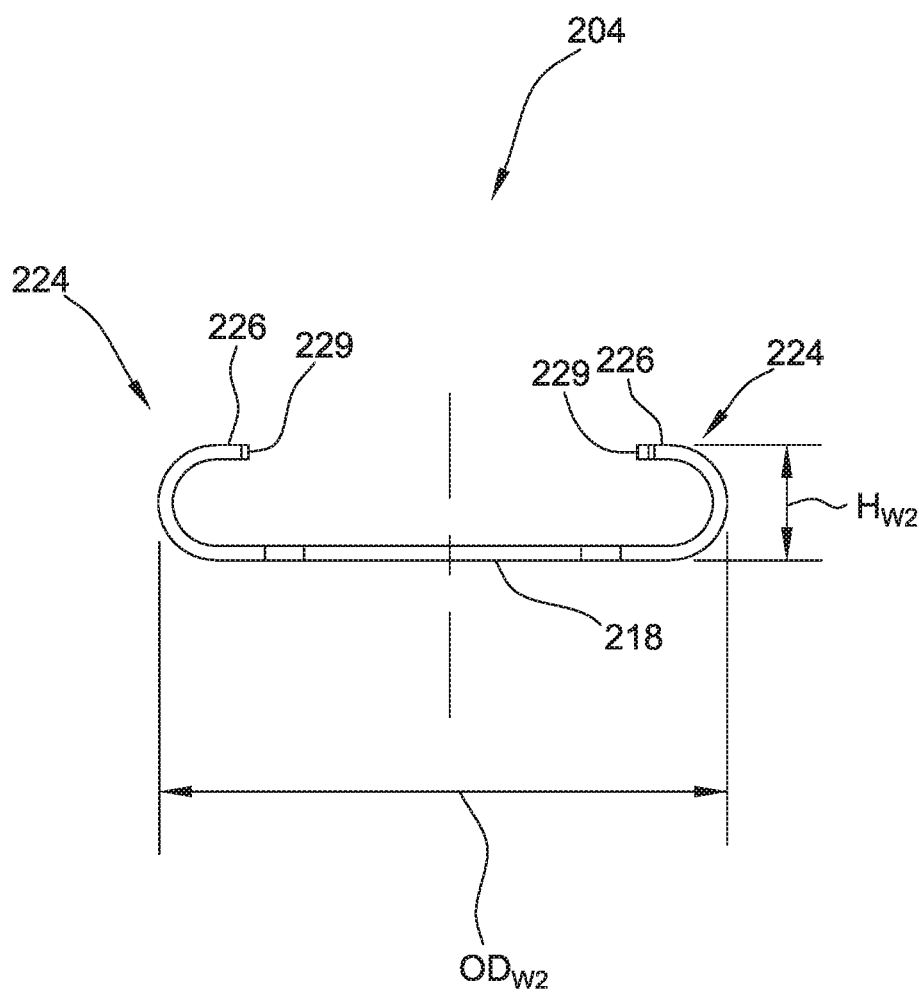
FIG. 18 is a front view of the lock washer of FIG. 17.
Figure 19:
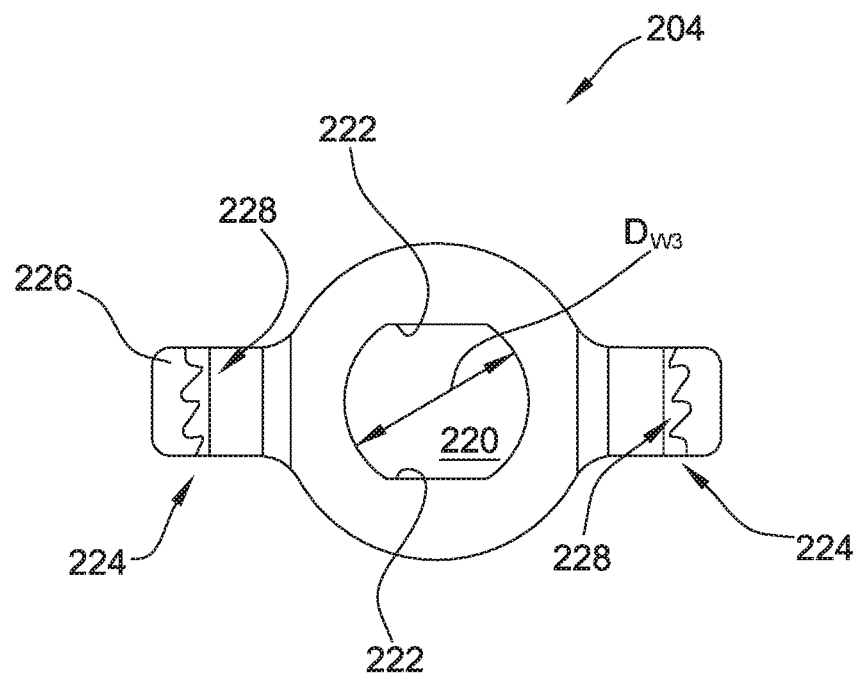
FIG. 19 is a top view of the lock washer of FIG. 17.

FIG. 15 is a side view of an alternative exemplary embodiment of a fastener assembly 200. FIG. 16 is an exploded perspective view of fastener assembly 200, including tool 108 for use with fastener assembly 200. In the exemplary embodiment, fastener assembly 200 includes threaded member 102, a lock washer 204, a lock nut 206, and tool 108. With reference to FIGS. 15 and 16, lock washer 204 is configured to slidably couple to anti-rotation features 114 of threaded body portion 112 for axial movement along threaded body portion 112. Anti-rotation features 114 facilitate rotationally fixing lock washer 204 relative to the threaded member 102. With reference to FIGS. 17-19, lock washer 204 includes a central portion 218 defining an axial aperture 220 therethrough. Axial aperture 220 is sized to facilitate freely sliding lock washer 204 onto threaded body portion 112 of threaded member 102. As such, axial aperture 220 has a diameter "$D_{W3}$" slightly greater than diameter "D" of threaded body portion 112. Axial aperture 220 also includes an anti-rotation structure 222 configured to engage anti-rotation feature 114 of threaded member 102. It is contemplated that anti-rotation structure 222 includes, for example, and without limitation, a finger, member, or any other component configured to engage anti-rotation feature 114, for example, flats, notches, or grooves. In the exemplary embodiment, anti-rotation structure 222 includes a pair of opposing flat inner surfaces sized and shaped to correspond to the pair of opposing longitudinally extending anti-rotation features 114 of threaded body portion 112. Anti-rotation features 114 slidably couple with anti-rotation structures 222 of lock washer 204 to rotationally fix lock washer 204 when threaded body portion 112 is inserted in axial aperture 220. As such, lock washer 204 moves freely along threaded body portion 112 in the axial direction.

In the exemplary embodiment, lock washer 204 includes an outer portion 224 having an outer diameter or width "$OD_{w2}$." In the exemplary embodiment, outer portion 224 includes a pair of opposing outer tabs that generally define the outer width "$OD_{w2}$" of lock washer 204. Alternatively, outer portion 224 can be a full circumferential portion or any number of smaller radial portions or tabs that enable lock washer 204 to function as described herein. In the exemplary embodiment, outer portion 224 includes a pair of opposing outer tabs. Outer portions 224 extend outward from central portion 218 and turn upward in an axial direction, curving back toward central portion 218. In particular, outer portions 224 form a 180° radius, such that outer portions 224 point back toward central portion 218. Outer portions 224 extend upward a predetermined height "$H_{w2}$," (shown in FIG. 18), which corresponds to a size of lock nut 206, such that lock washer 204 couples to lock nut 206, as described herein. Outer portions 224 include a top surface 226 that is substantially parallel to central portion 218. A plurality of locking teeth 228 are defined in a respective end 229 of each outer portion 224. Teeth 228 are sized and shaped to correspond to teeth 244 (shown in FIGS. 20-22) of lock nut 206. In the exemplary embodiment, teeth 228 are configured to facilitate preventing counter-clockwise rotation of lock nut 206. Alternatively, teeth 228 are configured to facilitate preventing rotation of lock nut 206 in the clockwise direction, or both the counter-clockwise and the clockwise directions.

Figure 20:
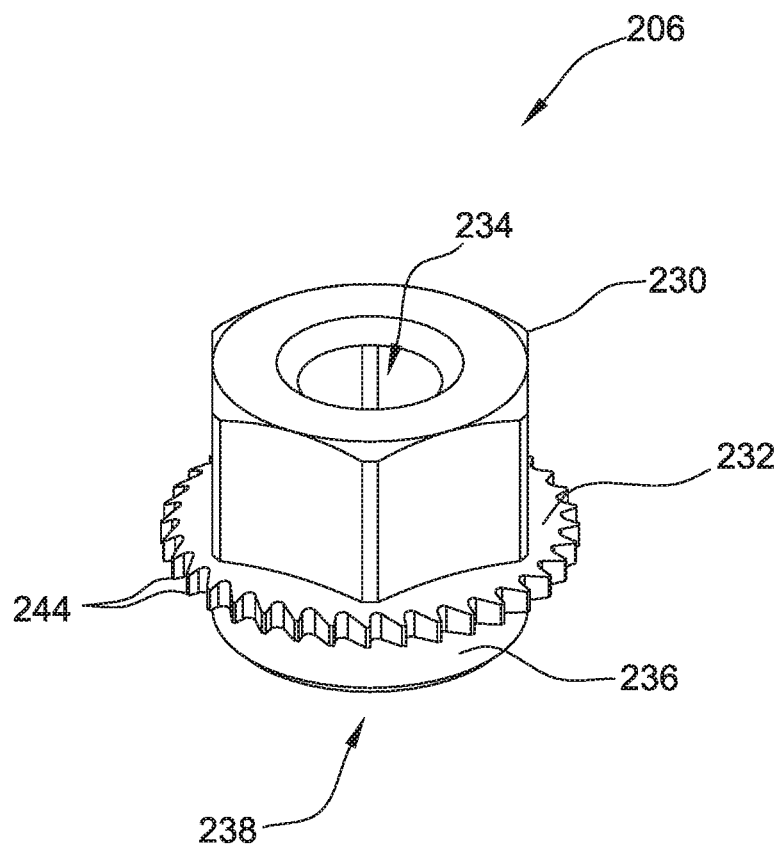
FIG. 20 is a perspective view of a lock nut of the fastener assembly of FIG. 15.
Figure 21:
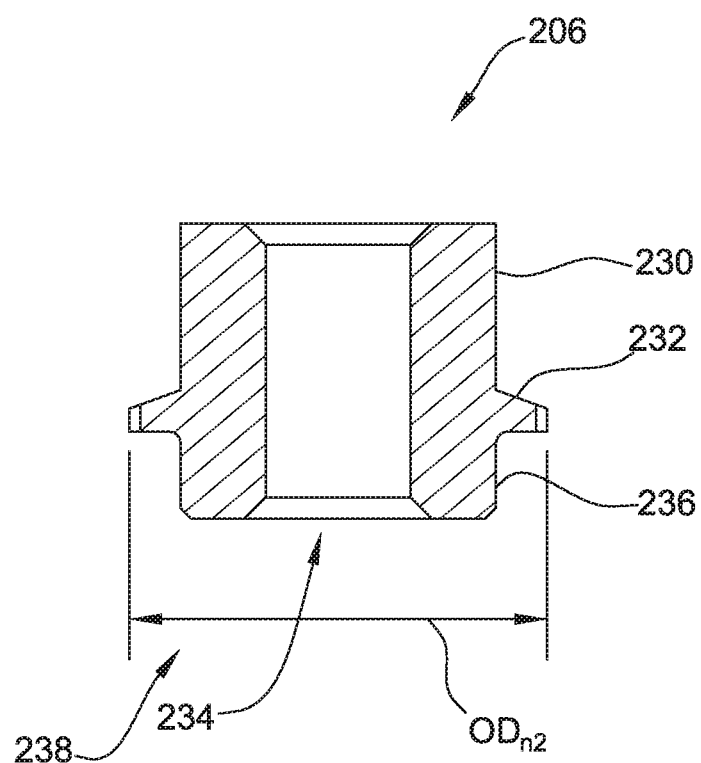
FIG. 21 is a sectional view of the lock nut of FIG. 20.
Figure 22:
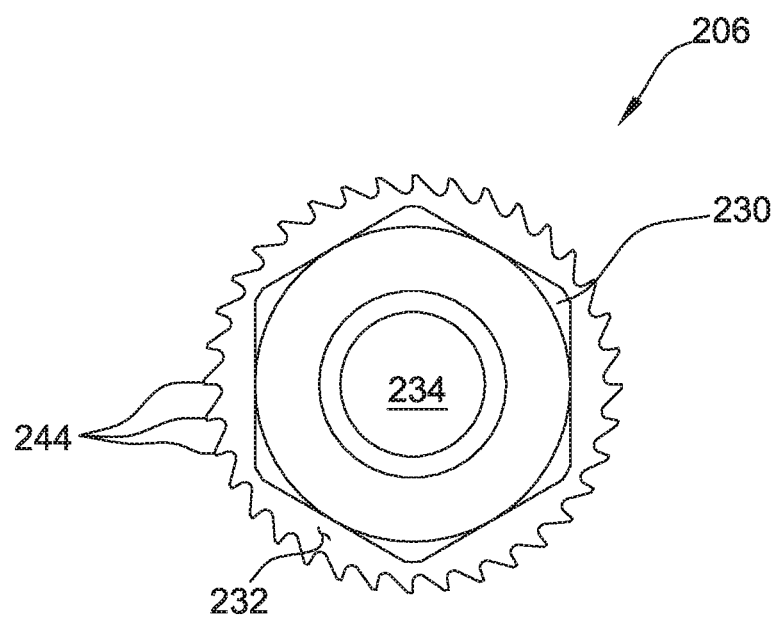
FIG. 22 is a top view of the lock nut of FIG. 20.

With reference to FIGS. 15 and 16, lock nut 206 is configured to be threadably received by threaded member 102 over threaded body portion 112 and is rotationally free or rotationally fixed relative to threaded member 102 depending upon whether lock nut 206 is engaged with or disengaged from lock washer 204. With reference to FIGS. 20-22, lock nut 206 includes a body 230 and a transversely extending flange 232 proximate a first end 238 of lock nut 206. In the exemplary embodiment, flange 232 is integrally formed with body 230. Alternatively, as described above, flange 232 can be separately formed from body 230 and releasably coupled to body 230. In such an embodiment, flange 232 is rotationally fixed to body 230 via engagement of one or more anti-rotation features, such as anti-rotation features 164, to one or more corresponding anti-rotation structures, such as anti-rotation structures 166. In alternative embodiments, lock nut 206 is free of flange 232. In the exemplary embodiment, body 230 includes a threaded bore 234 extending axially through lock nut 206. Lock nut 206 includes a cylindrical bearing surface 236 formed at first end 238, below flange 232. In the exemplary embodiment, cylindrical bearing surface 236 is configured to engage central portion 218 of lock washer 204. Body 230 is formed as a hexagonal-shaped body, although other configurations of body 230 are contemplated.

In the exemplary embodiment, flange 232 includes a plurality of radially extending teeth 244 formed through flange 232. In particular, teeth 244 extend radially outward from body 230 in equal, circumferentially-spaced relationships to each other, and define an outer diameter "$OD_{n2}$." Teeth 244 are configured to facilitate preventing counter-clockwise rotation of lock nut 206 when engaged with locking teeth 228 of lock washer 204. Alternatively, teeth 244 are configured to facilitate preventing rotation of lock nut 206 in the clockwise direction, or both the counter-clockwise and the clockwise directions. In the exemplary embodiment, lock nut 206 includes thirty-six teeth 244. Alternatively, lock nut 206 has any number of teeth 244 that enable lock nut 206 to function as described herein.

In the exemplary embodiment, lock washer 204 and lock nut 206 are fabricated from a metal, for example, and without limitation, steel, aluminum, titanium, or a superalloy. Alternatively, threaded member 102, lock washer 204, and lock nut 206 are fabricated from any material that enables fastener assembly 200 to function as described herein, such as, without limitation, composite materials, resins, fiber reinforced resins, plastics, and fiber reinforced plastics.

Figure 23:
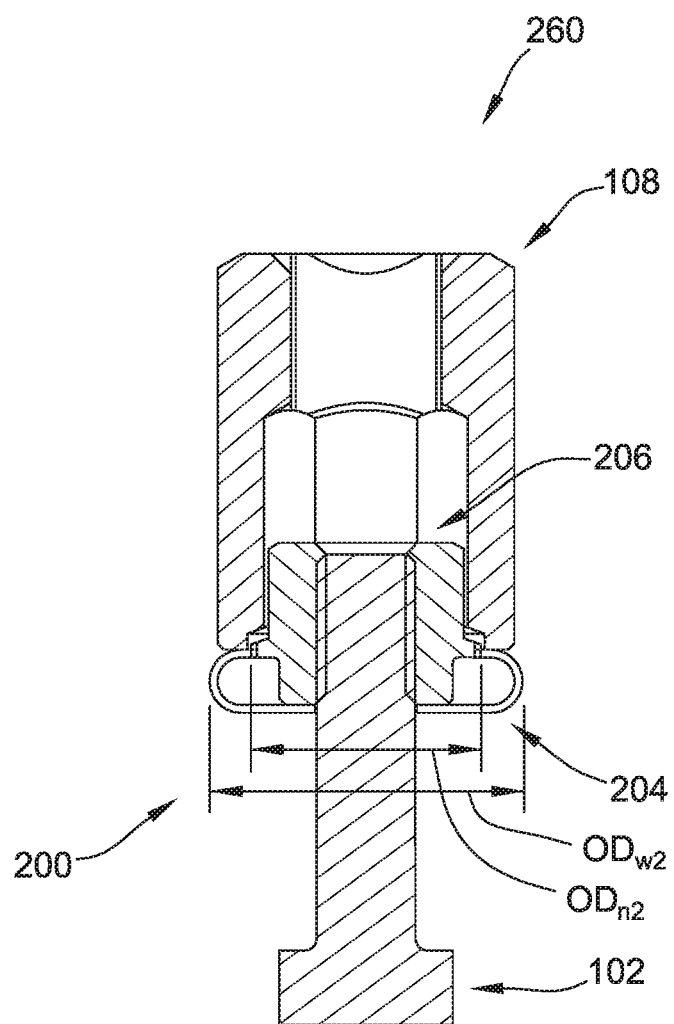
FIG. 23 is a sectional view of the fastener assembly of FIG. 15, showing the lock washer in a first orientation.
Figure 24:
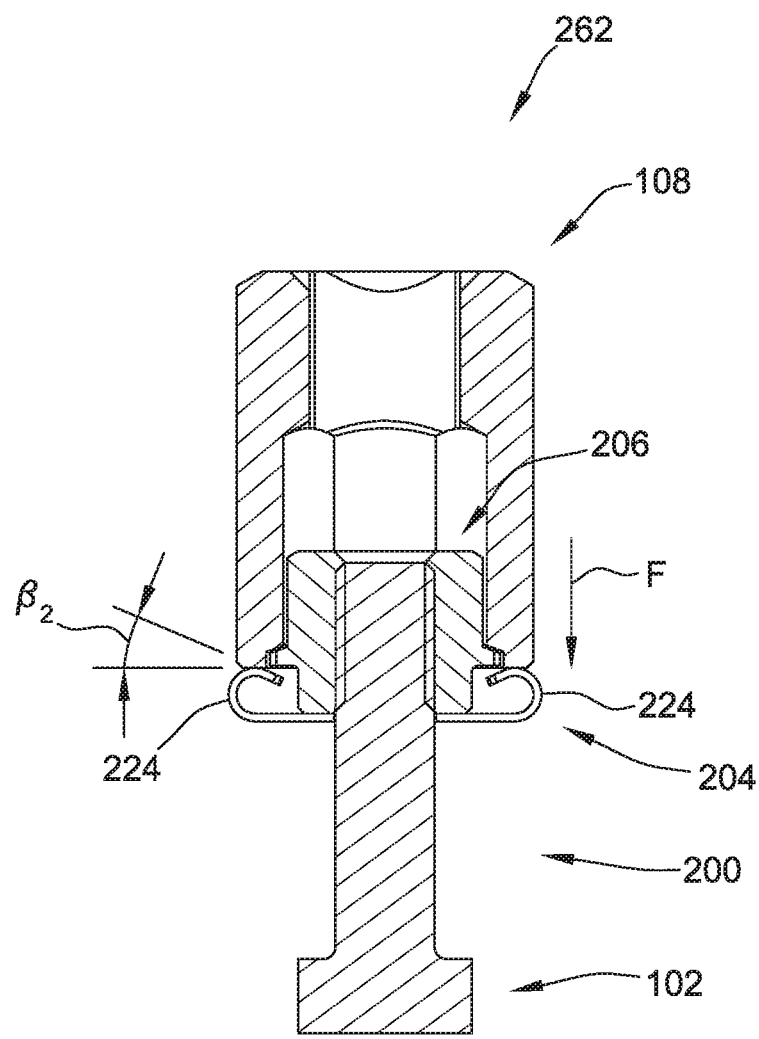
FIG. 24 is a sectional view of the fastener assembly of FIG. 15, showing the lock washer in a second orientation.

FIG. 23 is a cross-sectional side elevation view of fastener assembly 200 showing lock washer 204 in a first orientation 260, where lock nut 206 is engaged with lock washer 204 and rotationally fixed. FIG. 24 is a cross-sectional side elevation view of fastener assembly 200 showing lock washer 204 in a second orientation 262, where tool 108 is engaged with outer portions 224 of lock washer 204. In the exemplary embodiment, lock washer 204 is movable between first orientation 260 and second orientation 262. In first orientation 260, teeth 244 formed in flange 232 of lock nut 206 engage (i.e., mesh with) locking teeth 228 defined in outer portions 224 of lock washer 204. Engaging teeth 244 with locking teeth 228 facilitates rotationally fixing lock nut 206 relative to lock washer 204. In addition, lock washer 204 is rotationally fixed to threaded member 102 via the engagement of anti-rotation structures 222 to the pair of opposing longitudinally extending anti-rotation features 114 of threaded body portion 112 of threaded member 102. Accordingly, lock nut 206 is rotationally fixed relative to threaded member 102 in first orientation 260 of fastener assembly 200.

In the exemplary embodiment, "$OD_{w2}$" is greater than "$OD_{n2}$," such that tool 108 facilitates providing an axial force "F" to outer portions 224. More specifically, tool first end 152 of body 146 engages the respective ends 229 of outer portions 224 such that force "F" facilitates bending or flexing ends 229 of outer portions 224 from first orientation 260 to second orientation 262. Second orientation 262 is offset from first position 260 by an angle "$\beta_2$" of sufficient magnitude to facilitate disengaging locking teeth 228 from teeth 244 of lock nut 206, thereby facilitating lock nut 206 to freely rotate relative to lock washer 204 and threaded member 102.

Figure 25:
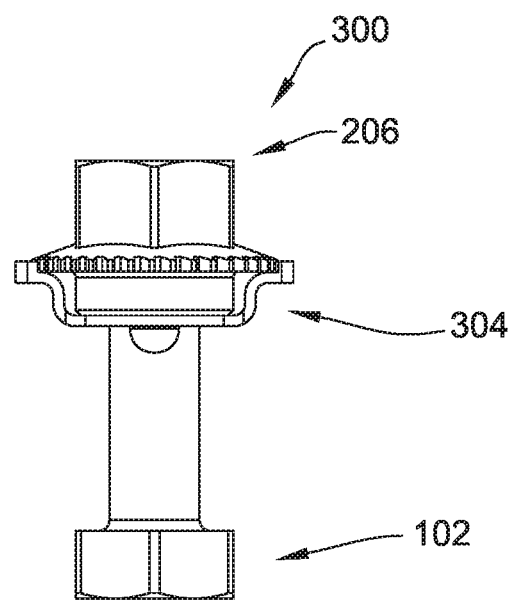
FIG. 25 is a side view of another alternative exemplary embodiment of a fastener assembly.
Figure 26:
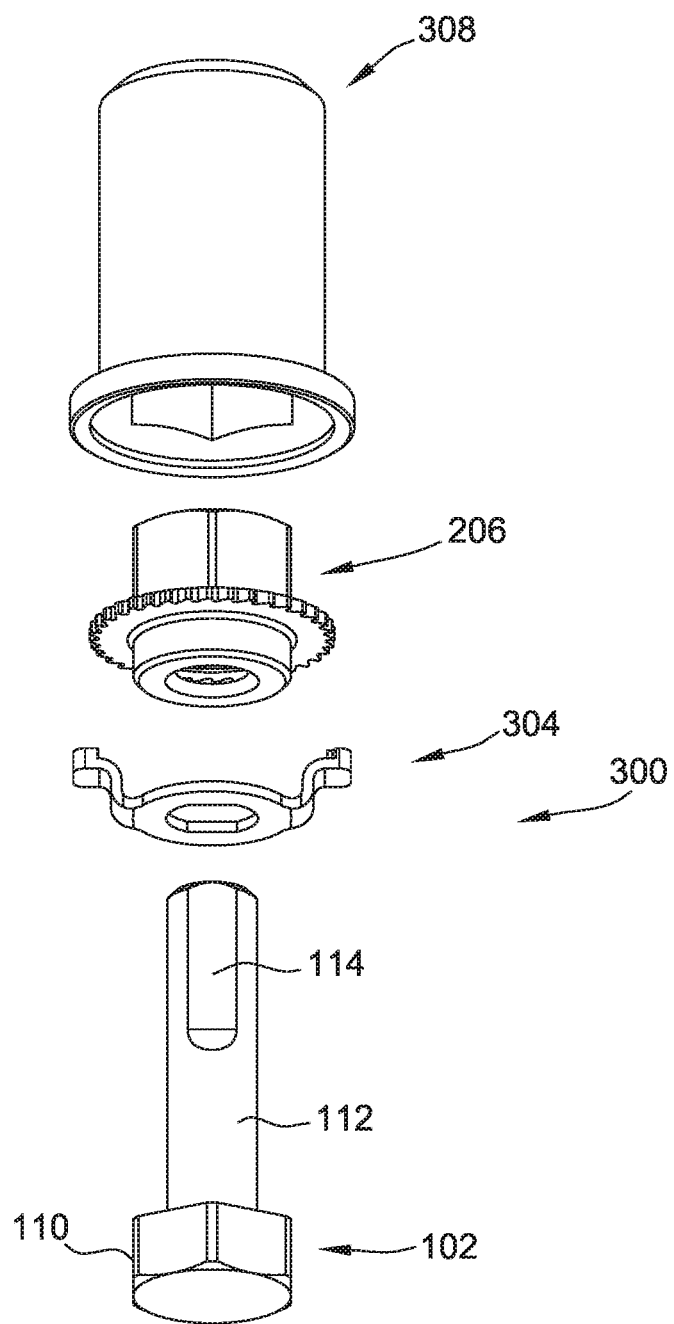
FIG. 26 is an exploded perspective view of the fastener assembly shown in FIG. 25, including a tool for use with the fastener assembly.
Figure 27:
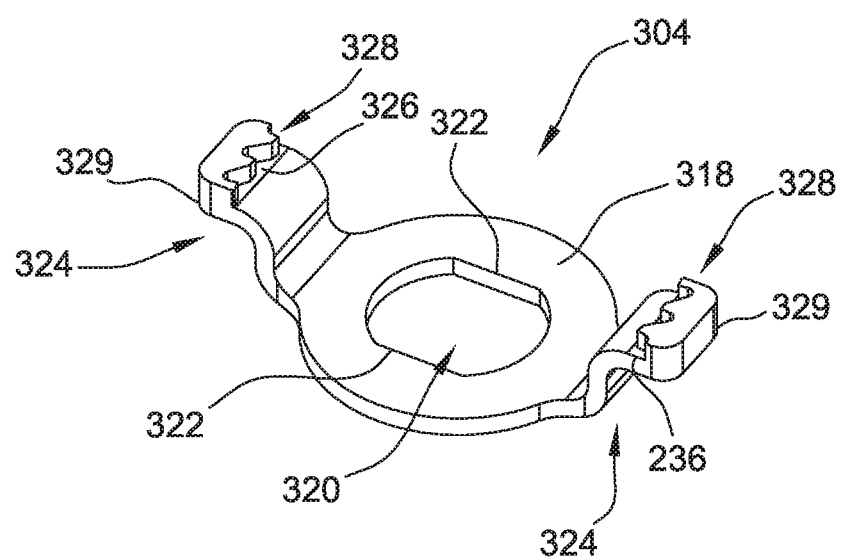
FIG. 27 is a perspective view of a lock washer of the fastener assembly of FIG. 25.
Figure 28:
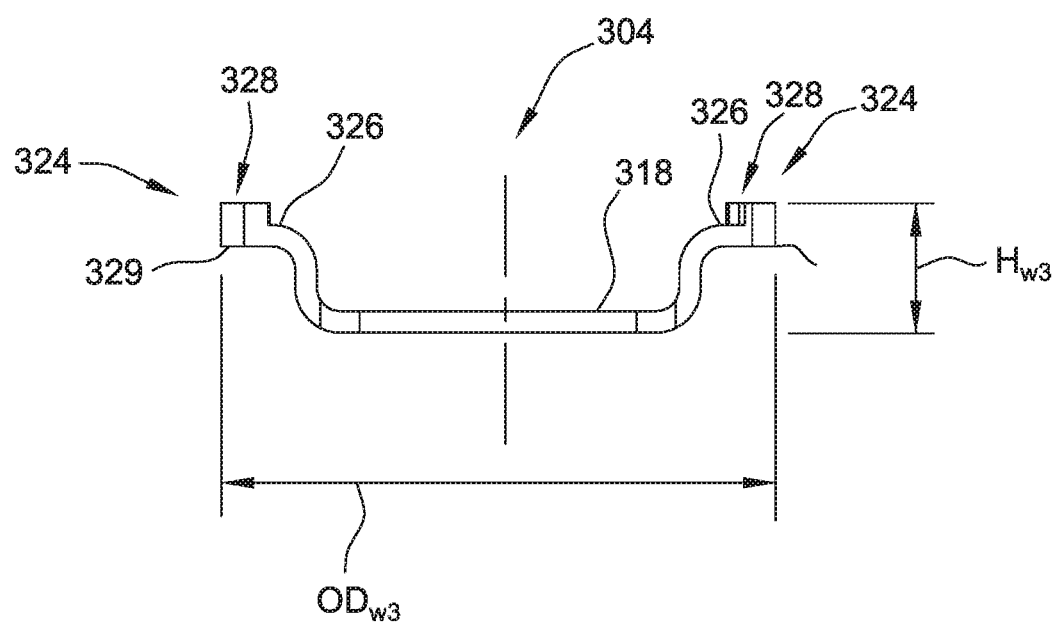
FIG. 28 is a front view of the lock washer of FIG. 27.
Figure 29:
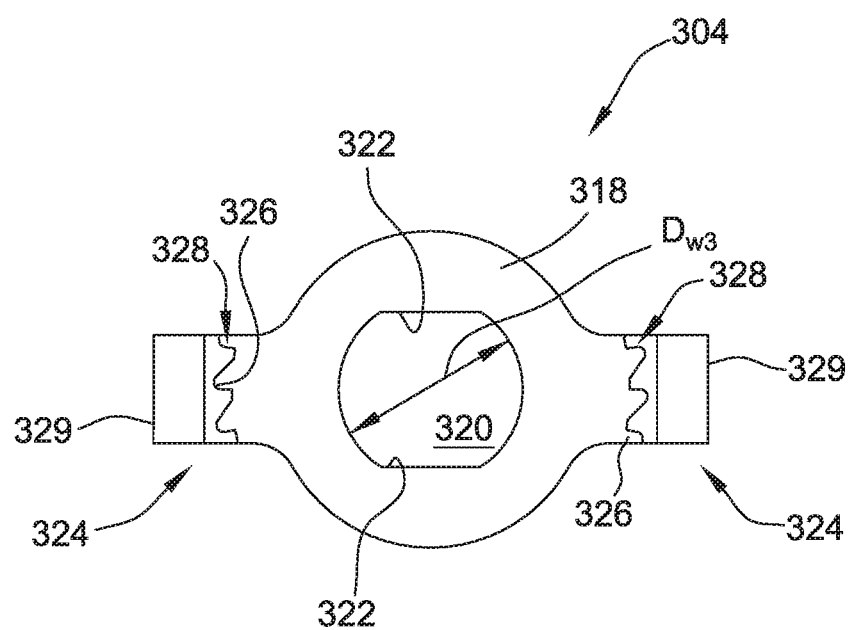
FIG. 29 is a top view of the lock washer of FIG. 27.

FIG. 25 is a side view of another alternative exemplary embodiment of a fastener assembly 300. FIG. 26 is an exploded perspective view of fastener assembly 300, including a tool 308 for use with fastener assembly 300. In the exemplary embodiment, fastener assembly 300 includes threaded member 102, a lock washer 304, lock nut 206, and a tool 308. With reference to FIGS. 25 and 26, lock washer 304 is configured to slidably couple to anti-rotation features 114 of threaded body portion 112 for axial movement along threaded body portion 112. Anti-rotation features 114 facilitate rotationally fixing lock washer 304 relative to the threaded member 102.

With reference to FIGS. 27-30, lock washer 304 includes a central portion 318 defining an axial aperture 320 therethrough. Axial aperture 320 is sized to facilitate freely sliding lock washer 304 onto threaded body portion 112 of threaded member 102. As such, axial aperture 320 has a diameter "$D_{w3}$" slightly greater than diameter "D" of threaded body portion 112. Axial aperture 320 also includes an anti-rotation structure 322 configured to engage anti-rotation features 114 of threaded member 102. It is contemplated that anti-rotation structure 322 includes, for example, and without limitation, a finger, member, or any other component configured to engage anti-rotation features 114, for example, flats, notches, or grooves. In the exemplary embodiment, anti-rotation structure 322 includes a pair of opposing flat inner surfaces sized and shaped to correspond to the pair of opposing longitudinally extending anti-rotation features 114 of threaded body portion 112. Anti-rotation features 114 slidably couple with anti-rotation structures 322 of lock washer 304 to rotationally fix lock washer 304 when threaded body portion 112 is inserted in axial aperture 320. As such, lock washer 304 moves freely along threaded body portion 112 in the axial direction.

In the exemplary embodiment, lock washer 304 includes an outer portion 324 having an outer diameter or width "$OD_{w3}$." In the exemplary embodiment, outer portion 324 includes a pair of opposing outer tabs that generally define the outer width "$OD_{w3}$" of lock washer 304. Alternatively, outer portion 324 can be a full circumferential portion or any number of smaller radial portions or tabs that enable lock washer 304 to function as described herein. In the exemplary embodiment, outer portion 324 includes a pair of opposing outer tabs that generally define the outer width "$OD_{w3}$" of lock washer 304. Outer portions 324 extend outward from central portion 318 and turn approximately 90° upward (i.e., substantially perpendicular to central portion 318) for a predetermined height "$H_{w3}$." Outer portions 324 then turn outward, defining an end portion 329 that is substantially parallel to central portion 318. Height "$H_{w3}$" corresponds to a size of lock nut 206, such that lock washer 304 couples to lock nut 206, as described herein. End portions 329 of outer portions 324 include a top surface 326 that is substantially parallel to central portion 318. A plurality of locking teeth 328 extend upward from top surface 326 of each outer portion 324. Teeth 328 extend inward generally toward central portion 318 and are sized and shaped to correspond to teeth 244 (shown in FIGS. 20-22) of lock nut 206. In the exemplary embodiment, teeth 328 are configured to facilitate preventing counter-clockwise rotation of lock nut 206. Alternatively, teeth 328 are configured to facilitate preventing rotation of lock nut 206 in the clockwise direction, or both the counter-clockwise and the clockwise directions.

In the exemplary embodiment, lock washer 304 is fabricated from a metal, for example, and without limitation, steel, aluminum, titanium, or a superalloy. Alternatively, lock washer 304 is fabricated from any material that enables fastener assembly 300 to function as described herein, such as, without limitation, composite materials, resins, fiber reinforced resins, plastics, and fiber reinforced plastics.

Figure 30:
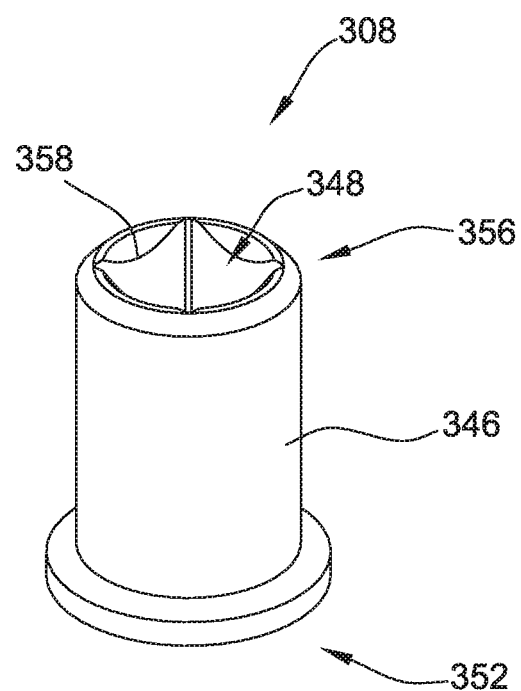
FIG. 30 is an upper perspective view of a tool for use with the fastener assembly of FIG. 25.
Figure 31:
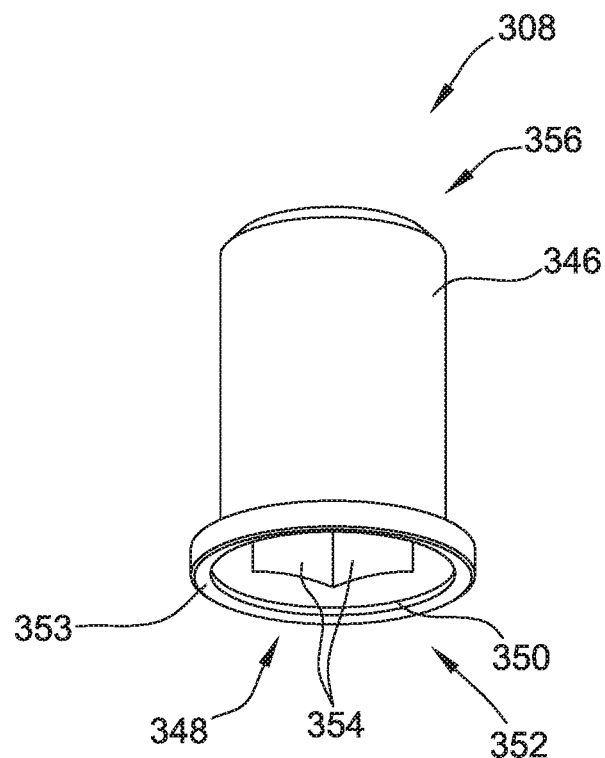
FIG. 31 is a lower perspective view of the tool of FIG. 30.
Figure 32:
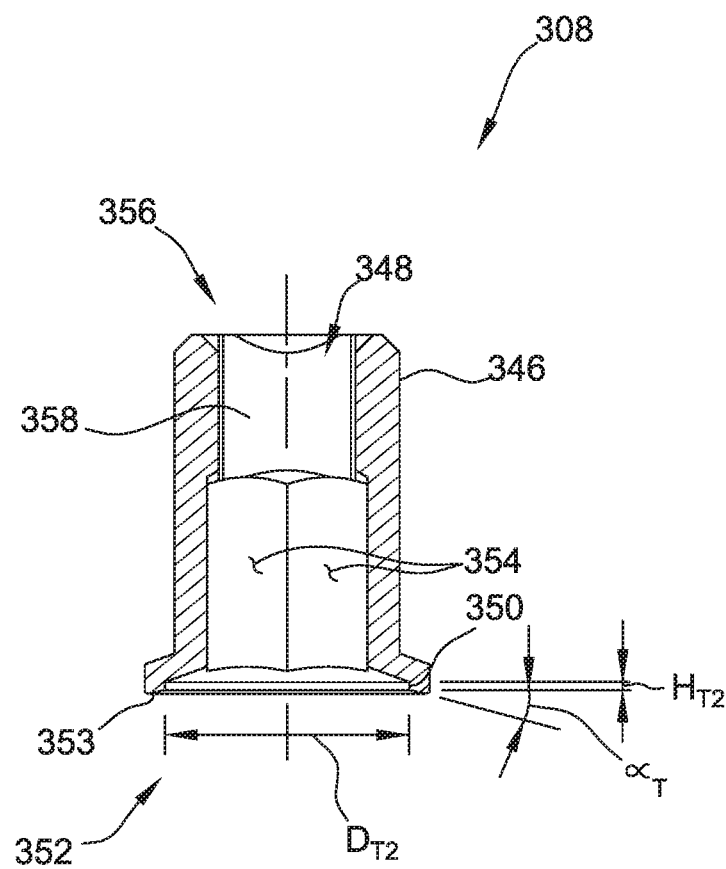
FIG. 32 is a sectional view of the tool of FIG. 30.

With reference to FIG. 26, tool 308 is configured for engaging both lock nut 206 and lock washer 304 to facilitate installation and removal of lock nut 206 from fastener assembly 300. With reference to FIGS. 30-32, in the exemplary embodiment, tool 308 includes a body 346 having a stepped bore 348 extending axially therethrough. Stepped bore 348 includes a cylindrical portion 350 at a first end 352 of body 346. Cylindrical portion 350 has a diameter "$D_{t2}$" configured to receive flange 232 of lock nut 206 therein. In particular, diameter "$D_{t2}$" is greater than diameter "$OD_{n2}$" of the outer extent of teeth 244 of flange 232 to enable lock nut 206 to slide freely into tool 308 in an axial direction. Cylindrical portion 350 extends axially along stepped bore 348 a predetermined distance "$H_t$" configured to facilitate receiving the entirety of lock nut 206 in stepped bore 348 such that body 346 engages outer portions 324 of lock washer 304, as is described herein. A sloped engaging surface 353 extends radially outward from a lower edge of cylindrical portion 350 to first end 352 of body 346. In the exemplary embodiment, sloped engaging surface 353 is sloped at an angle "$\alpha_t$" with respect to a plane coincident with first end 352. Sloped engaging surface 353 is configured to engage outer portions 324, and in particular, teeth 328 of lock washer 304, thereby deflecting outer portions 324 downward into face-to-face contact to facilitate disengaging lock washer 304 from lock nut 206.

Stepped bore 348 also includes wrenching surfaces 354 extending from cylindrical portion 350 toward a second end 356 of body 346. At second end 356, stepped bore 348 includes a driver connection 358 for receiving driving torque from a driving member (not shown). Wrenching surfaces 354 correspond in shape and size, and are configured, to engage body 230 of lock nut 206. In the exemplary embodiment, driver connection 358 is a square-shaped bore. Alternatively, driver connection 358 has any shape that enables tool 308 to function as described herein.

Figure 33:
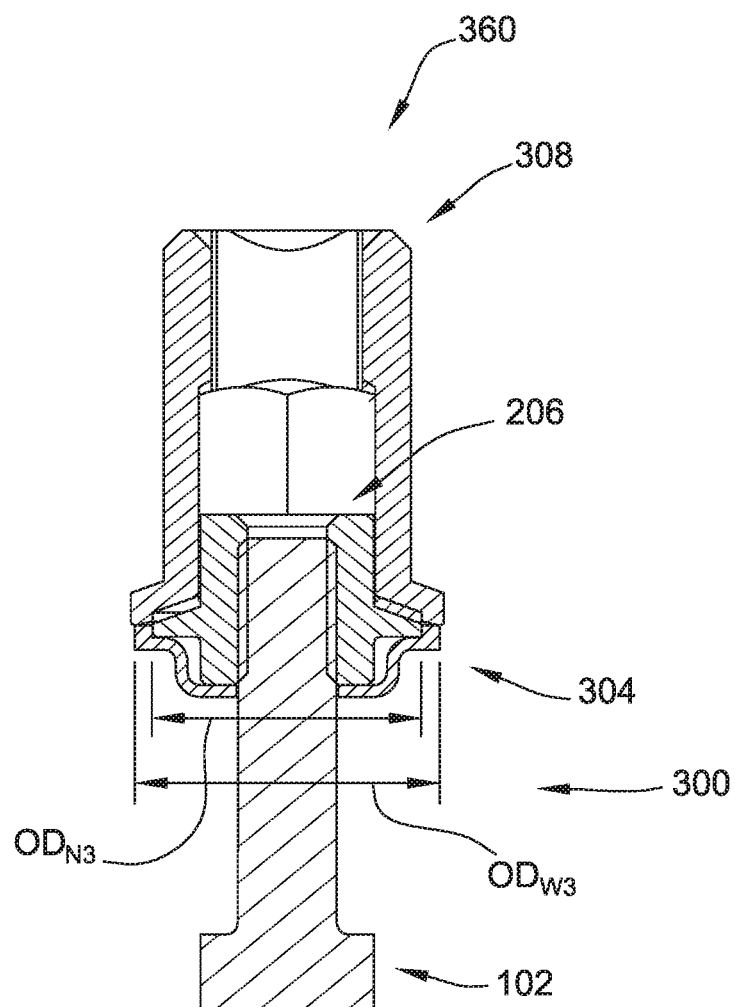
FIG. 33 is a sectional view of the fastener assembly of FIG. 25, showing the lock washer in a first orientation.
Figure 34:
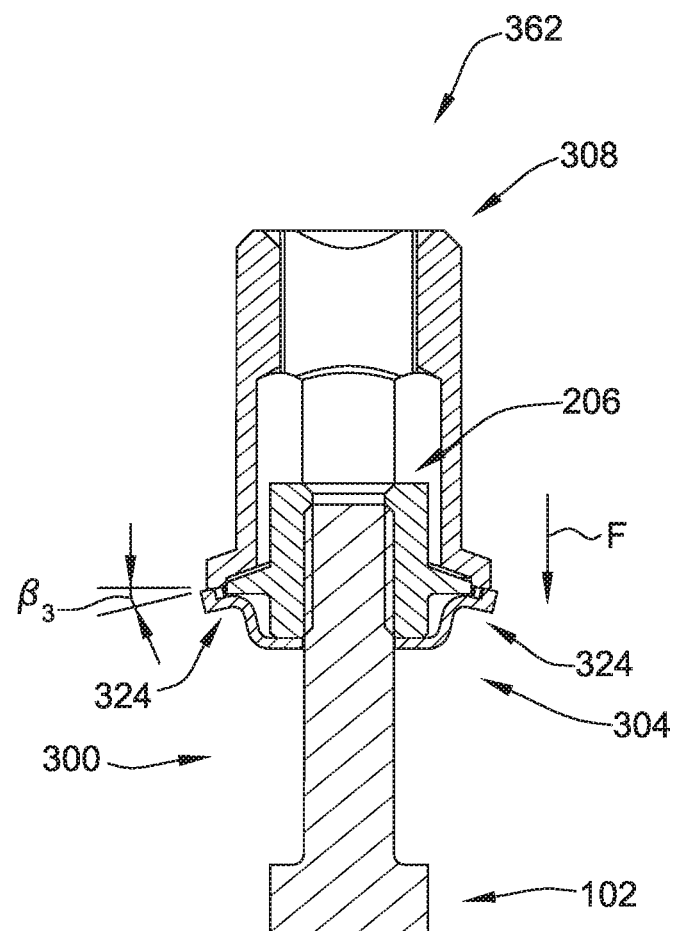
FIG. 34 is a sectional view of the fastener assembly of FIG. 25, showing the lock washer in a second orientation.

FIG. 33 is a sectional view of fastener assembly 300 showing lock washer 304 in a first orientation 360, where lock nut 206 is engaged with lock washer 304 and rotationally fixed. FIG. 34 is a sectional view of fastener assembly 300 showing lock washer 304 in a second orientation 362, where tool 308 is engaged with outer portions 324 of lock washer 304. In the exemplary embodiment, lock washer 304 is movable between first orientation 360 and second orientation 362. In first orientation 360, teeth 244 formed in flange 232 of lock nut 206 engage (i.e., mesh with) locking teeth 328 formed on outer portions 324 of lock washer 304. Engaging teeth 244 with locking teeth 328 facilitates rotationally fixing lock nut 206 relative to lock washer 304. In addition, lock washer 304 is rotationally fixed to threaded member 102 via the engagement of anti-rotation structures 322 to the pair of opposing longitudinally extending anti-rotation features 114 of threaded body portion 112 of threaded member 102. Accordingly, lock nut 206 is rotationally fixed relative to threaded member 102 in first orientation 360 of fastener assembly 300.

In the exemplary embodiment, "$OD_{w3}$" is greater than "$OD_{n2}$" such that tool 308 facilitates providing an axial force "F" to outer portions 324. More specifically, sloped engaging surface 353 of tool 308 at first end 352 engages the respective locking teeth 328 of outer portions 324 such that apply a force "F" facilitates bending or flexing outer portions 324 from first orientation 360 to second orientation 362. Second orientation 362 is offset from first position 360 by an angle "$\beta_3$" of sufficient magnitude to facilitate disengaging locking teeth 328 from teeth 244 of lock nut 206, thereby facilitating lock nut 206 to freely rotate relative to lock washer 304 and threaded member 102.

Figure 35:
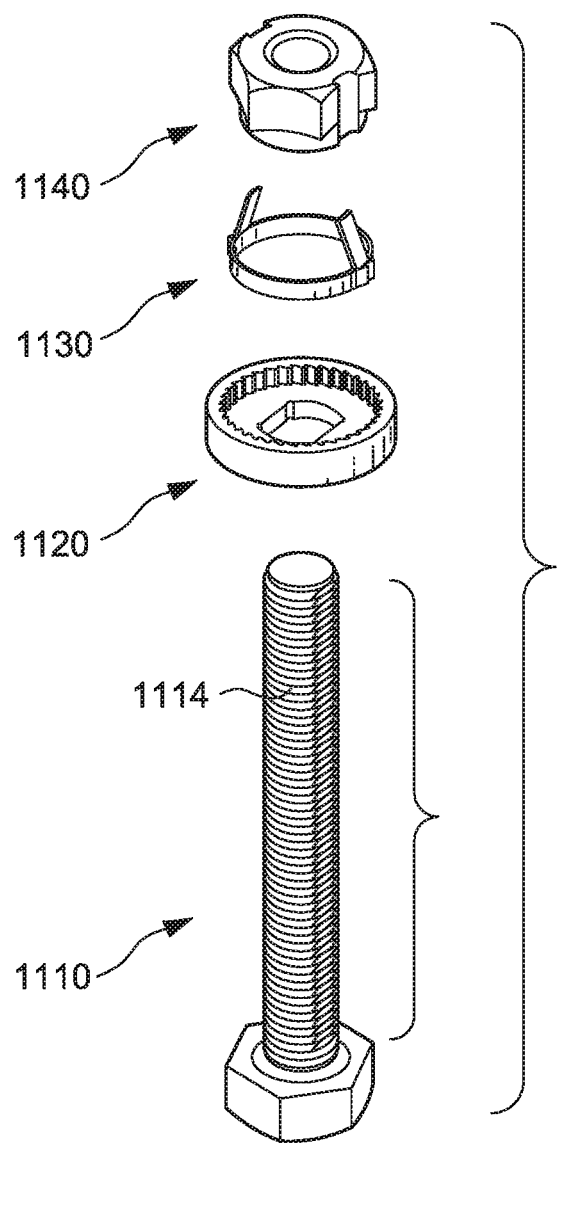
FIG. 35 is an exploded perspective view of another exemplary embodiment of a fastener device, showing a nut member, a lock member, a washer member, and a bolt member of the fastener device.

FIG. 35 shows a fastener with a locking mechanism constructed in accordance with the present disclosure designated generally by reference numeral 1000. Fastener device 1100 generally includes an elongated bolt member 1110, a washer member 1120, a lock member 1130, and a nut member 1140. Bolt member 1110 has a threaded segment 1114. Threaded segment 1114 includes male threads corresponding to female threads disposed on nut member 1140. One or more of bolt member 1110, washer member 1120, lock member 1130, and nut member 1140 may include plastic, metal, a combination thereof, or any other suitable material.

Figure 36:
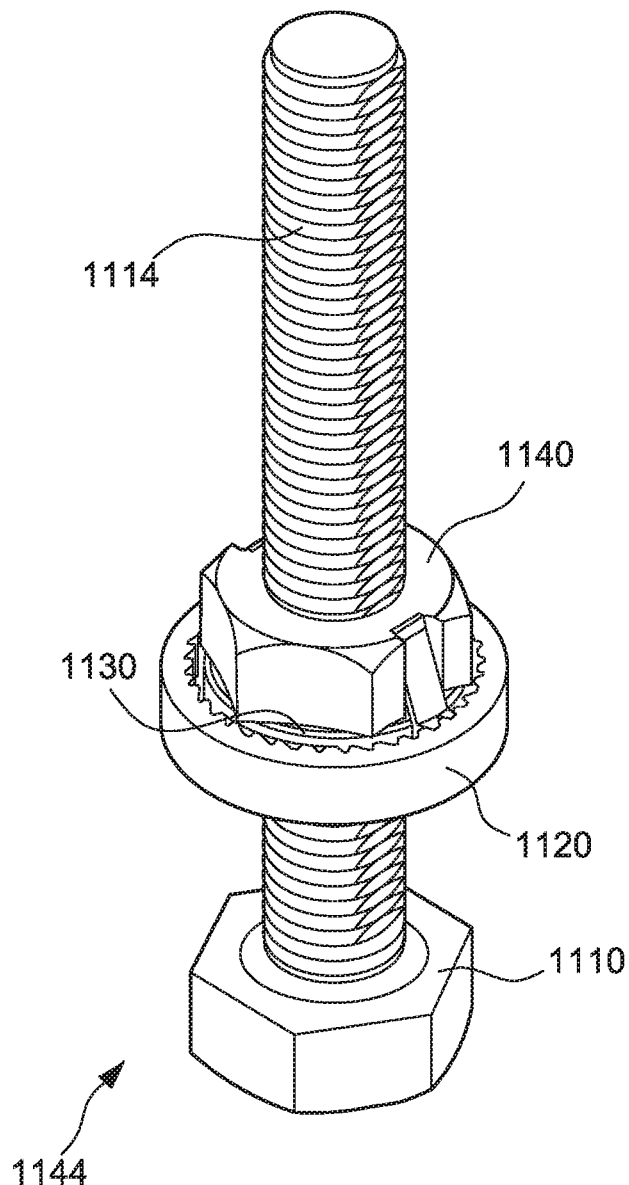
FIG. 36 is a perspective view of the fastener device of FIG. 35, showing the fastener device in an assembled configuration.

With reference to FIG. 36, washer member 1120 seats about threaded segment 1114 such that washer member 1120 is rotatably fixed and axially displaceable relative to bolt member 1110. Lock member 1130 seats about threaded segment 1114 of bolt member 1110 and against an axial face of washer member 1120. Nut member 1140 has female threads that thread engage male threads on threaded segment 1114, and is disposed axially along bolt member 1110 such that nut member 1140 seats against washer member 1120. Lock member 1130 seats about threaded segment 1114 and is axially interposed between washer member 1120 and nut member 1140.

Figure 37:
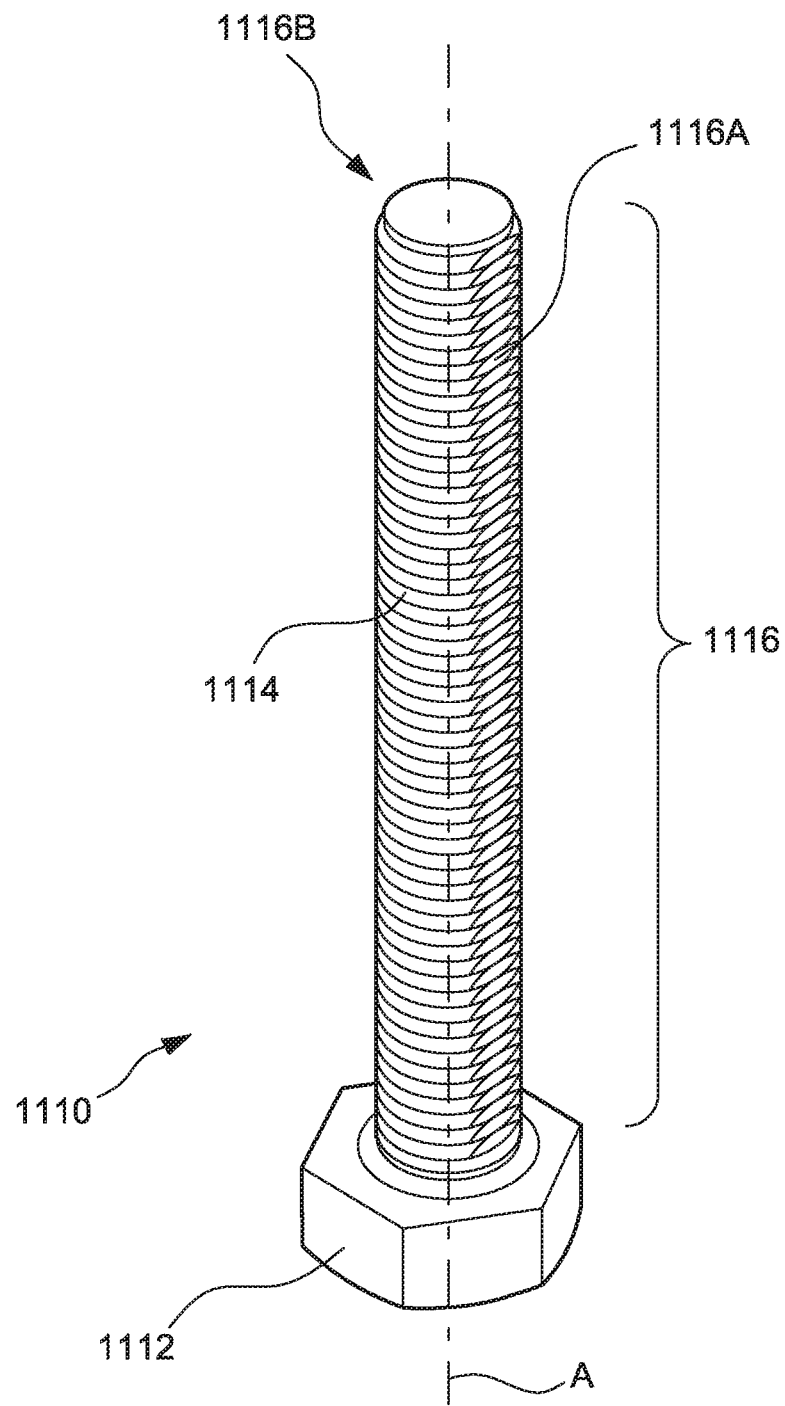
FIG. 37 is a perspective view of the bolt member of FIG. 35, showing the elongated body, threaded segment, and banking feature of the bolt member.

With reference to FIG. 37, an exemplary bolt member 1110 is shown. Bolt member 1110 defines a fastener axis "A" and, in the illustrated embodiment, includes a head portion 1111 disposed on an end opposite threaded segment 1114. Threaded segment 1114 has a banking feature 1116 that, in the illustrated embodiment, includes a first longitudinally extending flat 1116A and an opposed second longitudinally extending flat 1116B. It is to be understood and appreciated that other banking feature geometries are possible within the scope of the present disclosure such as a single flat portion, notches, grooves, convex portions, concave portions, protrusions, slots, and/or combinations thereof. Examples of such features are shown and described in U.S. Patent Application Publication No. 2014/0308089 A1, the contents of which are incorporated by reference herein in their entirely.

Figure 38:
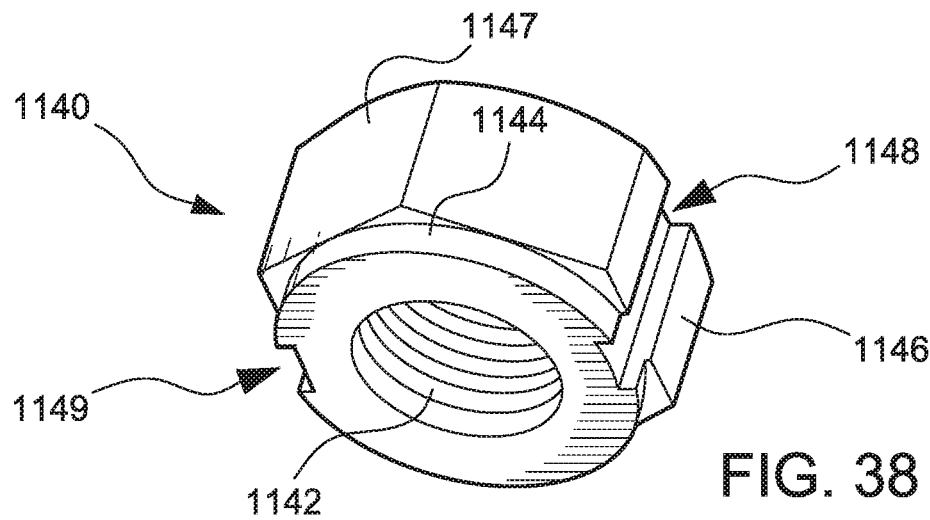
FIG. 38 is a perspective view of the nut member of FIG. 35, showing the threaded bore, annular recess, hexagonal recess, and an exemplary axial slot of the nut member.

With reference to FIG. 38, nut member 1140 is shown. Nut member 1140 includes a bore 1142 having female threads, an annular recess 1144, one or more slotted circumferential face 1146, and one or more continuous face 1147. Bore 1142 extends between axially opposed faces of nut member 1140. Annular recess 1144 extends circumferentially about bore 1142 and adjacent to the tool engagement faces of nut member 1140. The one or more slotted circumferential face 1146 and one or more continuous face 1147 define tool engagement faces that extend axially between annular recess 1144 and an axial face of nut member 1140 that is opposite annular recess 1144 and circumferentially about nut member 1140. The tool engagement faces may correspond to one or more common tools, such as a wrench or socket, and in the illustrated embodiment define a hexagonal circumference. This allows for tightening or loosening nut member 1140 using a standard hand tool and without requiring use of a specialized tool.

The one or more slotted circumferential face 1146 defines an axial slot 1148. Axial slot 1148 extends axially along slotted circumferential face 1146 between annular recess 1144 and the axial face of nut member 1140 opposite annular recess 1144, and has a circumferential width corresponding to the width of spring finger 1134 (shown in FIG. 39) and spring finger 1136 (shown in FIG. 39). This allows nut member 1140 to cooperate with the preload of spring finger 1134 such that, when axial slot 1148 aligns in rotation about fastener axis "A" (shown in FIG. 37), spring finger 1134 snaps into axial slot 1148. As will be appreciated by those of skill in the art in view of the present disclosure, snapping spring finger 1134 into axial slot 1148 fixes lock member 1130 in rotation relative to nut member 1140.

In the embodiment shown in FIG. 38, axial slot 1148 is a first axial slot and nut member 1140 includes a second axial slot 1149. Second axial slot 1149 is disposed on a diametrically opposed side of nut member 1140, i.e. on a side of axis "A" opposite first axial slot 1148, and on a slotted face that is substantially parallel to slotted circumferential face 1146. As will be appreciated by those of skill in the art in view of the present disclosure, nut member 1140 can have one, two, or more than two axial slots. The number of axial slots on nut member 1140 may correspond in number and circumferential position relative to those of lock member 1130. Although two axial slots are shown in the illustrated embodiment, it is to be understood and appreciated that nut member 1140 can have a single axial slot or more than two axial slots, as suitable for an intended application.

Figure 39:
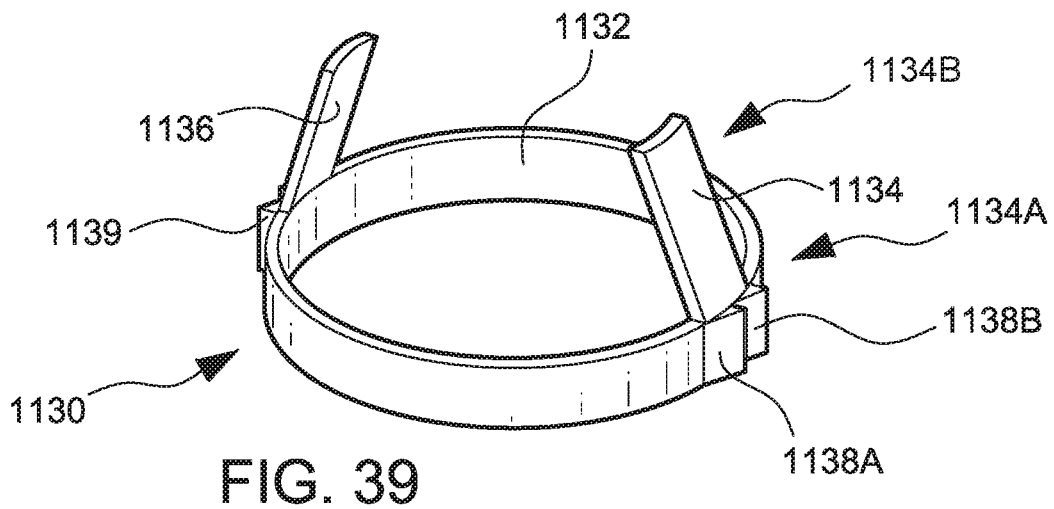
FIG. 39 is a perspective view of the lock member of FIG. 35, showing the deformable body, upstanding spring fingers, and teeth of the lock member.

With reference to FIG. 39, lock member 1130 is shown. Lock member 1130 includes a deformable annular body 1132. In the illustrated embodiment, annular body 1132 has a ring-like shape. It is contemplated that annular body 1132 may be round, oval, ellipsoid, or any other suitable shape, and may be constructed from a resilient material, such as an elastomer or spring steel. Response to a radial force exerted thereon by one or more spring fingers 1134, annular body 1132 may become more or less round depending upon the amount of radial force exerted on annular body 1132 and the spring constant of lock member 1130.

Spring finger 1134 upstands from annular body 1132 and extends between a fixed end 1134A and a free end 1134B. Fixed end 1134A connects to annular body 1132. Spring finger 1134 extends radially inward from fixed end 1134A such that free end 1134B is disposed radially inward of fixed end 1134A. In the illustrated embodiment, spring finger 1134 is a first spring finger and lock member 1130 includes a second spring finger 1136. Second spring finger 1136 is similar to first spring finger 1134, and is additionally connected to annular body 1132 such that second spring finger 1136 faces first spring finger 1134 on a side of lock member 1130 that is diametrically opposed to the first spring finger 1134.

A tooth 1138 is disposed on the radially outer surface of lock member 1130 and is circumferentially aligned relative to spring finger 1134. Tooth 1138 includes a locking surface 1138B and a sliding face 1138A that correspond to the locking surfaces and sliding faces of washer member 1120 (shown in FIG. 38). This allows a tool, e.g. tool 1010 (shown in FIG. 42), to slidably engage spring finger 1134, thereby radially displacing tooth 1138 relative to the engagement teeth 1126 of washer member 1120. In the illustrated embodiment, tooth 1138 is one of a plurality of teeth, and a second tooth 1139 is disposed on a diametrically opposite side of annular body 1132 circumferentially adjacent to second spring finger 1136. First tooth 1138 and/or second tooth 1139 can each be one of a plurality of circumferentially adjacent teeth arranged about the radially outer surface of annular body 1132 for fixing lock member 1130 in rotation relative to washer member 1120 (shown in FIG. 40).

Figure 40:
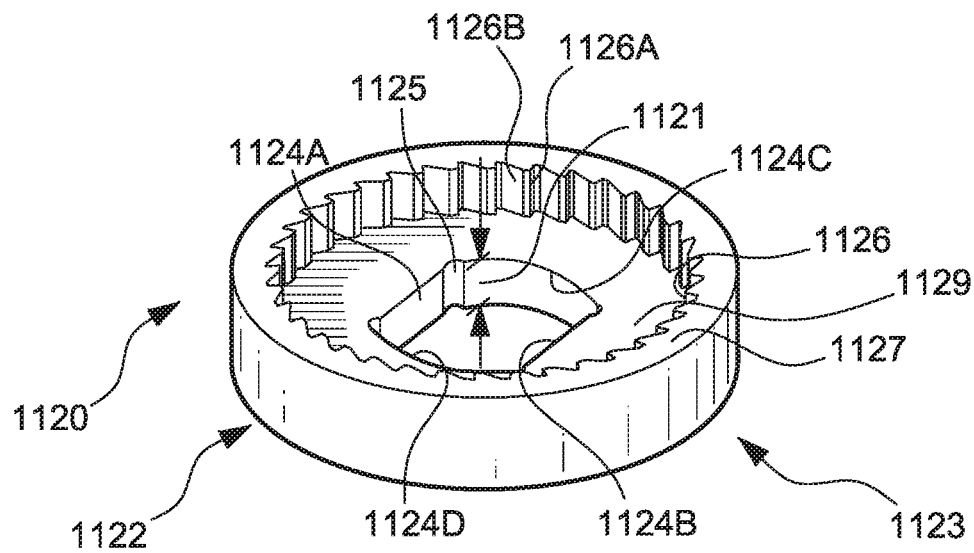
FIG. 40 is a perspective view of the washer member of FIG. 35, showing the washer member central aperture and banking portion, circumferential lip, and radial teeth oriented radially inwards relative to the circumferential lip.

With reference to FIG. 40, washer member 1120 is shown. Washer member 1120 has a central bore 1121 that extends between a first axial face 1129 and an opposed second axial face 1123. First axial face 1129 is separated from second axial face 1123 by an axial thickness T of washer member 1120. Central bore 1121 is bounded by a plurality of banking segments that complement banking feature 1116 of bolt member 1110 (shown in FIG. 37). In the illustrated embodiment, the plurality of banking segments includes pair of flats coupled by a pair of arcuate segments and a plurality of stress reduction features. In this respect, central bore 1121 includes a first flat 1124A and a second flat 1124B that bound central bore 1121. A first arcuate segment 1124C extends between first flat 1124A and second flat 1124B. A second arcuate segment 1124D faces first arcuate segment 1124C and extends between opposite ends first flat 1124A and second flat 1124B. Stress reduction features 1125 are defined at corners of central bore 1121 where respective flats and arcuate segments intersect one another. It will be appreciated that other banking segments are contemplated within the scope of the present disclosure.

A circumferential wall 1127 extends axially from first axial face 1129 about the periphery of washer member 1120. Circumferential wall 1127 has a plurality of engagement teeth 1126. Engagement teeth 1126 are distributed about a radially inner face of circumferential wall 1127 and extend radially inward from circumferential wall 1127 and towards central bore 1121. In the illustrated embodiment, engagement teeth 1126 include a locking surface 1126A that is substantially orthogonal with respect to circumferential wall 1127 and a sliding face 1126B that is oblique relative to circumferential wall 1127.

Figure 41:
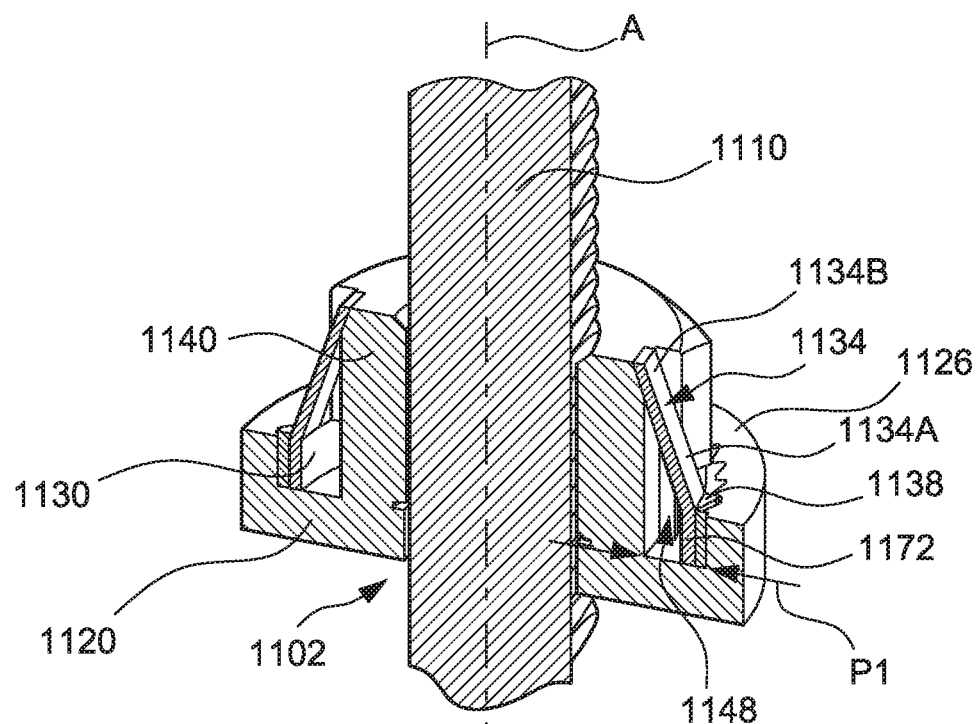
FIG. 41 is a sectional perspective view of a portion of the fastener of FIG. 35, showing the fastener and fastener locking mechanism in a locked position.
Figure 42:
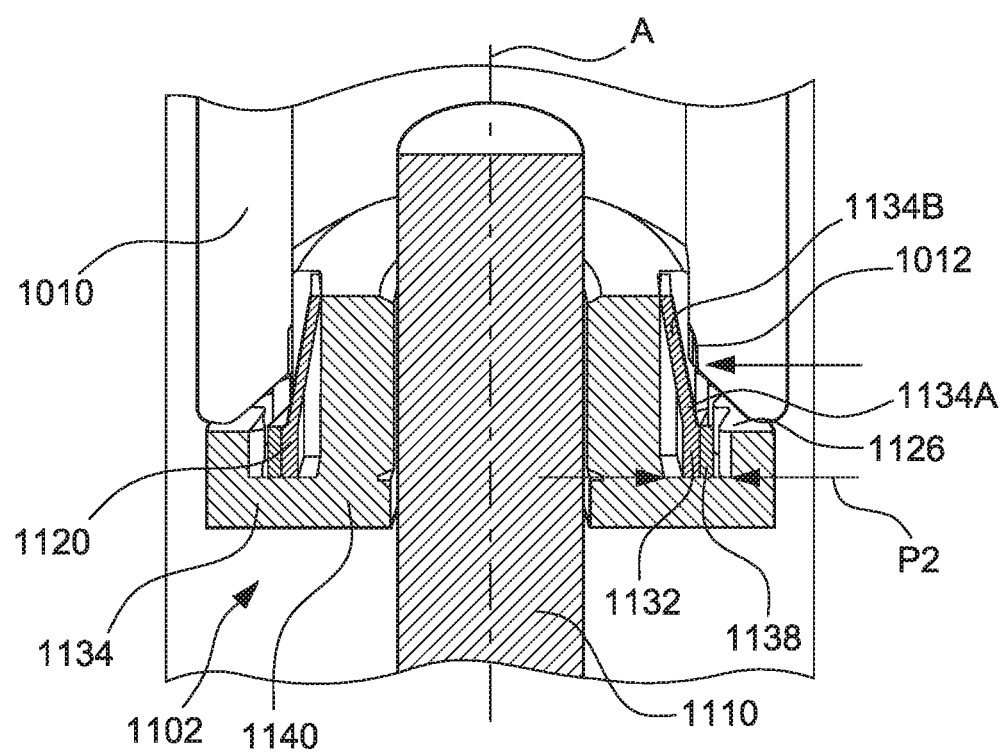
FIG. 42 is a sectional view of the fastener of FIG. 35, showing the fastener and fastener locking mechanism in a release or tighten position.

With reference to FIGS. 41 and 42, fastener 1100 is shown in an assembled configuration. FIG. 41 shows fastener 1100 with the locking mechanism 1102 in a locked position. FIG. 42 shows fastener 1100 with locking mechanism 1102 in a tighten or release position. In the locked position shown in FIG. 41, washer member 1120, lock member 1130, and nut member 1140 are each fixed both axially and in rotation relative to bolt member 1110. In the tighten or release position shown in FIG. 42, lock member 1130 and nut member 1140 are both rotationally free relative to bolt member 1110. As will be appreciated, rotation of nut member 1140 relative to bolt member 1110 displaces nut member 1140 axially relative to bolt member 1110, allowing corresponding axial displacement of washer member 1120 and lock member 1130 relative to bolt member 1110.

As indicated in FIG. 41, fixed end 1134A of spring finger 1134 assumes a locked position radial offset P1 when locking mechanism 1102 is in the locked position. At the locked position radial offset P1, deformable annular body 1132 is urged radially outward at the circumferential position corresponding to spring finger 1134. Urging annular body 1132 radially outward at the location corresponding to spring finger 1134 in turn urges tooth 1138 of lock member 1130 against engagement teeth 1126 of washer member 1120. Consequently, at circumferential arrangements where lock member tooth locking surface(s) 1138A align and overlap in a coplanar arrangement with a corresponding locking surface 1126A of engagement tooth 1126, lock member 1130 becomes rotational fixed relative to washer member 1120.

As also indicated in FIG. 41, free end 1134B of spring finger 1134 seats within axial slot 1148 when locking mechanism 1102 is in the locked position. Seating free end 1134B of spring finger 1134 in axial slot 1148 fixes lock member 1130 in rotation with nut member 1140. Fixing lock member 1130 in rotation relative to nut member 1140 causes lock member 1130 to rotate together with nut member 1140. Consequently, when tooth 1138 of lock member 1130 seats against engagement teeth 1126 of washer member 1120, lock member 1130 becomes fixed in rotation relative to washer member 1120. As will be appreciated, since washer member 1120 is fixed in rotation relative to both member the complementary banking member and banking portion of each, seating tooth 1138 of lock member 1130 against engagement tooth 1126 also fixes nut member 1140 in rotation relative to bolt member 1110.

With reference to FIG. 42, fastener 1100 is shown with locking mechanism 1102 in the tighten or release position. Locking mechanism 1102 moves from the locked position (shown in FIG. 41) to the illustrated tighten or release position by seating a tool over an end of fastener 1100. In this respect, tool 1010 includes a finger contact surface 1112 extending circumferentially about an interior recess of tool 1010. Upon seating tool 1010 over nut member 1140 by axially displacing tool 1010 relative to fastener 1100, contact surface 1112 comes into contact and exerts a contact force F on spring finger 1134, oriented obliquely relative thereto, at a location between fixed end 1134A and free end 1134B of spring finger 1134. Contact force F urges spring finger 1134 radially inward relative to fastener axis "A," deforming annular body 1132 such that fixed end 1134A of spring finger 1134 assumes an unlocked or tighten radial offset P2.

Unlocked or tighten radial offset P2 is smaller than locked radial offset P1. Moving fixed end 1134A of spring finger 1134 from locked radial offset P1 to unlocked or release radial offset P2 causes the locking surface 1138B of tooth 1138 to slide across locking surface of engagement tooth 1126. This disengages tooth 1138 of lock member 1130 from engagement tooth 1126 of washer member 1120, allowing lock member 1130 and nut member 1140 to rotate relative to washer member 1120 and bolt member 1110. As will be appreciated, tool 1010 may be rotated either clockwise or counterclockwise about fastener axis "A" to displace nut member 1140 axially in either direction along fastener axis "A", tightening nut member 1140 or loosening nut member 1140 as appropriate. Thus, when a tool such as a conventional socket wrench is applied to nut member 1140, lock member 1130 is deflected radially inward such that teeth of lock member 1130 disengage teeth of washer member 1120, thereby allowing rotation of lock member 1130 and nut member 1140 relative to washer member 1120 and bolt member 1110.

Figure 43:
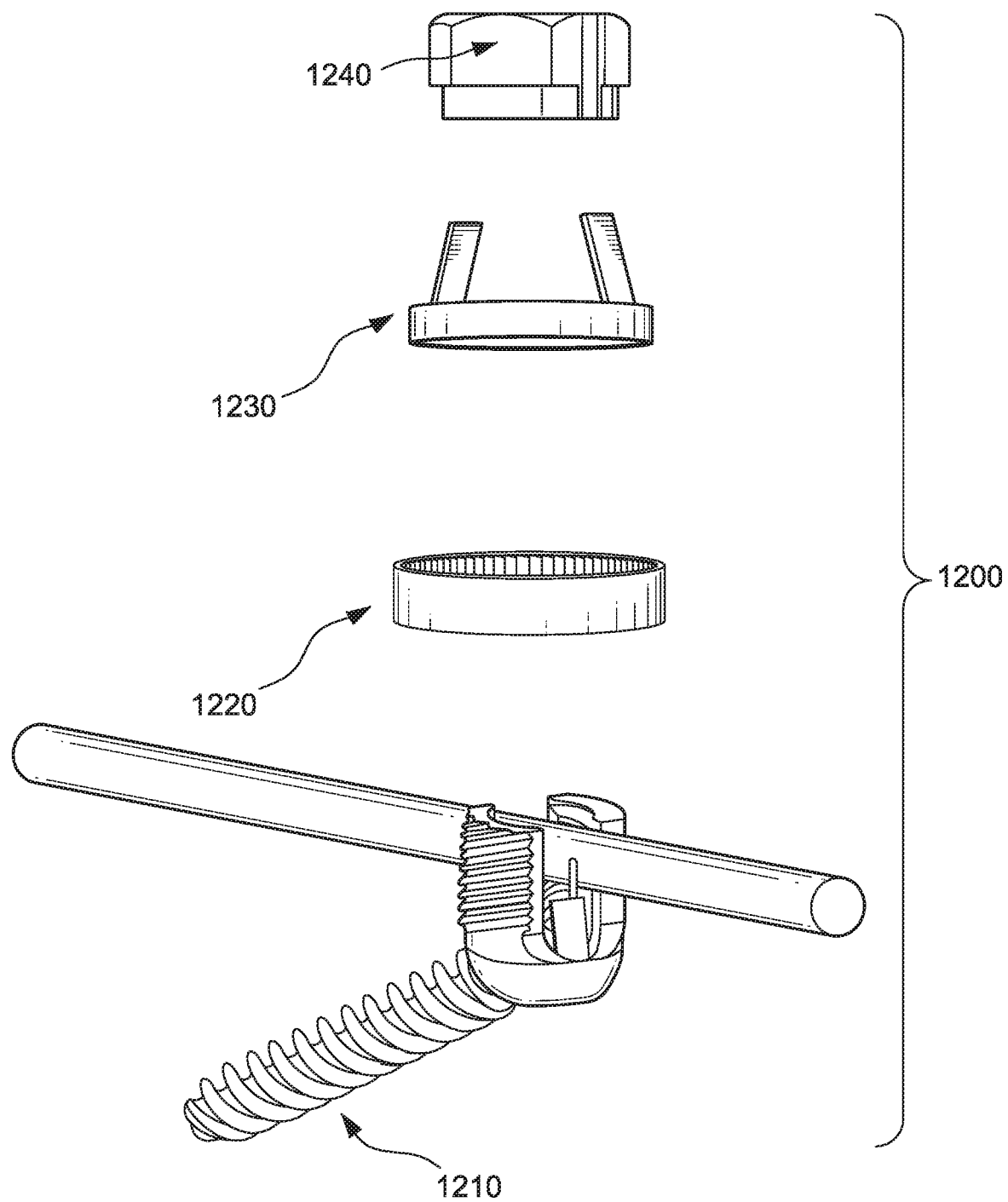
FIG. 43 is an exploded perspective view of another embodiment of a fastener device, showing a bone fixation system including a locking mechanism in accordance with the present disclosure.

Referring now to FIG. 43, another embodiment of a fastener with a locking mechanism constructed in accordance with the present disclosure is designated generally by reference numeral 1200. Fastener 1200 is similar to fastener 1100 and generally includes an elongated bolt member 1210, a washer member 1220, a lock member 1230, and a nut member 1240. Nut member 1240 is similar to nut member 1140 (shown in FIG. 40). Lock member 1230 is similar to lock member 1130 (shown in FIG. 39).

Figure 44:
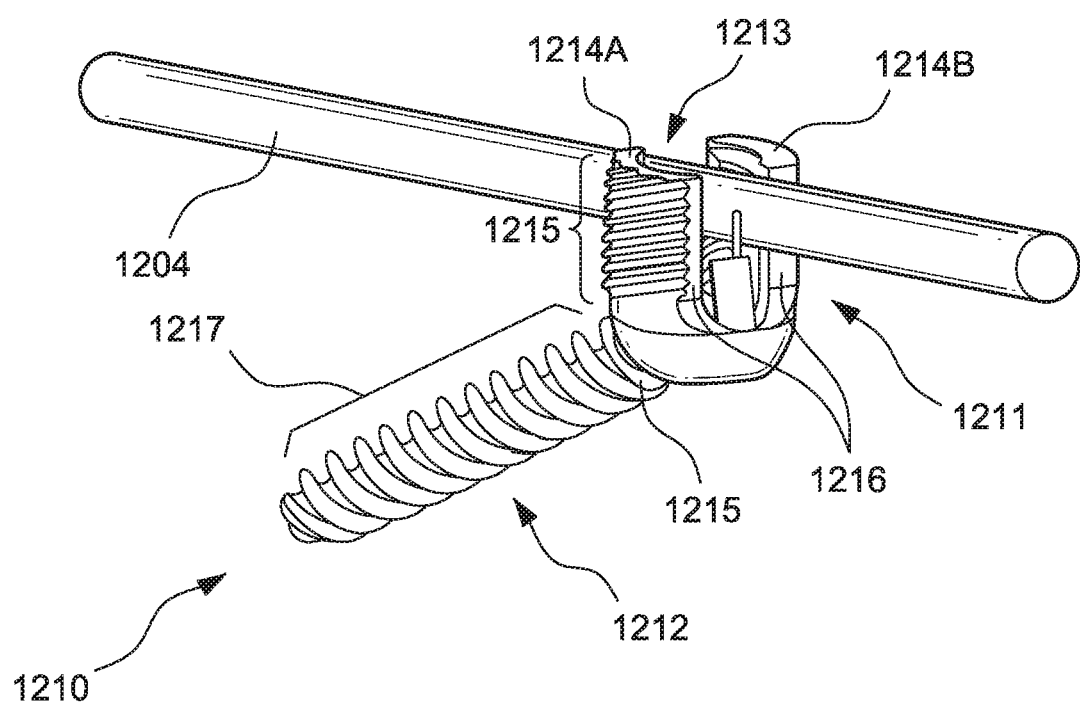
FIG. 44 is a perspective view of a bolt member of the fastener device show in FIG. 43, showing the bolt member stem and tulip head.

With reference to FIG. 44, bolt member 1210 is similar to bolt member 1110, and is additionally configured as fixation system for coupling a rod 1204 to bone, for example as a spinal pedicle screw rod system. Bolt member 1210 includes a tulip head 1211 and an elongated stem 1212. Elongated stem 1212 includes a second threaded segment 1217 that tapers from an end adjacent to tulip head 1211 to an end opposite tulip head 1211, thereby facilitating insertion of elongated stem 1212 into bone structure, such as a pedicle.

Tulip head 1211 includes a lateral slot 1213 with a first prong 1214A and an opposed second prong 1214B. Tulip head 1211 has a first threaded segment 1215 with a banking feature 1216. First threaded segment 1215 has male threads that correspond to female threads defined within the central bore of nut member 1240 (shown in FIG. 43). Banking feature 1216 complements the banking feature of washer member 1220 (shown in FIG. 45) such that washer member 1220 is rotatably fixed and axially displaceable relative to tulip head 1211. Banking feature 1216 is split by lateral slot 1213, thereby allowing for rod 1204 to seat therein and to extend therethrough, allowing for rod 1204 to be rotationally fixed and axially displaceable relative to tulip head 1211.

Figure 45:
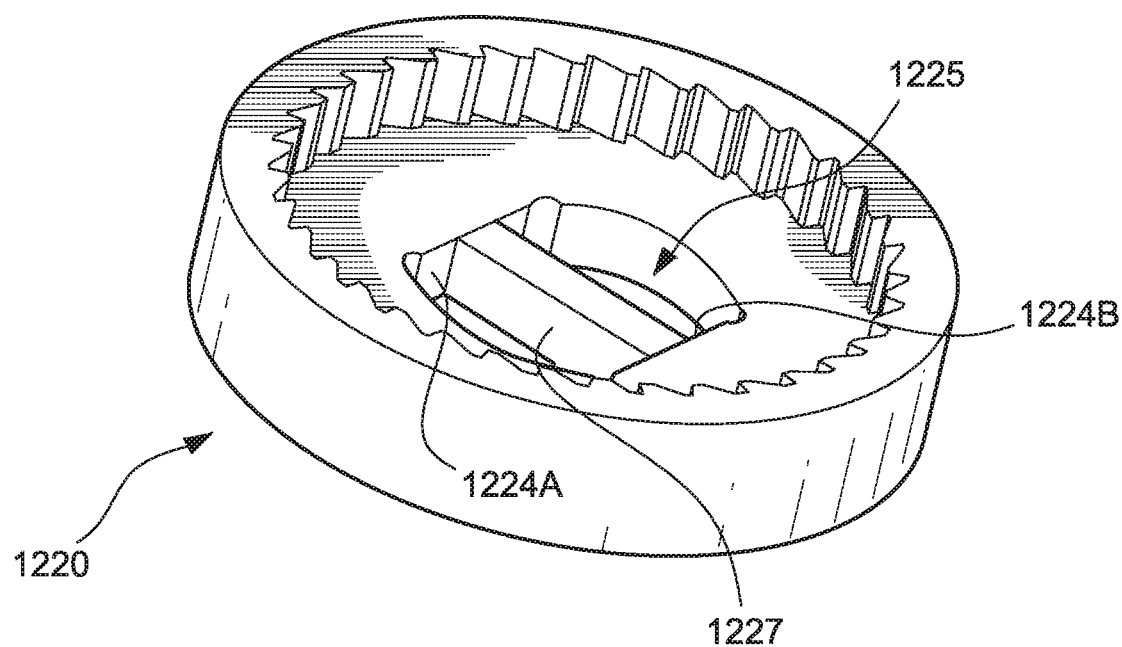
FIG. 45 is a perspective view of a washer member of the fastener device show in FIG. 43, showing the washer member central bar portion.

With reference now to FIG. 45, washer member 1220 is shown. Washer member 1220 is similar to washer member 1120 and additionally includes a central bar portion 1227. Central bar portion 1227 is disposed within washer member central aperture 1225 and extends between first inner surface 1224A and second inner surface 1224B of washer member banking portion 1224. In this respect central bar portion 1227 spans central aperture 1225, allowing transfer of force from nut member 1240 (shown in FIG. 43) in a force flow path including central bar portion 1227 to rod 1204 (shown in FIG. 44). As will be appreciated, central bar portion 1227 extends between opposing sides of lateral slot 1213 to create two discrete axial apertures on diametrically opposed flats of the tulip head banking feature.

Referring to FIGS. 43-45, the flats on first prong 1214A (shown in FIG. 44) and second prong 1214B are configured to mate with respective first flat inner surface 1224A or second inner surface 1224B of washer member 1220. This rotationally fixes washer member 1220 relative to tulip head 1211 when first prong 1214A and second prong 1214B of tulip head 1211 are inserted into the discrete axial apertures bounded by central bar portion 1227. This allows axial movement of washer member 1220 along the prongs of tulip head 1211 to secure rod 1204 within lateral slot 1213 between washer member 1220, lock member 1230, and tulip head 1211. After rod 1204 is placed within lateral slot 1213, washer member 1220 is inserted over prongs of tulip head 1211, and central bar portion 1227 displaces axially downward within lateral slot 1213, in response to downward axial displacement of nut member 1240, to rest against rod 1204.

Those skilled in the art will readily appreciate that because nut member 1240 and washer member 1220 are substantially similar to nut member 1140 and washer member 1120, a common tool such as a wrench or socket can be used to tighten rod 1204 to the fastener 1100 or remove rod 1204 from fastener 1100 by either rotating nut member 1240 clockwise or counterclockwise. Traditional bone fixation systems tend to require a significant amount of torque in order to lock a rod to a fastener or to remove the rod from the fastener. This can be the case, for example, in conventional external bone fixation systems and/or internal bone fixation systems like spinal pedicle screw rod systems. Those skilled in the art will readily appreciate, however, that embodiments of the present disclosure reduce the amount of torque required as compared with traditional spinal pedicle screw rod systems.

Figure 46:
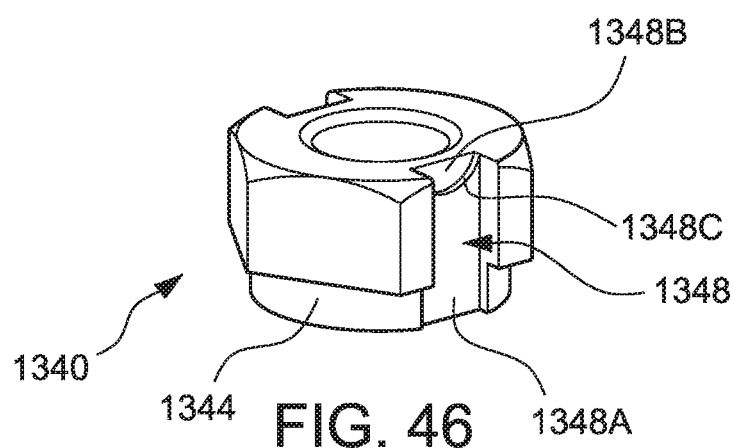
FIG. 46 is a perspective view of a nut member for use with the fastener devices shown in FIGS. 35 and 43.
Figure 47:
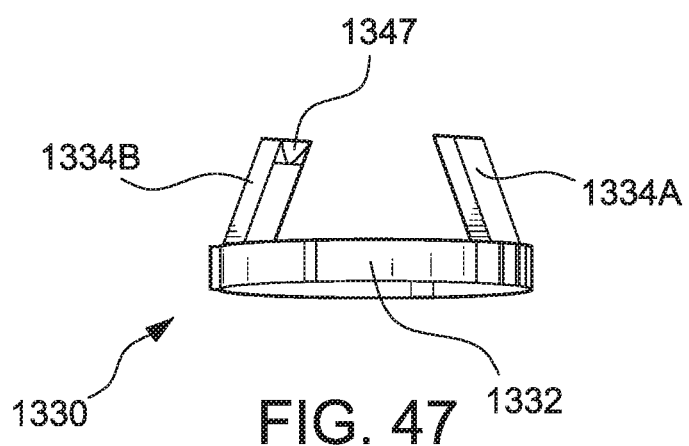
FIG. 47 is a perspective view of a lock member for use with the fastener devices shown in FIGS. 35 and 43.
Figure 48:
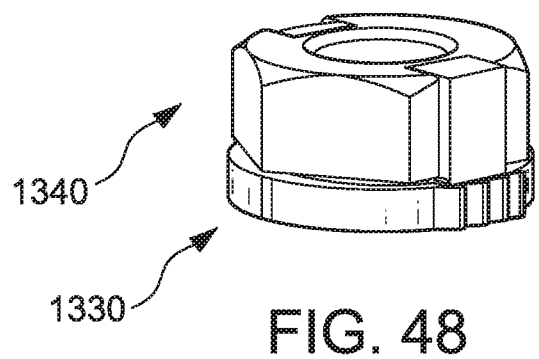
FIG. 48 is a perspective view of the lock member shown in FIG. 47 coupled to the nut member shown in FIG. 46, showing spring member protrusions and corresponding protrusion sockets defined within the nut member axial slots.

With reference to FIGS. 46-48, a nut member 1340 and a lock member 1330 are shown according to another embodiment. Referring to FIG. 46, nut member 1340 is shown. Nut member 1340 is similar to nut member 1140 (shown in FIG. 40) and additionally includes a stepped axial slot 1348. Stepped axial slot 1348 has a first step 1348A and a second step 1348B. First step 1348A traverses annular groove 1344 and extends axially to second step 1348B. Second step 1348B is disposed radially inward of first step 1348A. An arcuate riser 1348C extends radially outward and faces axially.

Referring to FIG. 47, lock member 1330 is shown. Lock member 1330 is similar to lock member 1130 (shown in FIG. 39) and additionally includes a stiffened deformable annular body 1332, a stiffened first spring finger 1334A, and a stiffened second spring finger 1334B. As used herein, stiffened means that deforming annular body 1332, first spring finger 1334A, and/or second spring finger 1334B requires more force than annular body 1132, first spring finger 1134, and/or second spring finger 1136 (each shown in FIG. 39). This may be accomplished, for example, by thickening the respective elements relative to the counterpart elements shown in the embodiment illustrated in FIG. 39.

First spring finger 1334A and second spring finger 1334B both include a protrusion 1347 (only one indicated in FIG. 47 for clarity reasons). Protrusion 1347 corresponds to second step 1348B of stepped axial slot 1348 (shown in FIG. 46), and in illustrated embodiment has an arcuate lip contoured to complement arcuate riser 1348C (shown in FIG. 46) such that arcuate riser 1348C seats in second step 1348B (shown in FIG. 46). This allows for lock member 1330 to seat against nut member 1340 and remain in an assembled configuration (shown in FIG. 48) prior to installation on a bolt member, simplifying fastening elements and error proofing the installation process.

Figure 49:
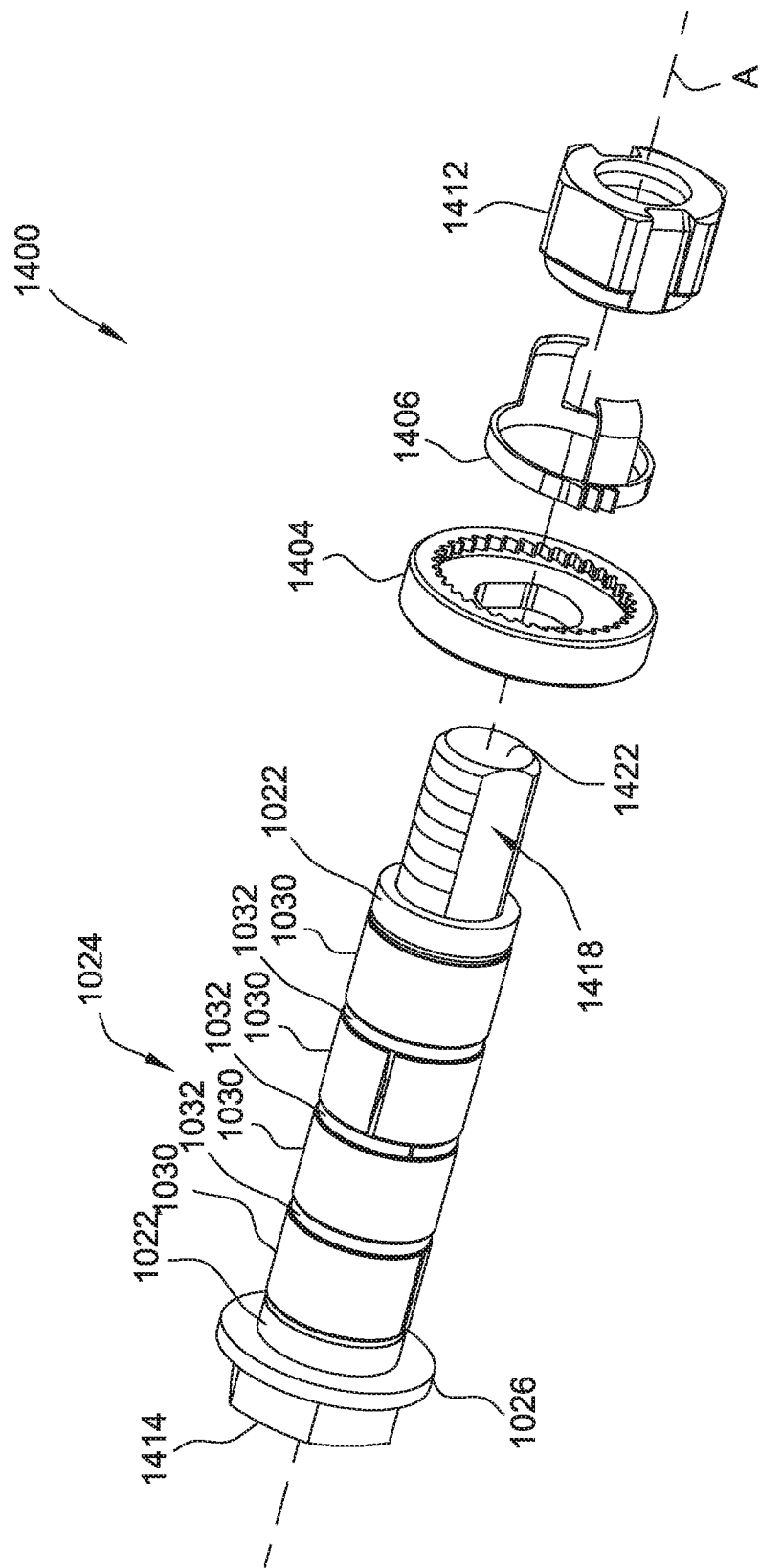
FIG. 49 is an exploded perspective view of an adjustable diameter fastener assembly.
Figure 50:
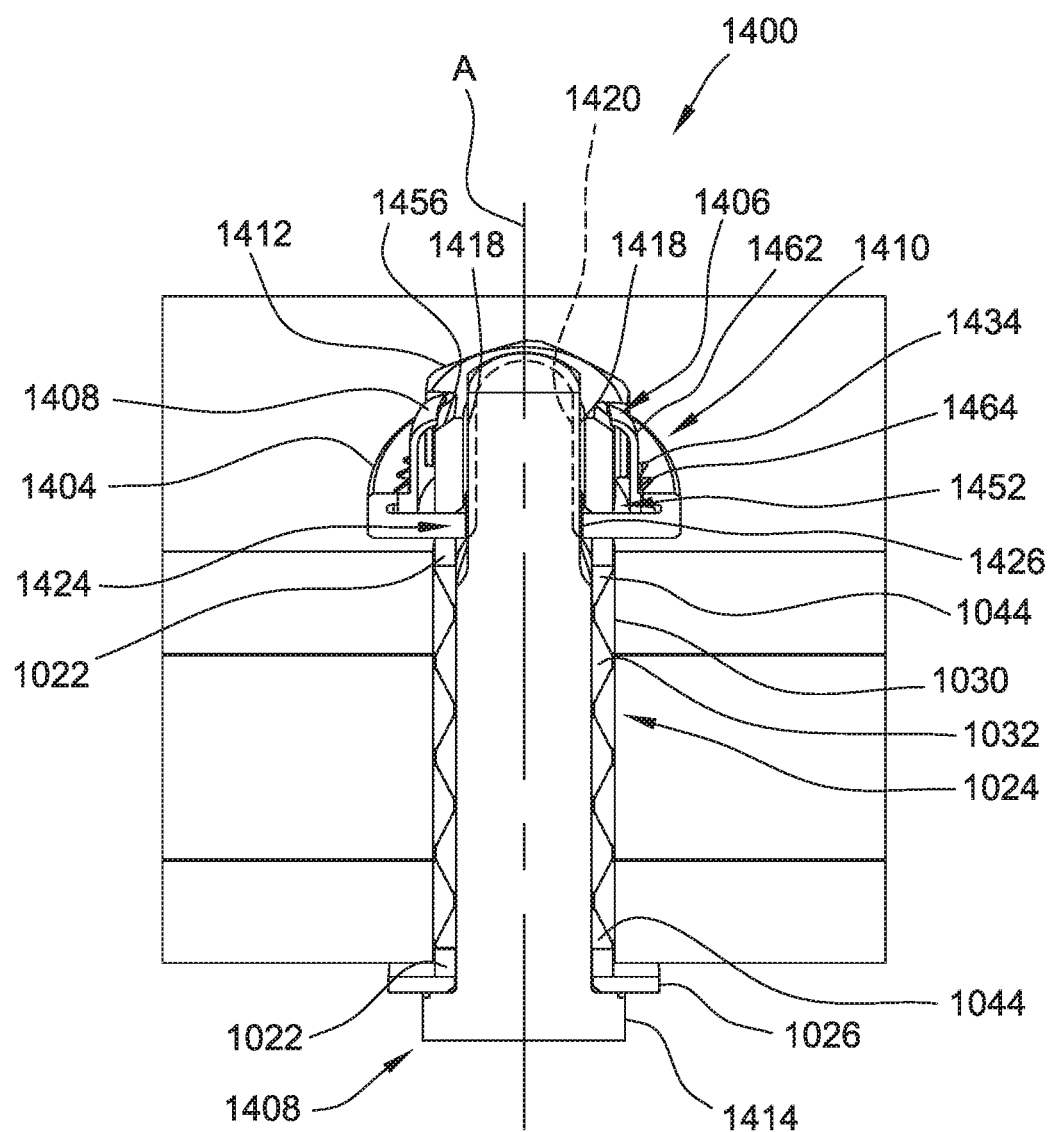
FIG. 50 is a sectional perspective view of the adjustable diameter fastener assembly shown in FIG. 49 in a first orientation, including a lock washer engaged with a lock member and rotationally fixed with respect to a threaded member.
Figure 51:
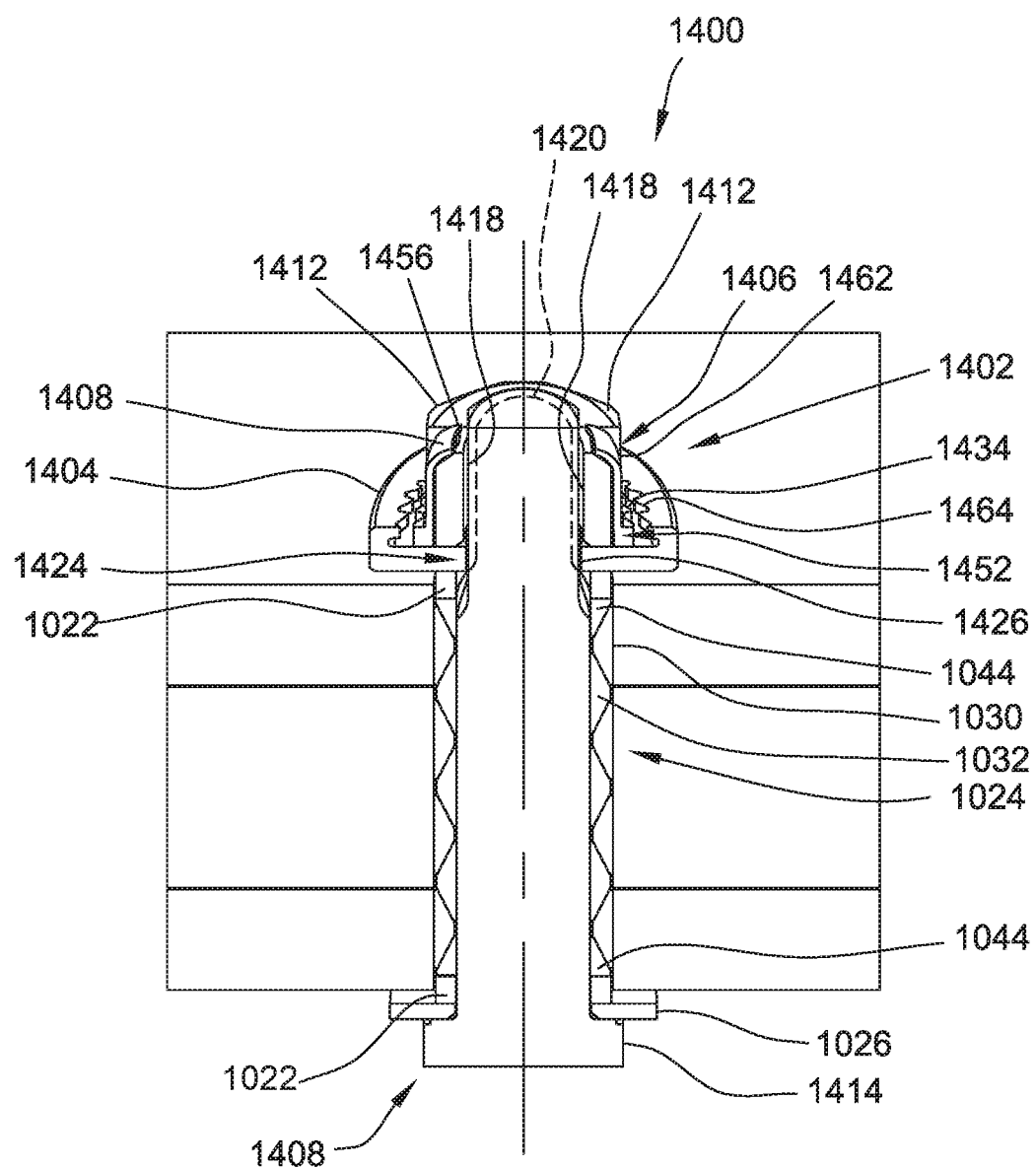
FIG. 51 is a sectional perspective view of the adjustable diameter fastener assembly shown in FIG. 49 in a second orientation, including the lock member disengaged from the lock washer.

FIG. 49 is an exploded perspective view of an adjustable diameter fastener assembly 1400. FIG. 50 is a sectional perspective view of adjustable diameter fastener assembly 1400 in a first orientation 1402, showing a lock washer 1404 engaged with a lock member 1406 and rotationally fixed with respect to a threaded member 1408. FIG. 51 is a sectional perspective view of adjustable diameter fastener assembly 1400 in a second orientation 1410, showing lock member 1406 disengaged from lock washer 1404. In the exemplary embodiment, adjustable diameter fastener assembly 1400 is an adjustable bushing fastener that operates by radial expansion of a radially expandable bushing 1024. Alternatively, adjustable diameter fastener assembly 1400 is any type of adjustable diameter fastener assembly, for example, and without limitation, a compression or clamp-up type fastener assembly.

In the exemplary embodiment, radially adjustable bushing 1024 is positioned about threaded member 1408, between a thrust ring 1022 adjacent a head portion 1414 and a thrust ring 1022 proximate a threaded portion 1420 of threaded member 1408. A thrust washer 1026 is positioned between head portion 1414 and thrust ring 1022. Bushing 1024 includes a plurality of inner rings 1032 positioned between outer rings 1030. As is known in the art, inner rings 1032 have opposed conical wedge surfaces. Outer rings 1030 have an exterior cylindrical surface and interior opposed conical wedge surfaces that correspond to the conical wedge surfaces of inner rings 1032. Outer rings 1030 engage inner rings 1032 at opposite ends thereof. Inner rings 1032 and outer rings 1030 are each split by a slot that extends through a wall of each ring, where the slot extends axially with respect to the rings. The axial ends of bushing 1024 are formed by half segments 1044 of inner rings 1032 to facilitate providing flat end of bushing 1024. Alternatively, the ends of bushing 1024 can be formed by half segments of outer rings 1030, or one end of bushing 1024 can be formed by a half segment of inner ring 1032 and the other end by a half segment of outer ring 1030. It should be appreciated that the geometry of conical wedge surfaces of outer rings 1030 and inner rings 1032 can be varied, including a cross-sectional shape. Varying the cross-sectional shapes of outer rings 1030 and inner rings 1032 facilitates configuring outer rings 1030 and inner rings 1032 to expand in a predetermined manner, for example, and without limitation, having inner rings 1032 expand more and/or sooner than outer rings 1030.

Figure 52:
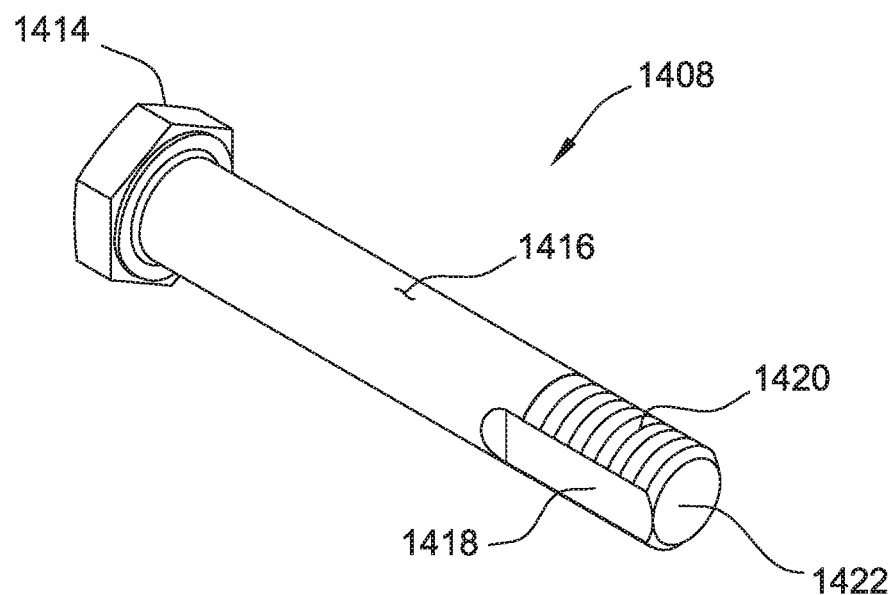
FIG. 52 is a perspective view of a threaded member of the adjustable diameter fastener assembly shown in FIG. 49.
Figure 53:
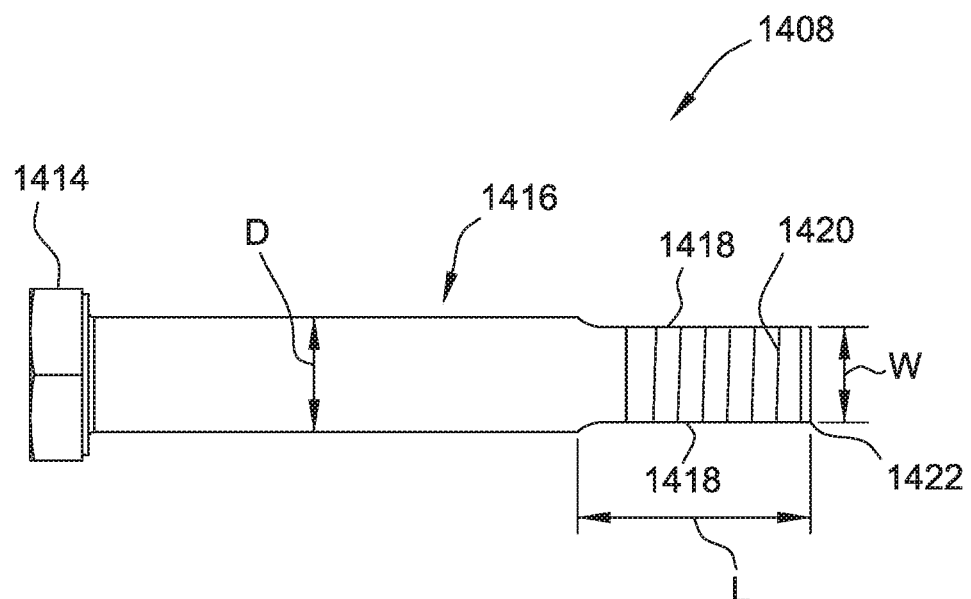
FIG. 53 is a side view of the threaded member shown in FIG. 52.

In the exemplary embodiment, adjustable diameter fastener assembly 1400 includes lock washer 1404, lock member 1406, threaded member 1408, and a lock nut 1412. FIG. 52 is a perspective view of threaded member 1408, and FIG. 53 is a side view of threaded member 1408. Threaded member 1408 includes head portion 1414, an elongated body portion 1416 extending axially from head portion 1414, and at least one anti-rotation feature 1418. Alternatively, threaded member 1408 may be free of head portion 1414. For example, and without limitation, threaded member 1408 may be a rod, a bolt, a screw, or any other threaded component that enables adjustable diameter fastener assembly 1400 to function as described herein.

In the exemplary embodiment, anti-rotation feature 1418 includes a pair of opposing longitudinally extending sections formed in a threaded portion 1420 of body portion 1416. It is contemplated that anti-rotation features 1418 include, for example, and without limitation, flats, notches, grooves, and/or any other feature that enables threaded member 1408 to function as described herein. Body portion 1416 has a diameter "D," defining a size of threaded member 1408. In the exemplary embodiment, anti-rotation features 1418 include a pair of flat portions that are parallel to each other and are spaced apart a width "W," which is smaller than diameter "D." Anti-rotation features 1418 are substantially equal in size and shape, and extend along threaded portion 1420 of body portion 1416 from an end 1422 of threaded member 1408 a predefined length "L." It is contemplated that anti-rotation features 1418 can extend any length "L" along body portion 1416, up to and including extend to head portion 1414. In the exemplary embodiment, as shown in FIG. 52, head portion 1414 is a hexagonal head. Alternatively, head portion 1414 is any shape or form, for example, and without limitation, a spline head, a flat head, a socket cap head, a tulip head, and a pan head, that enables adjustable diameter fastener assembly 1400 to function as described herein.

Figure 54:
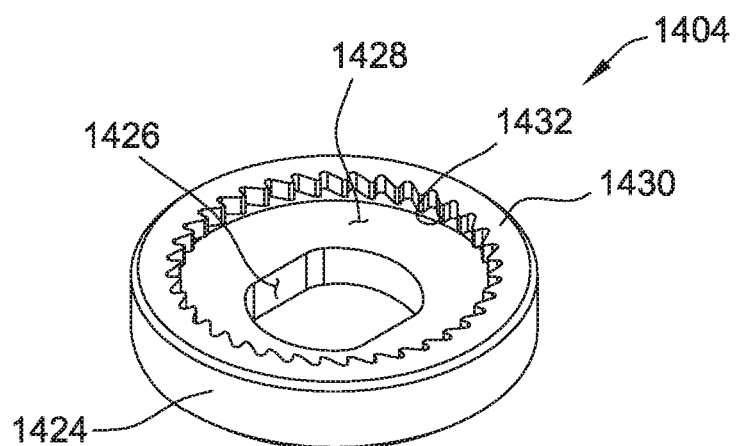
FIG. 54 is a perspective view of a lock washer of the adjustable diameter fastener assembly shown in FIG. 49.
Figure 55:
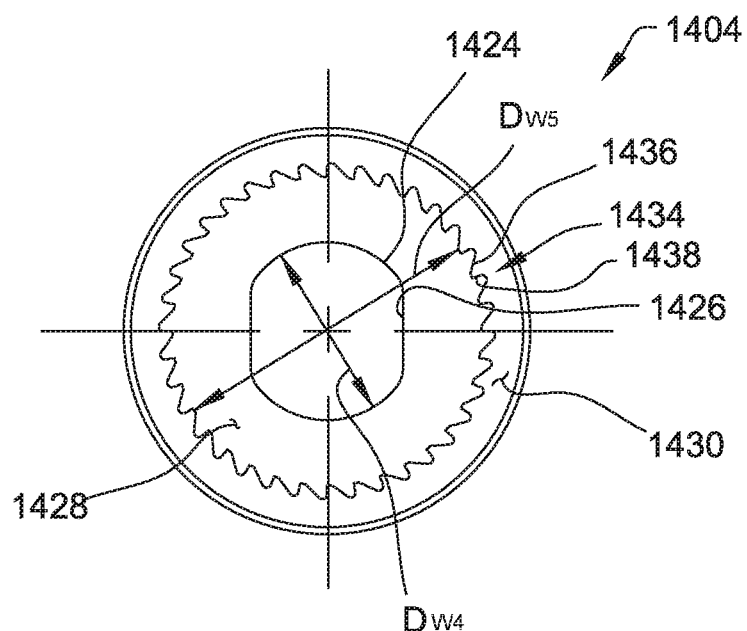
FIG. 55 is a top view of the lock washer shown in FIG. 54.

FIG. 54 is a perspective view of lock washer 1404, and FIG. 55 is a top plan view of lock washer 1404. In the exemplary embodiment, lock washer 1404 is configured to slidably couple to anti-rotation features 1418 for axial movement along threaded member 1408. Anti-rotation features 1418 facilitate rotationally fixing lock washer 1404 relative to the threaded member 1408. Lock washer 1404 includes an axial aperture 1424 that extends through lock washer 1404. Axial aperture 1424 is sized to facilitate freely sliding lock washer 1404 onto body portion 1416 of threaded member 1408. As such, axial aperture 1424 has a diameter "$D_{W4}$" slightly greater than diameter "D" of body portion 1416. Axial aperture 1424 also includes an anti-rotation structure 1426 configured to engage anti-rotation feature 1418 of threaded member 1408. It is contemplated that anti-rotation structure 1426 includes, for example, and without limitation, a finger, a member, flats, notches, grooves, and/or any other component configured to engage anti-rotation feature 1418. In the exemplary embodiment, anti-rotation structure 1426 includes a pair of opposing flat inner surfaces sized and shaped to correspond to the pair of opposing longitudinally extending anti-rotation features 1418 of body portion 1416. Anti-rotation features 1418 slidably couple with anti-rotation structures 1426 of lock washer 1404 to rotationally fix lock washer 1404 when body portion 1416 is inserted in axial aperture 1424. As such, lock washer 1404 moves freely along body portion 1416 in the axial direction.

Lock washer 1404 also includes a central portion 1428 surrounding axial aperture 1424 and configured to contact a bottom surface 1443 (shown in FIG. 57) of lock nut 1412 (shown in FIG. 57) in face-to-face contact. A circumferential wall 1430 extends axially-upward from central portion 1428 about a periphery of lock washer 1404. Circumferential wall 1430 has a radially-inner surface 1432 that defines inner cavity diameter "$D_{W5}$" of lock washer 1404. Inner cavity diameter "$D_{W5}$" is sized to receive an annular body 1460 (shown in FIG. 58) of lock member 1406 (shown in FIG. 58) therein. Circumferential wall 1430 has a plurality of notches 1434, or locking teeth, defined in radially-inner surface 1432 of circumferential wall 1430. In the exemplary embodiment, each notch 1434 is defined by a sliding surface 1436, securing surface 1438, and radially-inner surface 1432, and is configured to correspond to a sliding surface 1484 (shown in FIG. 59) and a securing surface 1486 (shown in FIG. 59), respectively, of a respective tooth 1464 (shown in FIG. 59) of lock member 1406. In particular, securing surface 1438 is substantially orthogonal to radially-inner surface 1432 and configured to contact securing surface 1486 of tooth 1464 in face-to-face contact. Sliding surface 1436 is formed oblique to radially-inner surface 1432 configured to contact sliding surface 1484 of tooth 1464 in face-to-face contact.

In the exemplary embodiment, lock washer 1404 is fabricated from a metal, for example, and without limitation, steel, aluminum, titanium, or a superalloy. Alternatively, lock washer 1404 is fabricated from any material that enables adjustable diameter fastener assembly 1400 to function as described herein, such as, for example, and without limitation, composite materials, resins, fiber reinforced resins, plastics, and fiber reinforced plastics.

Figure 56:
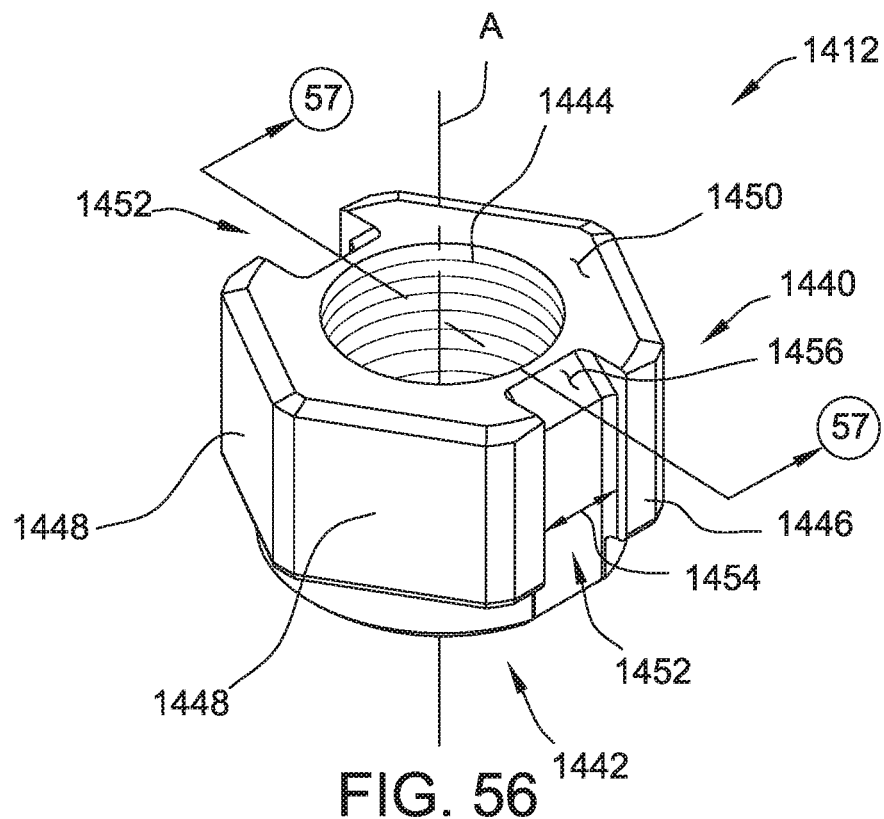
FIG. 56 is a perspective view of a lock nut of the adjustable diameter fastener assembly shown in FIG. 49.
Figure 57:
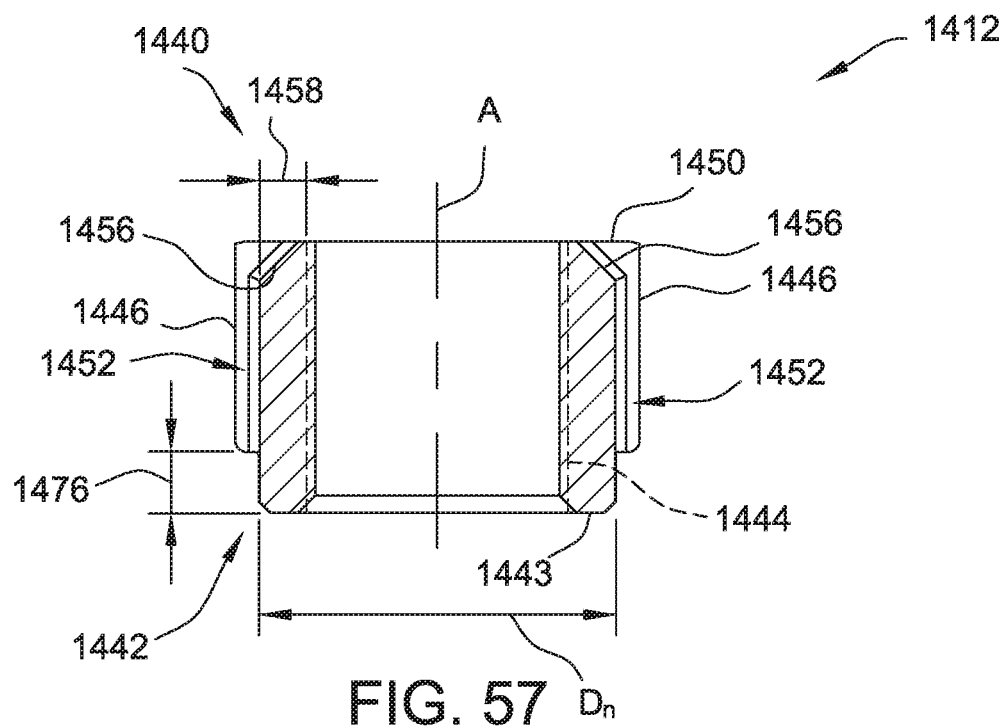
FIG. 57 is a sectional view of the lock nut shown in FIG. 56 taken through line 23-23.

FIG. 56 is a perspective view of lock nut 1412, and FIG. 57 is a sectional view of lock nut 1412 taken through line 23-23 (shown in FIG. 56). In the exemplary embodiment, lock nut 1412 includes a head portion 1440 and a shoulder portion 1442 extending axially from head portion 1440 along longitudinal axis "A." A female threaded portion 1444 extends through lock nut 1412 and is formed about longitudinal axis "A." Head portion 1440 includes one or more slotted circumferential faces 1446 and one or more continuous faces 1448. Slotted circumferential faces 1446 and continuous faces 1448, combined, define tool engagement surfaces that extend substantially axially between shoulder portion 1442 and a top surface 1450 of lock nut 1412, opposite shoulder portion 1442. The tool engagement surfaces are configured in a hexagonal-shaped arrangement, although other configurations are contemplated. The tool engagement surfaces correspond to one or more tools, for example, and without limitation, a wrench and/or a socket. As such, the tool engagement surfaces facilitate tightening and/or loosening lock nut 1412 using common hand tools, and without requiring use of a specialized tool.

In the exemplary embodiment, each slotted circumferential face 1446 defines an axial slot 1452. Each axial slot 1452 extends generally axially along slotted circumferential face 1446 from top surface 1450 of lock nut 1412, and has a circumferential width 1454 sized to receive a spring finger 1462 (shown in FIG. 58) of lock member 1406 (shown in FIG. 58). This facilitates fixing lock member 1406 rotationally with respect to lock nut 1412 when axial slot 1452 is aligned with spring finger 1462. In particular, spring finger 1462 snaps into axial slot 1452 to facilitate coupling lock member 1406 to lock nut 1412. A top portion 1456 of axial slot 1452 tapers inward toward longitudinal axis "A" a predetermined distance 1458 to define a ledge that receives an ear portion 1482 of spring finger 1462. This facilitates retaining lock member 1406 on lock nut 1412 about longitudinal axis "A."

In the exemplary embodiment, lock nut 1412 includes two axial slots 1452 disposed on diametrically-opposed slotted circumferential faces 1446, i.e. on slotted circumferential faces 1446 that are substantially parallel to each other and generally positioned symmetrical to each other with respect to longitudinal axis "A." In alternative embodiments, lock nut 1412 includes fewer or greater than two axial slots 1452, such that, for example, a respective axial slot 1452 is circumferentially-positioned relative to a respective spring finger 1462 of lock member 1406.

In the exemplary embodiment, lock nut 1412 is fabricated from a metal, for example, and without limitation, steel, aluminum, titanium, or a superalloy. Alternatively, lock nut 1412 is fabricated from any material that enables adjustable diameter fastener assembly 1400 to function as described herein, such as, for example, and without limitation, composite materials, resins, fiber reinforced resins, plastics, and fiber reinforced plastics.

Figure 58:
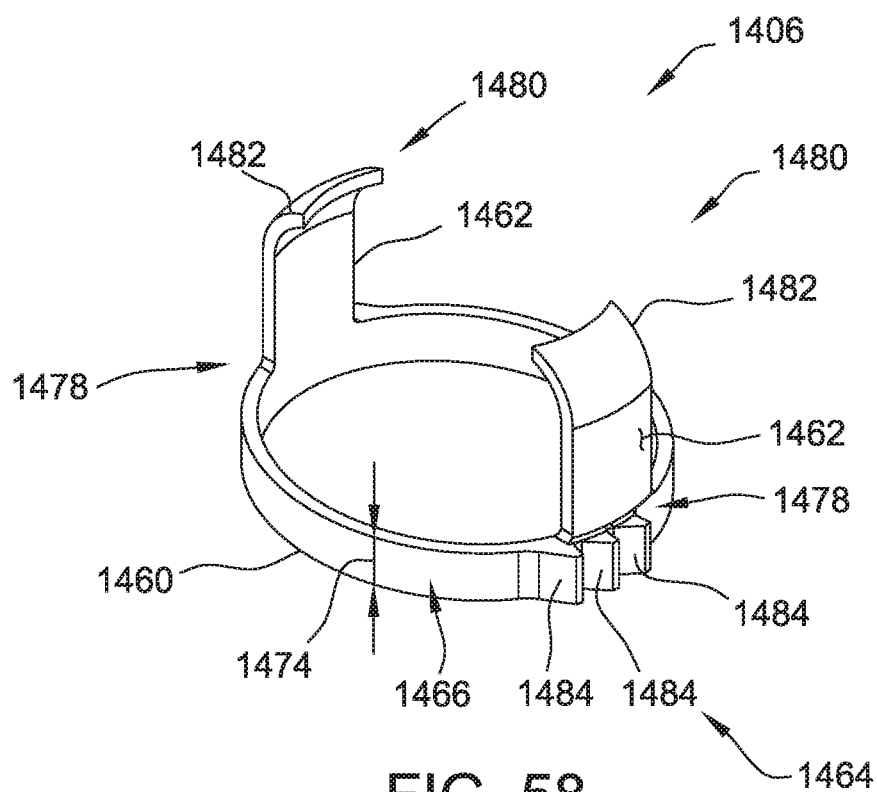
FIG. 58 is a perspective view of a lock member of the adjustable diameter fastener assembly shown in FIG. 49.
Figure 59:
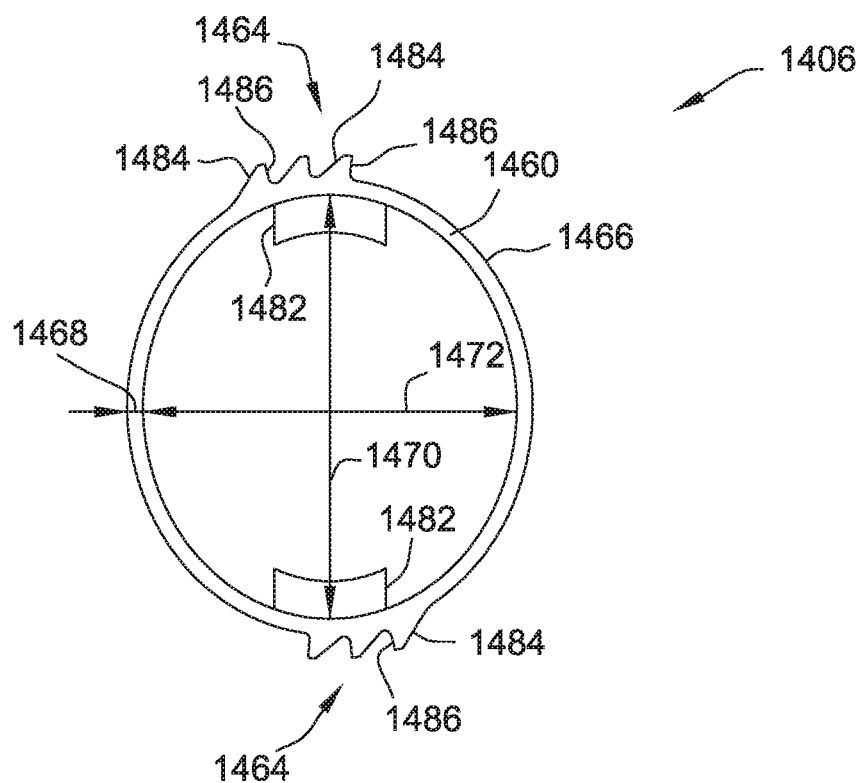
FIG. 59 is a bottom view of the lock member shown in FIG. 58.

FIG. 58 is a perspective view of lock member 1406, and FIG. 59 is a bottom view of lock member 1406. In the exemplary embodiment, lock member 1406 includes a ring-shaped annular body 1460 having one or more spring fingers 1462 extending generally axially upward from annular body 1460. Annular body 1460 includes one or more radially-extending teeth 1464 (broadly detent members) disposed on an outer surface 1466 of annular body 1460. In the exemplary embodiment, annular body 1460 is a generally oval-shaped ring having a predetermined wall thickness 1468, that when combined with an inner major axis length 1470, facilitates fitting within inner cavity diameter "$D_{WS}$" (shown in FIG. 55) of lock washer 1404 (shown in FIG. 54). Annular body 1460 also has a predetermined inner minor axis length 1472 that corresponds to a diameter "$D_n$" (shown in FIG. 57) shoulder portion 1442 (shown in FIG. 57) of lock nut 1412 (shown in FIG. 57) to facilitate coupling lock member 1406 to lock nut 1412. In the exemplary embodiment, inner major axis length 1470 is greater than inner minor axis length 1472. Annular body 1460 also has a height 1474 that is slightly shorter than a height 1476 (shown in FIG. 57) of shoulder portion 1442 of lock nut 1412, such that lock member 1406 remains able to be deflected or flexed, as described further herein, when shoulder portion 1442 applies an axial force against lock washer 1404. In the exemplary embodiment, annular body 1460 is deflectable, such that, in response to a radial force exerted thereon by one or more of spring fingers 1462, annular body 1460 is radially-deflected, becoming more or less circular based upon an amount of the radial force exerted on annular body 1460.

It is contemplated that annular body 1460 may have shapes other than oval, for example, and without limitation, annular body 1460 may be round, ellipsoid, or any other suitable shape. In the exemplary embodiment, annular body 1460 is fabricated from a resilient metallic material, such as a spring steel. Alternatively, annular body 1460 is fabricated from any resilient material that enables lock member 1406 to function as described herein, for example, and without limitation, resilient composite materials, resins, fiber reinforced resins, plastics, and fiber reinforced plastics.

In the exemplary embodiment, each spring finger 1462 extends axially upward from annular body 1460 from a fixed end 1478 to a free end 1480. Fixed end 1478 is coupled to annular body 1460. Free end 1480 extends radially inward and defines an ear portion 1482. Ear portion 1482 extends radially inward such that when coupled to lock nut 1412, ear portion 1482 extends over top portion 1456 (shown in FIG. 57) of axial slot 1452 (shown in FIG. 57) to facilitate retaining lock member 1406 on lock nut 1412. In one embodiment, free end 1480 curves inward to form ear portion 1482. Alternatively, free end 1480 is bent and/or slanted radially inward to define ear portion 1482, or otherwise extends radially-inward in any manner that enables lock member 1406 to function described herein. In the exemplary embodiment, each spring finger 1462 is formed substantially the same. While lock member 1406 is described with two spring fingers 1462, in alternative embodiments, lock member 1406 includes fewer or greater than two spring fingers 1462, such that, for example, a respective spring finger 1462 is circumferentially-positioned relative to a respective axial slot 1452 of lock nut 1412.

As described above, one or more radially-extending teeth 1464 (or detent members) are disposed on outer surface 1466 of annular body 1460. In particular, in the exemplary embodiment, sets of three adjacent radially-extending teeth 1464 are disposed on annular body 1460 with each set generally circumferentially aligned relative to a respective spring finger 1462. Each tooth 1464 includes a sliding surface 1484 and a securing surface 1486. Sliding surface 1484 and securing surface 1486 are sized and shaped to correspond to sliding surface 1436 (shown in FIG. 55) and securing surface 1438 (shown in FIG. 55), respectively, of notches 1434 (shown in FIG. 55) of lock washer 1404. In the exemplary embodiment, radially-extending teeth 1464 are configured to facilitate preventing rotation that affects loosening of lock nut 1412 with respect to lock washer 1404, for example, rotation in a counter-clockwise direction. Alternatively, radially-extending teeth 1464 are configured to facilitate preventing rotation of lock nut 1412 in the clockwise direction, or both the counter-clockwise and the clockwise directions. While lock member 1406 is described with three radially-extending teeth 1464 formed proximate each spring finger 1462, in alternative embodiments, lock member 1406 includes fewer or greater than three teeth 1464.

In operation, with reference to FIG. 50, in first orientation 1402, lock washer 1404, lock member 1406, and lock nut 1412 are fixed axially and rotationally relative to threaded member 1408. In second orientation 1410 shown in FIG. 51, lock member 1406 and lock nut 1412 are rotationally free relative to threaded member 1408. Rotation of lock nut 1412 relative to threaded member 1408 displaces lock nut 1412 and lock member 1406 axially relative to threaded member 1408, facilitating adjusting the diameter of adjustable diameter fastener assembly 1400. In particular, lock nut 1412 displaces lock washer 1404 axially relative to threaded member 1408 such that lock washer 1404 applies an axial (or compression) force against thrust ring 1022 proximate threaded portion 1420 of threaded member 1408. At the opposite end of threaded member 1408, thrust washer 1026 is seated against a second thrust ring 1022. Continued rotation of lock nut 1412 facilitates compressing bushing 1024 to thus shorten the overall length of bushing 1024. As such, inner rings 1032 contract and outer rings 1030 are forced to expand and assume an increased diameter, thereby facilitating adjusting the outside diameter of bushing 1024.

In first orientation 1402, threaded portion 1420 of threaded member 1408 is inserted through axial aperture 1424 of lock washer 1404 such that anti-rotation structures 1426 engage anti-rotation features 1418 of threaded member 1408, thereby rotationally fixing lock washer 1404 relative to threaded member 1408. The oval shape of annular body 1460 (shown in FIG. 58) facilitates urging radially-extending teeth 1464, positioned generally circumferentially aligned relative to a respective spring finger 1462, radially-outward and into contact with notches 1434 of lock washer 1404. In particular, one or more of sliding surfaces 1484 and securing surfaces 1486 (shown in FIG. 59) of radially-extending teeth 1464 are urged into face-to-face contact with sliding surfaces 1436 and securing surfaces 1438 (shown in FIG. 57), respectively, of notches 1434, rotationally fixing lock member 1406 relative to lock washer 1404.

As shown in FIG. 50, in first orientation 1402, free end 1480 of spring finger 1462 seats within top portion 1456 of axial slot 1452 of lock nut 1412. Seating free end 1480 of spring finger 1462 in top portion 1456 of axial slot 1452 facilitates rotationally-fixing lock member 1406 with lock nut 1412. As such, lock member 1406 and lock nut 1412 are caused to rotate together. Consequently, when one or more radially-extending teeth 1464 of lock member 1406 seats against one or more notches 1434 of lock washer 1404, lock member 1406 becomes rotationally-fixed relative to lock washer 1404, causing lock nut 1412 to become rotationally-fixed relative to lock washer 1404 and threaded member 1408.

As described above, lock member 1406 is captured between lock nut 1412 and lock washer 1404, and in particular, about shoulder portion 1442 (shown in FIG. 56) of lock nut 1412. Because height 1474 (shown in FIG. 58) of annular body 1460 is shorter than height 1476 (shown in FIG. 57) of shoulder portion 1442 of lock nut 1412, lock member 1406 can be deflected or flexed as described herein.

In second orientation 1410, each spring finger 1462 is displaced radially inward to facilitate deflecting annular body 1460 (shown in FIG. 58) to disengage radially-extending teeth 1464 from notch 1434 of lock washer 1404. In particular, displacing fixed end 1478 (shown in FIG. 58) of spring finger 1462 radially inward facilitates disengaging one or more of sliding surfaces 1484 and securing surfaces 1486 (shown in FIG. 59) of radially-extending teeth 1464 from face-to-face contact with sliding surfaces 1436 and securing surfaces 1438 (shown in FIG. 55), respectively, of notches 1434 to facilitate rotation of lock nut 1412 and lock member 1406 relative to lock washer 1404.

To facilitate displacing spring fingers 1462 radially inward, as described herein, a tool (not shown), such as a conventional socket or wrench, is coupled to lock nut 1412. The tool is axially displaced relative to lock nut 1412 where it contacts free end 1480 of spring fingers 1462. As described above, free end 1480 curves inward to form ear portion 1482 (shown in FIG. 58). As the tool contacts ear portion 1482, spring fingers 1462 are radially displaced, facilitating deflecting annular body 1460 such that radially-extending teeth 1464 are disengaged from notches 1434. The tool may be rotated either clockwise or counterclockwise about longitudinal axis "A" to displace lock nut 1412 axially in either direction along longitudinal axis "A," tightening lock nut 1412 or loosening lock nut 1412 as appropriate. Thus, when a tool such as a conventional socket or wrench is applied to lock nut 1412, lock member 1406 is deflected radially inward such that teeth 1464 of lock member 1406 disengage notches 1434 of lock washer 1404, thereby allowing rotation of lock member 1406 and lock nut 1412 relative to lock washer 1404 and threaded member 1408.

Figure 60:
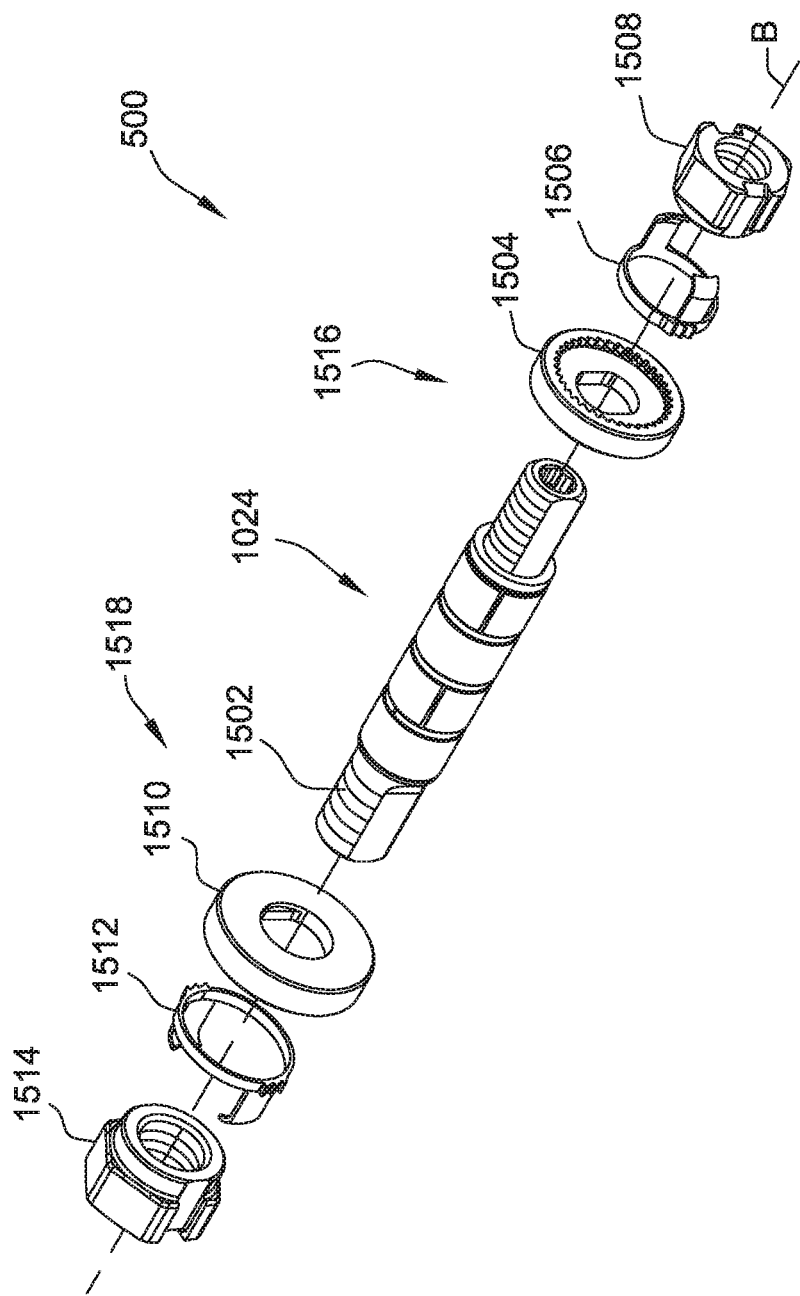
FIG. 60 is an exploded perspective view of an alternative adjustable diameter fastener assembly.

FIG. 60 is an exploded perspective view of an alternative adjustable diameter fastener assembly 1500. In the exemplary embodiment, adjustable diameter fastener assembly 1500 is similar to adjustable diameter fastener assembly 1400 (shown in FIG. 49) and includes a first lock washer 1504, a first lock member 1506, and a first lock nut 1508 proximate a first end 1516 of a threaded member 1502. In addition, adjustable diameter fastener assembly 1500 includes a second lock washer 1510, a second lock member 1512, and a second lock nut 1514 proximate a second end 1518 of threaded member 1502. In the exemplary embodiment, adjustable diameter fastener assembly 1500 is an adjustable diameter clamping bolt of the adjustable bushing fastener type that operates by radial expansion of radially expandable bushing 1024. Alternatively, adjustable diameter fastener assembly 1500 is any type of adjustable diameter fastener assembly, for example, and without limitation, a compression or clamp-up type fastener assembly.

In the exemplary embodiment, adjustable diameter fastener assembly 1500 functions substantially similar to adjustable diameter fastener assembly 1400, but includes a second set of locking components in place of head portion 1414 (shown in FIG. 49) of threaded member 1408 (shown in FIG. 49). In particular, first lock washer 1504 and second lock washer 1510 are fabricated substantially similar to lock washer 1404 (shown in FIG. 49); first lock member 1506 and second lock member 1512 are fabricated substantially similar to lock member 1406 (shown in FIG. 49); and first lock nut 1508 and second lock nut 1514 are fabricated substantially similar to lock nut 1412 (shown in FIG. 49). It is noted that the relative size of the components may differ; however, the general function is substantially the same as adjustable diameter fastener assembly 1400. In particular, the rotational fixing of first lock nut 1508 and second lock nut 1514 is substantially the same as described above for adjustable diameter fastener assembly 1400, with respect to FIGS. 50 and 51.

Figure 61:
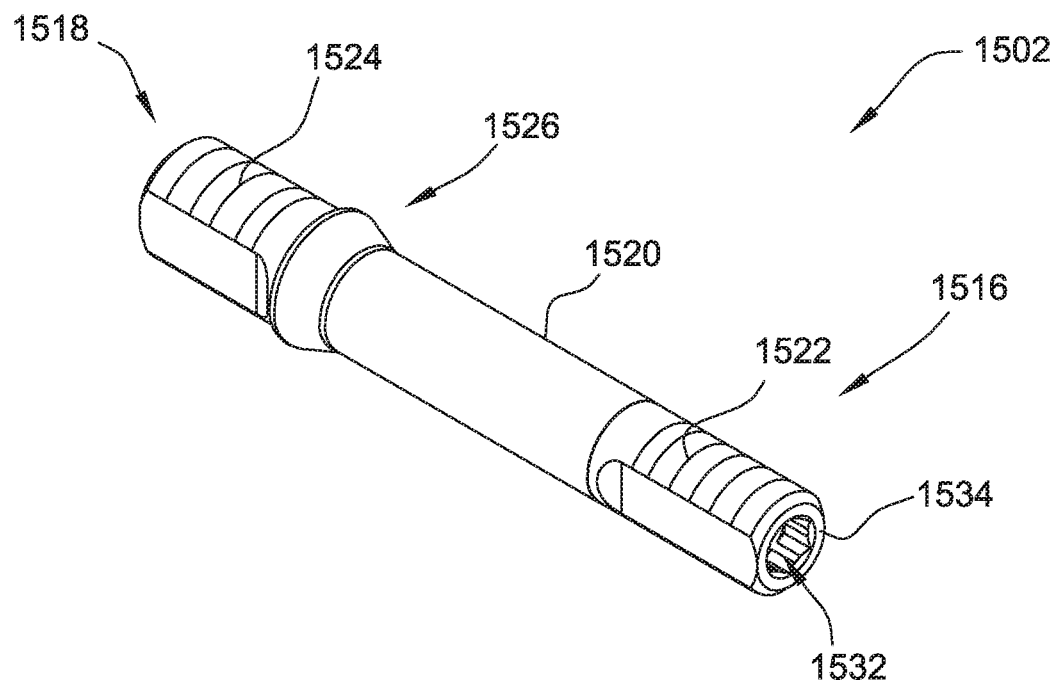
FIG. 61 is a perspective view of a threaded member of the adjustable diameter fastener assembly shown in FIG. 60.
Figure 62:
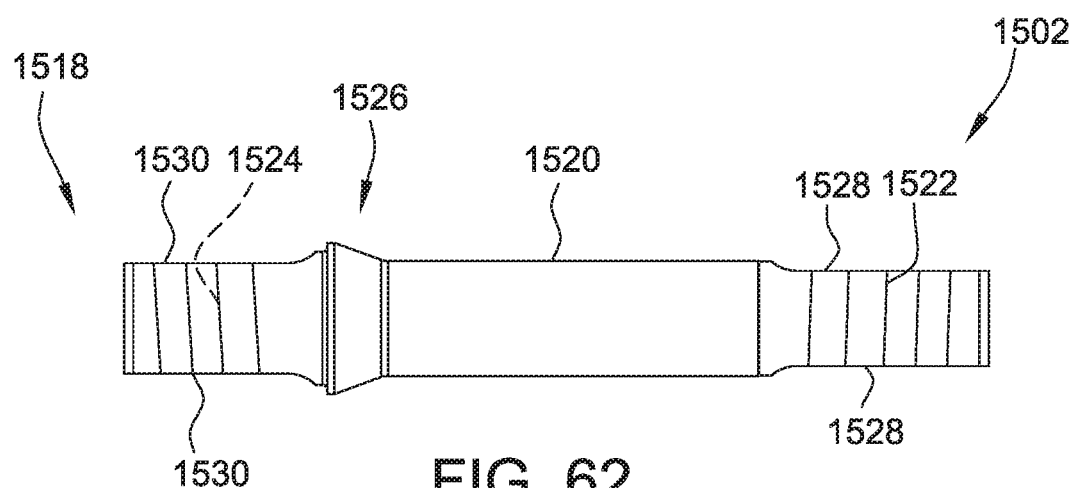
FIG. 62 is a side view of the threaded member shown in FIG. 61.

FIG. 61 is a perspective view of threaded member 1502, and FIG. 62 is a side view of threaded member 1502. Threaded member 1502 includes an elongated body portion 1520 extending axially from first end 1516 to second end 1518. Threaded member 1502 also includes a first threaded portion 1522 at first end 1516, and a second threaded portion 1524 at second end 1518. A wedge portion 1526 is formed proximate second end 1518 and is configured to receive a portion of bushing 1024 (shown in FIG. 60) to facilitate compression of bushing 1024 during use of adjustable diameter fastener assembly 1500. At least one first anti-rotation feature 1528 is formed at first end 1516, and at least one second anti-rotation feature 1530 is formed at second end 1518.

In the exemplary embodiment, first anti-rotation feature 1528 and second anti-rotation feature 1530 are formed substantially similar to anti-rotation feature 1418 (shown in FIG. 52) and includes a pair of opposing, longitudinally extending sections formed in first threaded portion 1522 and second threaded portion 1524, respectively. It is contemplated that anti-rotation features 1528 and 1530 include, for example, and without limitation, flats, notches, grooves, and/or any other feature that enables threaded member 1502 to function as described herein. In the exemplary embodiment, first anti-rotation feature 1528 includes a pair of flat portions that are parallel to each other, are substantially equal in size and shape, and extend along at least a portion of threaded portion 1522. It is contemplated that anti-rotation features 1528 can extend any length along body portion 1520, up to and including extending to wedge portion 1526. In addition, second anti-rotation feature 1530 also includes a pair of flat portions that are parallel to each other, are substantially equal in size and shape, and extend along at least a portion of threaded portion 1524. It is contemplated that anti-rotation features 1530 can extend any length along body portion 1520, up to and including extending to wedge portion 1526.

In the exemplary embodiment, as shown in FIG. 61, first end 1516 of threaded member 1502 includes a socket 1532 formed in an end face 1534 of body portion 1520. Socket 1532 is formed as a hexagonal socket to facilitate receiving a tool used to secure threaded member 1502 against rotation while one or more of lock nuts 1508 and 1514 are tightened and/or loosened. Alternatively, socket 1532 is any shape or form, for example, and without limitation, a spline head and/or a slot, that enables adjustable diameter fastener assembly 1500 to function as described herein.

Figure 63:
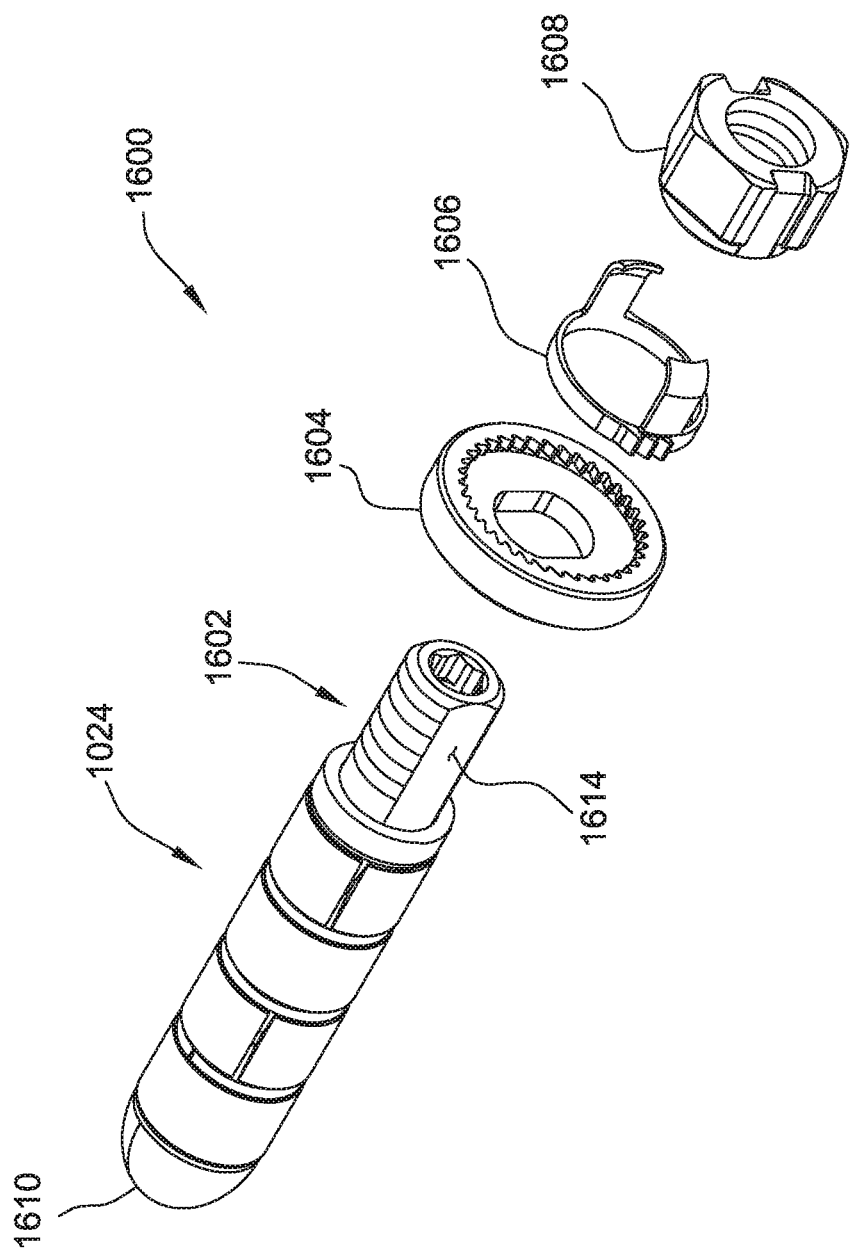
FIG. 63 is an exploded perspective view of another alternative adjustable diameter fastener assembly.

FIG. 63 is an exploded perspective view of an alternative adjustable diameter fastener assembly 1600. In the exemplary embodiment, adjustable diameter fastener assembly 1600 is similar to adjustable diameter fastener assembly 1400 (shown in FIG. 49) and includes a threaded member 1602, bushing 1024, a lock washer 1604, a lock member 1606, and a lock nut 1608. In the exemplary embodiment, adjustable diameter fastener assembly 1600 is an adjustable diameter blind bolt of the adjustable bushing fastener type that operates by radial expansion of radially expandable bushing 1024. Alternatively, adjustable diameter fastener assembly 1600 is any type of adjustable diameter fastener assembly, for example, and without limitation, a compression or clamp-up type fastener assembly.

In the exemplary embodiment, adjustable diameter fastener assembly 1600 functions substantially similar to adjustable diameter fastener assembly 1400, but includes a smooth head portion 1610 rather than the hexagonal head portion 1414 (shown in FIG. 49) of threaded member 1408 (shown in FIG. 49). In particular, lock washer 1604 is fabricated substantially similar to lock washer 1404 (shown in FIG. 49), lock member 1606 is fabricated substantially similar to lock member 1406 (shown in FIG. 49), and lock nut 1608 is fabricated substantially similar to lock nut 1412 (shown in FIG. 49). As such, the rotational fixing of lock nut 1608 is substantially the same as described above for adjustable diameter fastener assembly 1400, with respect to FIGS. 50 and 51.

Figure 64:
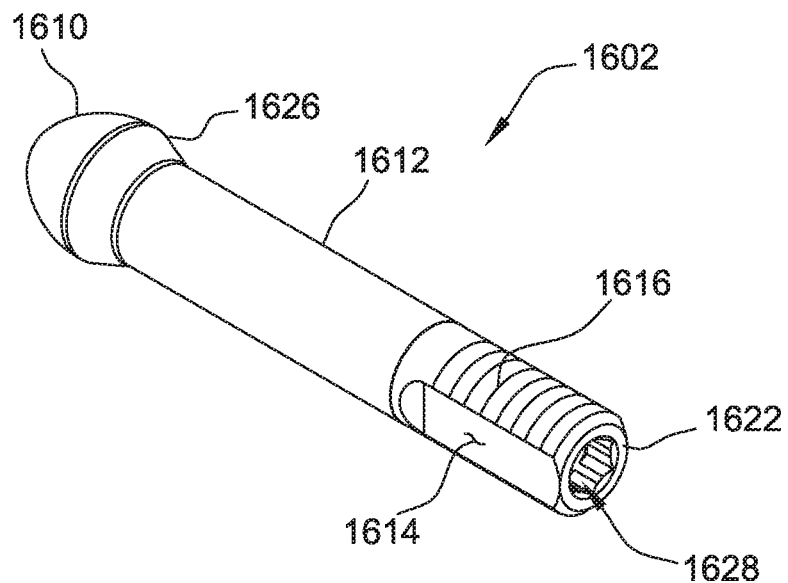
FIG. 64 is a perspective view of a threaded member of the adjustable diameter fastener assembly shown in FIG. 63.
Figure 65:
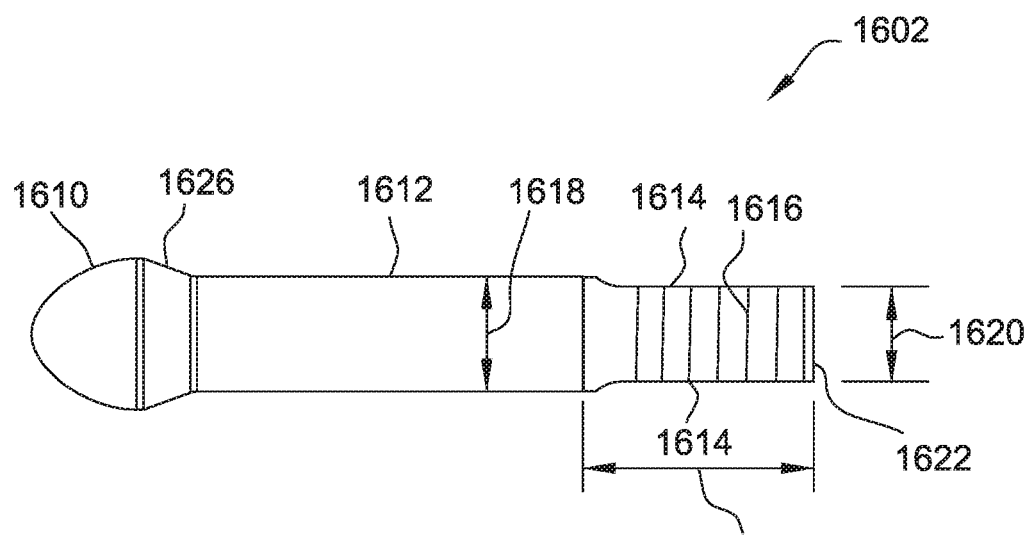
FIG. 65 is a side view of the threaded member shown in FIG. 64.

FIG. 64 is a perspective view of threaded member 1602, and FIG. 65 is a side view of threaded member 1602. In the exemplary embodiment, threaded member 1602 includes a smooth head portion 1610, an elongated body portion 1612 extending axially from head portion 1610, and at least one anti-rotation feature 1614. Anti-rotation feature 1614 is formed substantially similar to anti-rotation feature 1418 (shown in FIG. 52) and includes a pair of opposing longitudinally extending sections formed in a threaded portion 1616 of body portion 1612. It is contemplated that anti-rotation feature 1614 includes, for example, and without limitation, flats, notches, grooves, and/or any other feature that enables threaded member 1602 to function as described herein. Body portion 1612 has a diameter 1618 defining a size of threaded member 1602. Anti-rotation feature 1614 includes a pair of flat portions that are parallel to each other and are spaced apart a width 1620 which is smaller than diameter 1618. Anti-rotation features 1614 are substantially equal in size and shape, and extend along at least a portion of threaded portion 1616 of body portion 1612 from an end 1622 of threaded member 1602 a predefined length 1624. It is contemplated that anti-rotation features 1614 can extend any length 1624 along body portion 1612, up to and including extending to head portion 1610.

In the exemplary embodiment, as shown in FIG. 63, head portion 1610 is a curved or rounded head having a width substantially similar to a width or diameter of bushing 1024. Alternatively, head portion 1610 is any shape or form that enables adjustable diameter fastener assembly 1600 to function as described herein. Head portion 1610 includes a wedge portion 1626 configured to receive a portion of bushing 1024 (shown in FIG. 63) to facilitate compression of bushing 1024 during use of adjustable diameter fastener assembly 1600.

In the exemplary embodiment, as shown in FIG. 64, end 1622 of threaded member 1602 includes a socket 1628 formed in body portion 1612. Socket 1628 is formed as a hexagonal socket to facilitate receiving a tool used to secure threaded member 1602 against rotation while lock nut 1608 is tightened and/or loosened. Alternatively, socket 1628 is any shape or form, for example, and without limitation, a spline head and/or a slot, that enables adjustable diameter fastener assembly 1600 to function as described herein.

Figure 66:
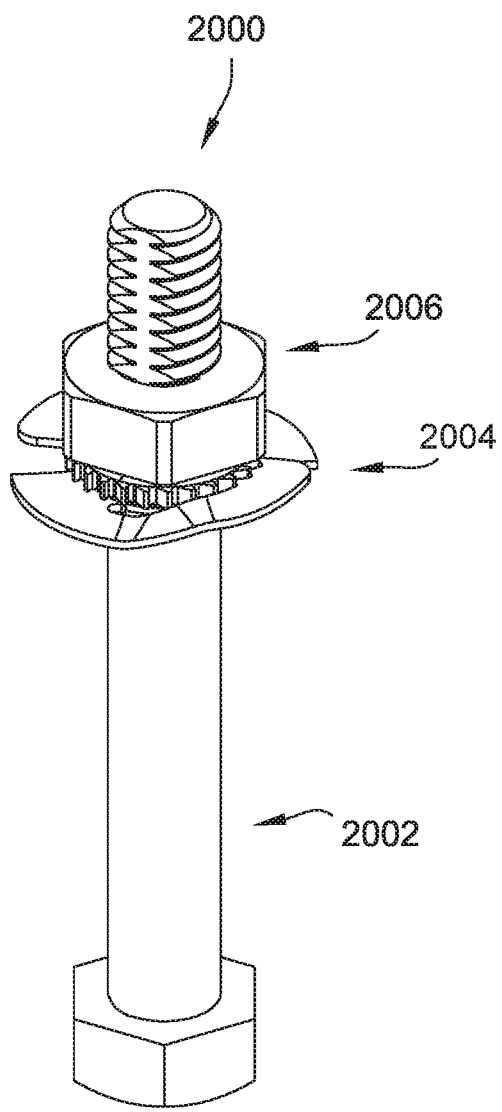
FIG. 66 is a perspective view of another exemplary embodiment of a fastener assembly, showing a lock nut, a lock washer, and a bolt of the fastener device.
Figure 67:
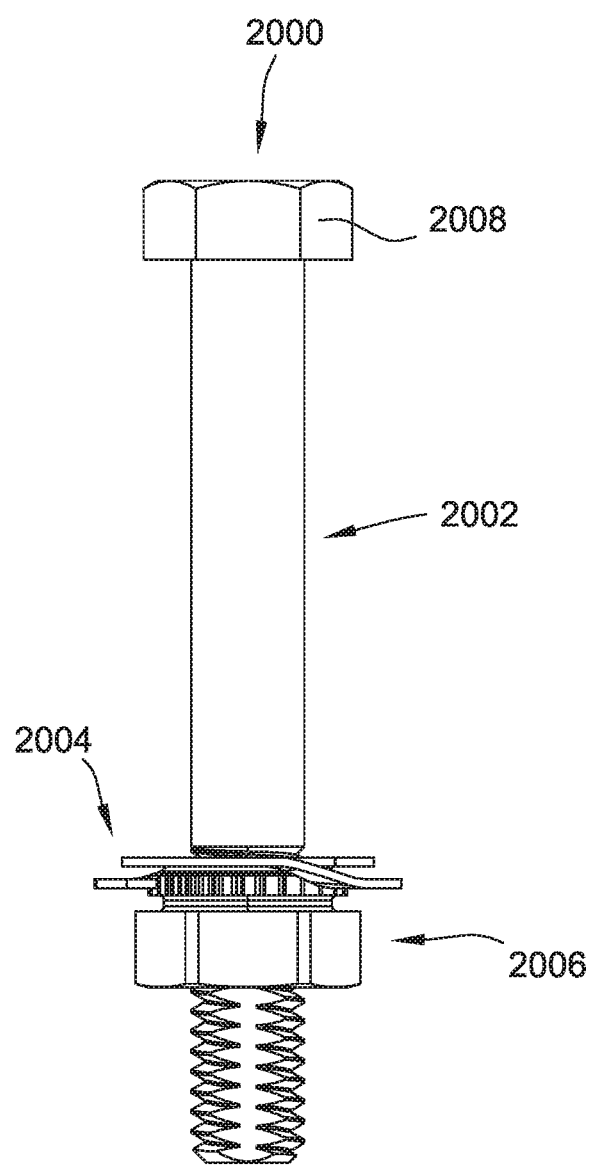
FIG. 67 is a side view of the fastener assembly shown in FIG. 66.
Figure 68:
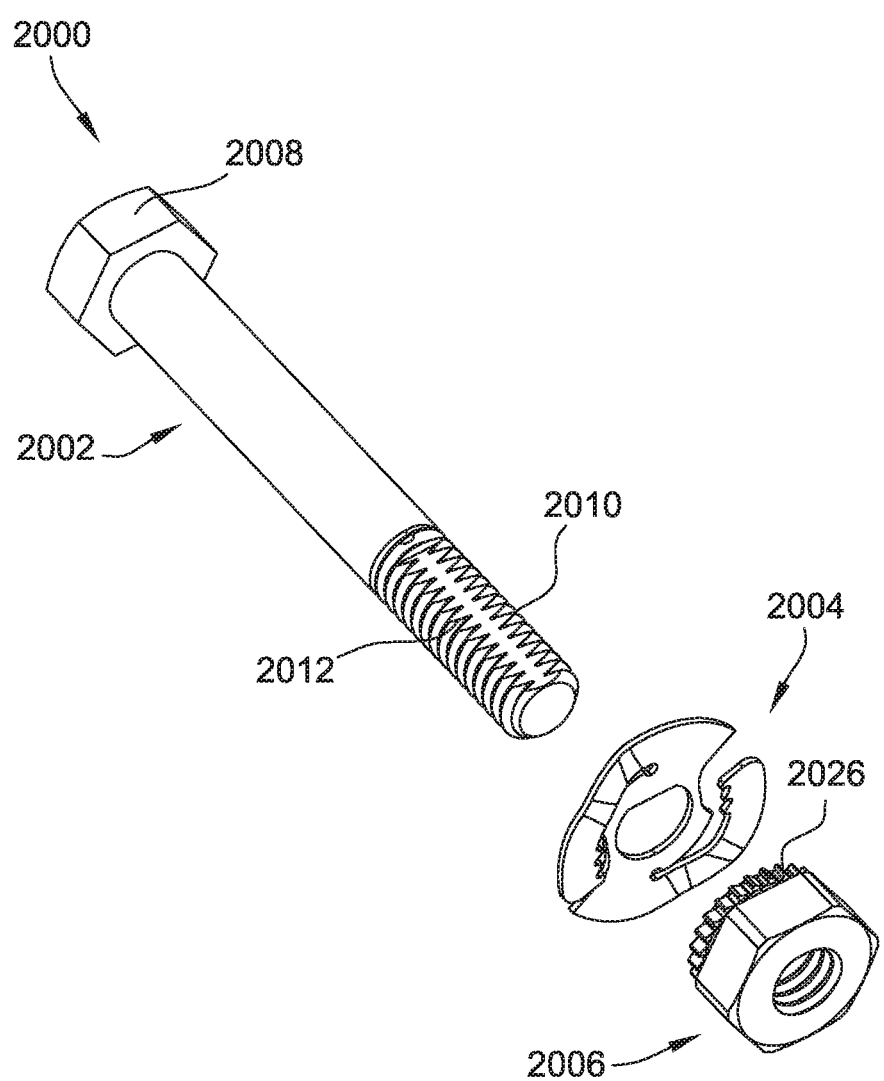
FIG. 68 is an exploded perspective view the fastener shown in FIG. 66.
Figure 69:
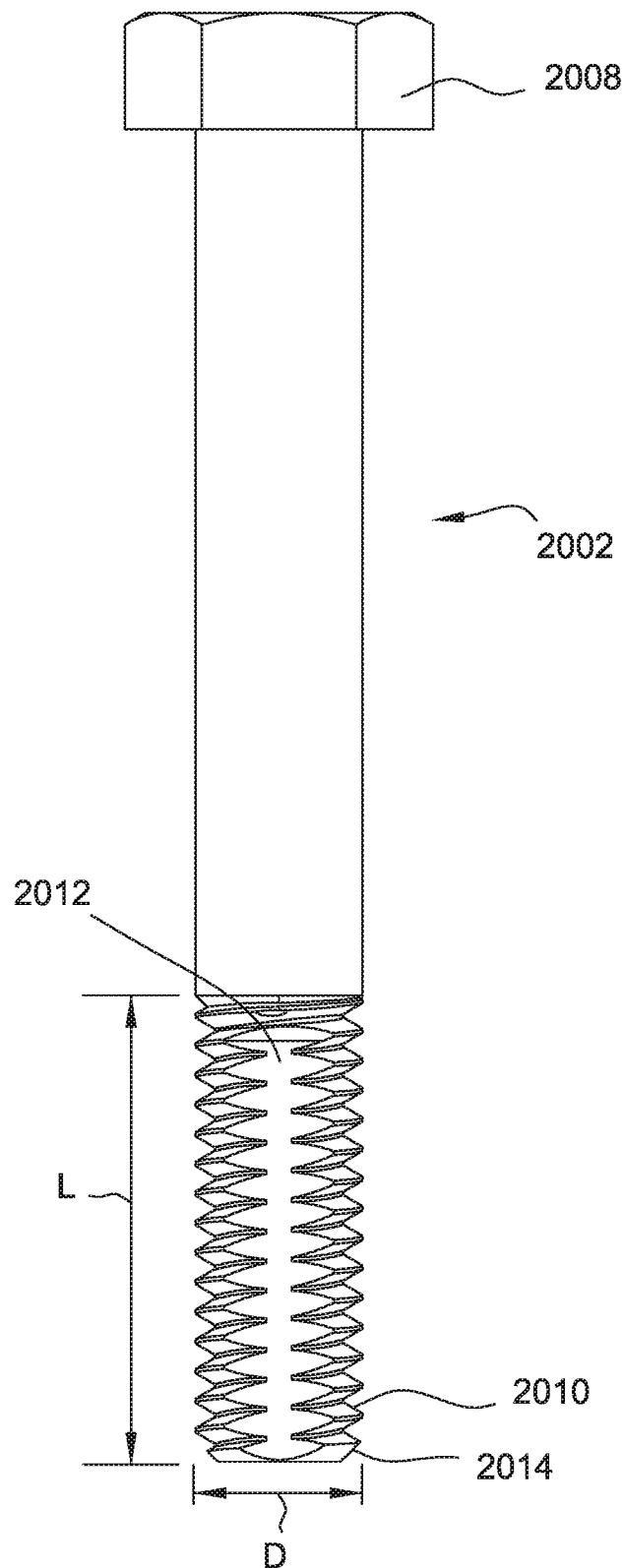
FIG. 69 is a side view of the bolt of the fastener assembly shown in FIG. 66.

FIG. 66 is a perspective view of an exemplary embodiment of a fastener assembly 2000. FIG. 67 is a side view of fastener assembly 2000. FIG. 68 is an exploded perspective view of fastener assembly 2000. In the exemplary embodiment, fastener assembly 2000 includes a threaded member 2002, a lock washer member 2004, and a lock nut member 2006. Threaded member 2002 includes a head portion 2008, an elongated threaded body portion 2010 extending axially from head portion 2008, and at least one banking feature, or anti-rotation feature 2012. Alternatively, threaded member 2002 may be free of head portion 2008. For example, and without limitation, threaded member 2002 may be a threaded rod, a bolt, a screw, or any other threaded component that enables fastener assembly 2000 to function as described herein. Lock washer 2004 is configured to slidably couple to anti-rotation features 2012 of threaded body portion 2010 for axial movement along threaded body portion 2010. Anti-rotation features 2012 facilitate rotationally fixing lock washer 2004 relative to the threaded member 2002. In alternative embodiments, lock washer 2004 is coupled to threaded member 2002 in any manner that enables fastener assembly 2000 to operate as described herein. FIG. 69 is a side view of threaded member 2002 of fastener assembly 2000 (shown in FIGS. 66-68). Threaded body portion 2010 of threaded member 2002 has a diameter "D" defining a size of threaded member 2002. In the exemplary embodiment, anti-rotation features 2012 on fastener assembly 2000 include a pair of opposing longitudinally extending sections formed in threaded body portion 2010. It is contemplated that anti-rotation features 2012 can include, for example, and without limitation, flats, notches, grooves, and/or any other feature that enables threaded member 2002 to function as described herein. In the exemplary embodiment, anti-rotation features 2012 include a pair of flat portions that are parallel to each other and are spaced apart a width "W", (shown in FIG. 53) which is smaller than diameter "D". Anti-rotation features 2012 are substantially equal in size and shape, and extend along threaded body portion 2010 from an end 2014 of threaded member 2002 a predefined length "L". It is contemplated that anti-rotation features 2012 can extend any length "L" along threaded body portion 2010, up to and including extending to head portion 2008.

Figure 70:
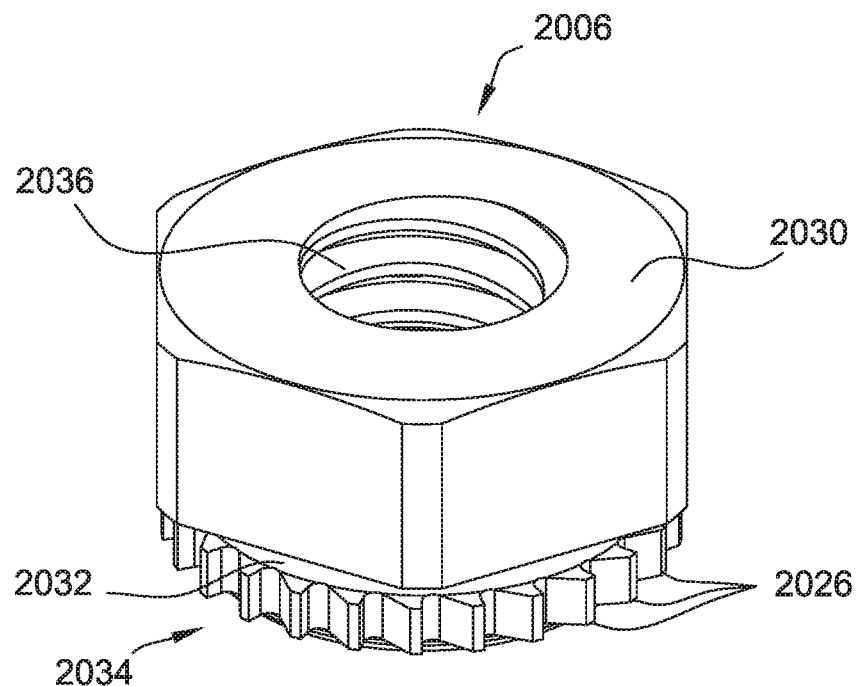
FIG. 70 is a perspective view of the lock nut of the fastener assembly shown in FIG. 66.
Figure 71:
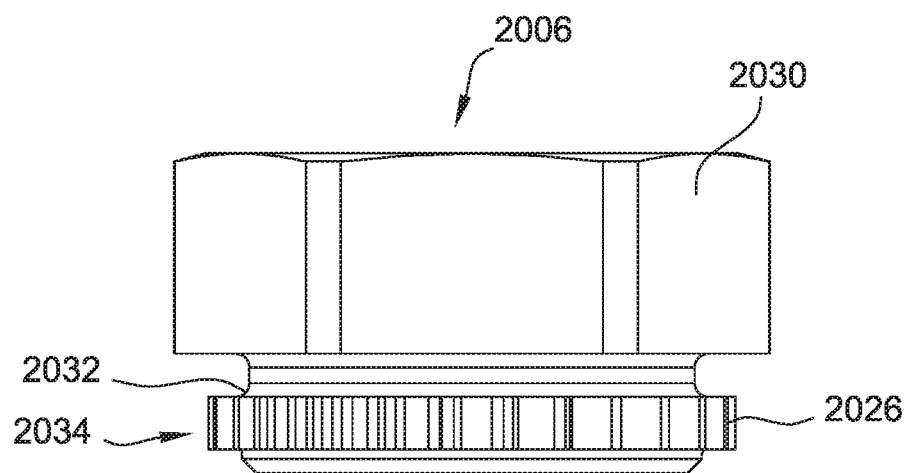
FIG. 71 is a side view of the lock nut shown in FIG. 70.
Figure 72:
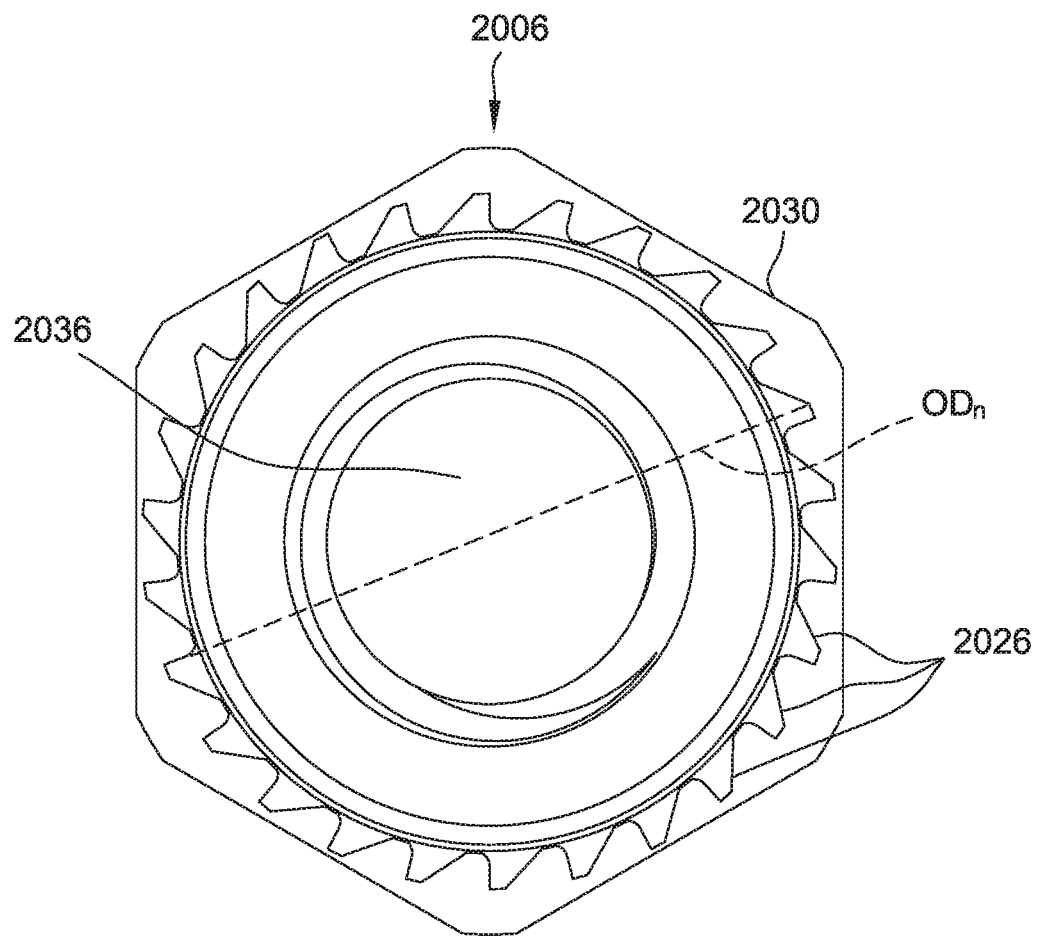
FIG. 72 is a bottom view of the lock nut shown in FIG. 70.

With reference to FIGS. 70-72, lock nut member 2006 includes a body 2030 and a transversely extending flange 2032 proximate a first end 2034 of lock nut member 2006. In the exemplary embodiment, flange 2032 is integrally formed with body 2030. In the exemplary embodiment, flange 2032 has a diameter "$OD_n$." Body 2030 includes a threaded bore 2036 extending axially through lock nut member 2006. Body 2030 is formed as a hexagonal-shaped body, although other configurations of body 2030 are contemplated. It is understood that, in other embodiments, locking teeth 2026 are configured to have any other suitable shapes that enable lock nut member 2006 to function as described herein. Alternatively, lock nut member 2006 has any number of locking teeth 2026 that enable lock nut member 2006 to function as described herein.

Figure 73:
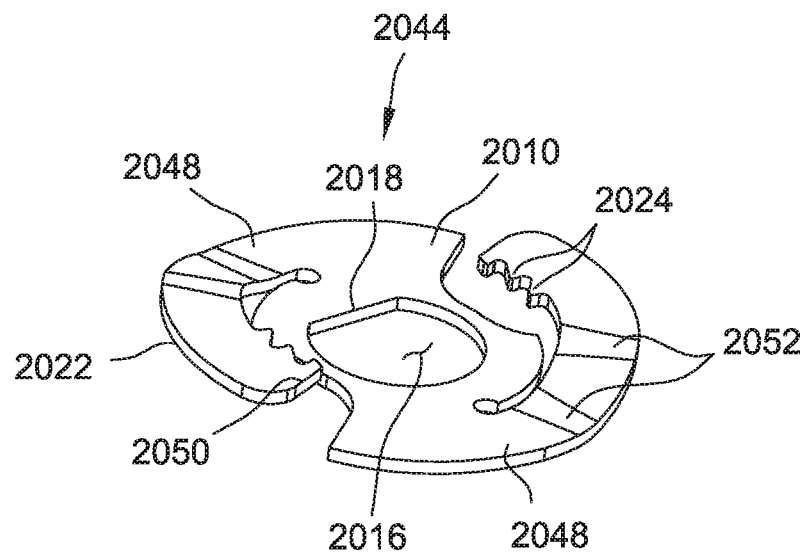
FIG. 73 is a perspective view of an exemplary embodiment of a lock washer for use with the fastener assembly shown in FIG. 66.
Figure 74:
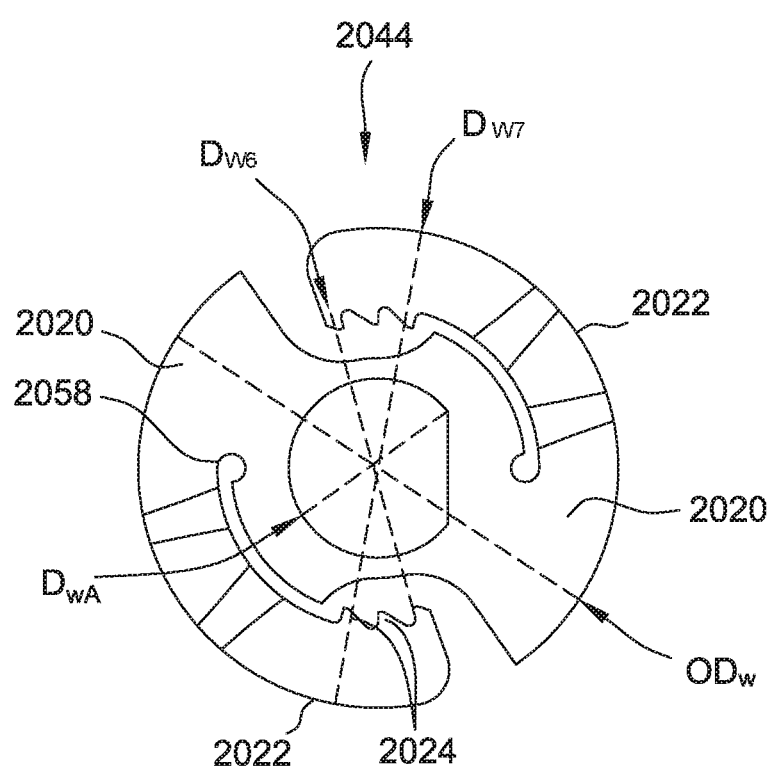
FIG. 74 is a top view of the lock washer shown in FIG. 73.
Figure 75:
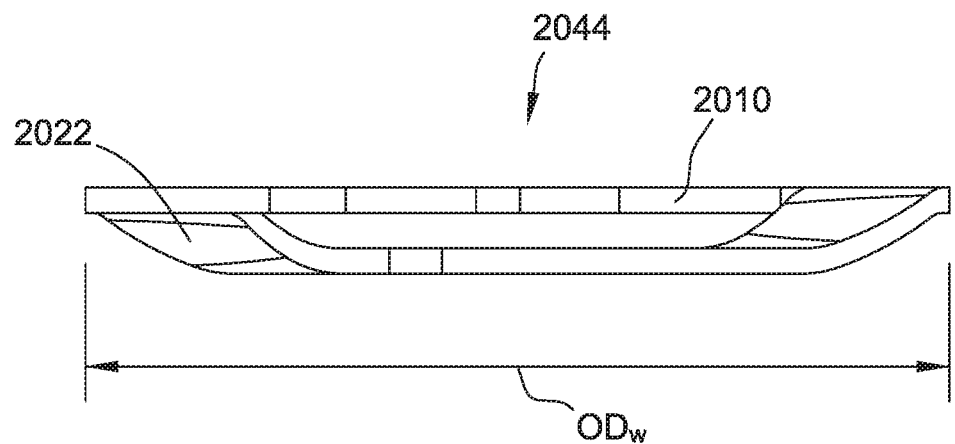
FIG. 75 is a first side view of the lock washer shown in FIG. 73.
Figure 76:
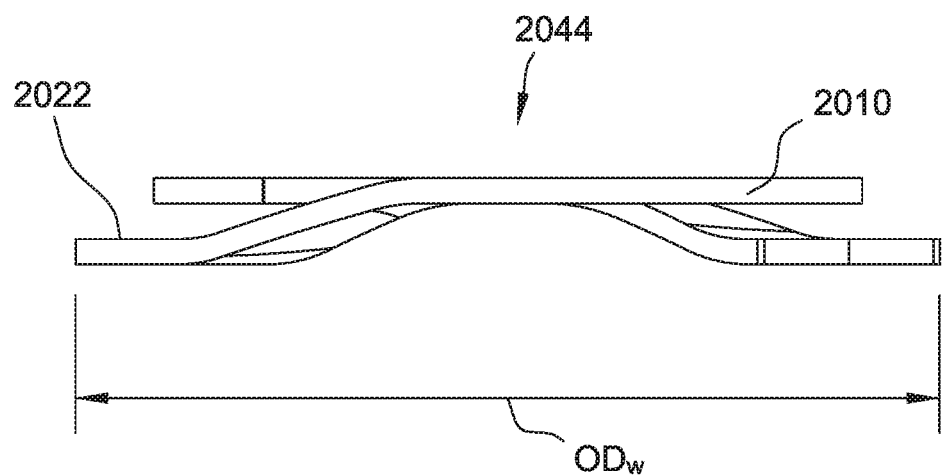
FIG. 76 is a second side view of the lock washer shown in FIG. 73.

FIG. 73 is a perspective view of an exemplary embodiment of a lock washer 2044 for use with fastener assembly 2000 (shown in FIGS. 66-68). With reference to FIGS. 73-76, lock washer 2044 includes a base portion 2020 defining an axial aperture 2016 therethrough and at least one tab 2022. Axial aperture 2016 is sized to facilitate freely sliding lock washer 2044 onto threaded body portion 2010 of threaded member 2002. As such, axial aperture 2016 has a diameter "$D_{wA}$" slightly greater than diameter "D" (shown in FIG. 69) of threaded body portion 2010 (shown in FIG. 69). Axial aperture 2016 also includes an anti-rotation structure 2018 configured to engage anti-rotation feature 2012 (shown in FIG. 69) of threaded member 2002 (shown in FIG. 69). It is contemplated that anti-rotation structure 2018 includes, for example, and without limitation, a finger, member or any other component configured to engage anti-rotation feature 2012, for example, flats, notches, or grooves. In the exemplary embodiment, anti-rotation structure 2018 includes a pair of opposing flat inner surfaces sized and shaped to correspond to the pair of opposing longitudinally extending anti-rotation features 2012 (shown in FIG. 69) of threaded body portion 2010 (shown in FIG. 69).

In the exemplary embodiment, lock washer 2044 includes a pair of opposing tabs 2022 extending upward from base portion 2020. In particular, the outer edge of tabs 2022 extend along a circumference defined by boundary diameter "$D_{w7}$". In addition, tabs 2022 extend from proximal end 2048 to free end 2050 at an angle relative to an upper surface of base portion 2020. In the exemplary embodiment, base portion 2020 is circular and has an outer diameter or width "$OD_w$". The boundary diameter "$D_{w7}$" is equivalent to the outer diameter, "$OD_w$". In alternative embodiments, lock washer 2044 has any base portion 2020 that enables lock washer 2044 to function as described herein. In alternative embodiments, the pair of opposing tabs 2022 and base portion 2020 are at least two separate parts that may be releasably coupled together. In some configurations the opposing tabs 2022 can be rigidly fixed to the base portion 2020. In alternative embodiments, the opposing tabs 2022 and base portion 2020 can be configured in any manner that enable lock washer 2044 to function as described herein.

Also, in the exemplary embodiment, each tab 2022 includes a proximal end 2048 coupled to base portion 2020 and a free end 2050 opposite proximal end 2048. Each free end 2050 includes a plurality of edge teeth 2024 configured to engage with corresponding mating radially extending locking teeth 2026 (shown in FIG. 70) of lock nut member 2006 (shown in FIG. 70). As such, inner boundary diameter "$D_{W6}$" is defined between the center of lock washer 2044 and an inner edge of teeth 2026 of lock washer 2044. The inner boundary diameter "$D_{W6}$" of tabs 2022 is substantially equal to or slightly less than diameter or width "$OD_n$" of lock nut member 2006 (shown in FIG. 70) or any other diameter that enables teeth 2024 to engage teeth 2026 (shown in FIG. 70). In addition, angle "α" may be any angle that enables lock washer 2044 to engage with locking teeth 2026 of lock nut member 2006. In the exemplary embodiment, each tab 2022 has at least one bend 2052 such that edge teeth 2024 are oriented in a direction different from the direction at which tab 2022 extends from base portion 2020. For example, in the exemplary embodiment, each tab 2022 includes two 90° horizontal bends or curves 2052 such that edge teeth 2024 face inward toward axial aperture 2016 and threaded member 2002 (shown in FIG. 69). In addition, in the exemplary embodiment, tab 2022 includes at least one vertical bend 2052 in the vertical or axial direction such that edge teeth 2024 are in a different plane than base portion 2020. In further embodiments, tab 2022 includes an 180° bend. In alternative embodiments, tabs 2022 have any configuration that enable lock washer 2044 to function as described herein.

Figure 77:
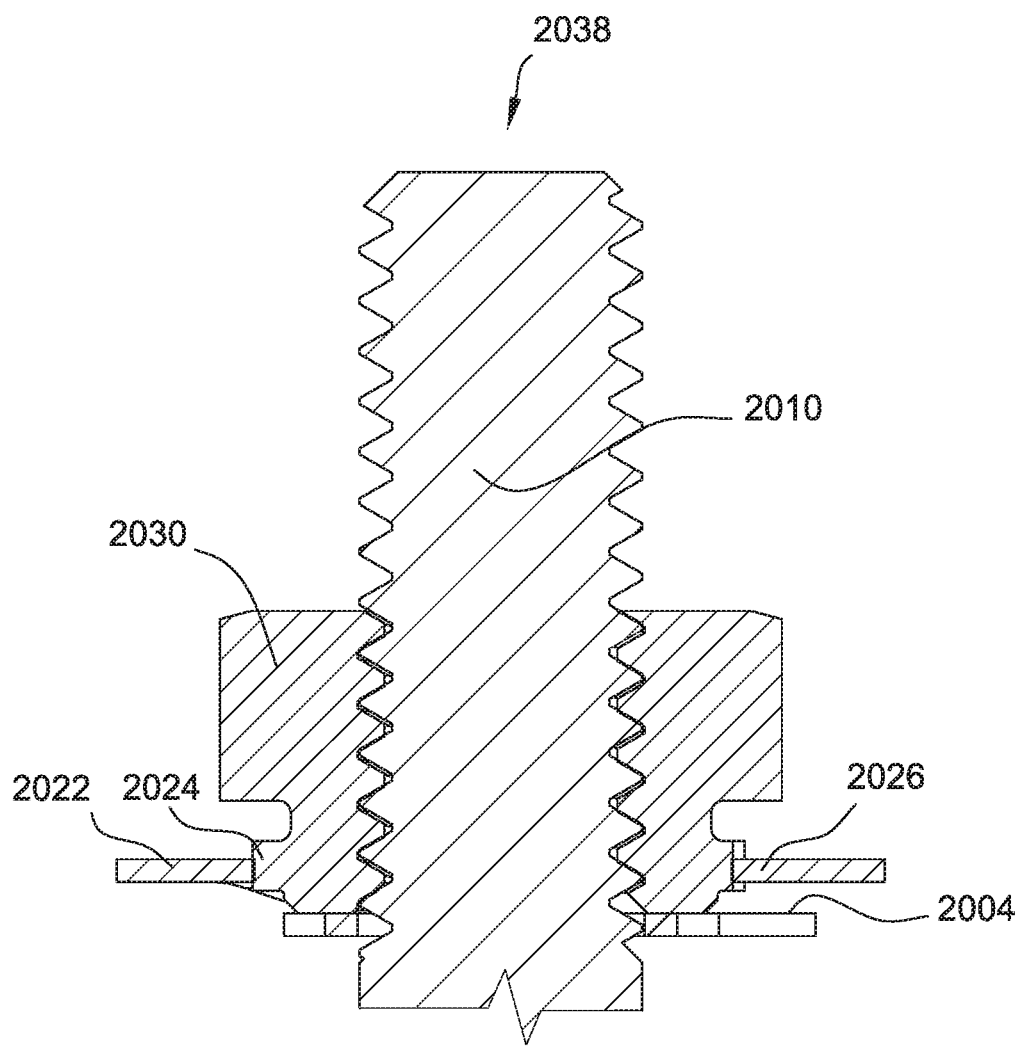
FIG. 77 is a sectional view of the fastener assembly shown in FIG. 66, including the lock washer engaged with the lock member and rotationally fixed with respect to the bolt.

FIG. 77 is a sectional view of fastener assembly 2000 showing lock washer 2044 in a first orientation 2038, where lock nut member 2006 is engaged with lock washer 2044 and rotationally fixed. Lock nut member 2006 is configured to be threadably received by threaded member 2002 over threaded body portion 2010 and is rotationally free or rotationally fixed relative to threaded member 2002 depending upon whether lock nut member 2006 is engaged with or disengaged from lock washer 2044. In the exemplary embodiment, locking teeth 2026 of flange 2032 are configured to be engaged by inner edge teeth 2024 of lock washer 2044. Inner edge teeth 2024 formed in extending flange 2032 of lock washer 2044 engage (i.e., extend into) with locking teeth 2026 of the lock nut member 2006 in first orientation 2038. Engaging edge teeth 2024 with locking teeth 2026 facilitates rotationally fixing lock nut member 2006 relative to lock washer 2044. In addition, lock washer 2044 is rotationally fixed to threaded member 2002 via the engagement of anti-rotation structures 2018 to the anti-rotation features 2012 of threaded body portion 2010 of threaded member 2002. Accordingly, lock nut member 2006 is rotationally fixed relative to threaded member 2002 in first orientation 2038 of fastener assembly 2000.

In the exemplary embodiment, "$D_{w7}$" is greater than "$D_{W6}$" such that tabs 2022 extend radially beyond the extents of lock nut member 2006. As a result, a tool such as tool 108 (shown in FIG. 10) is able to provide an axial force "F" to the tabs 2022. Moreover, fastener assembly 2000 is able to be unlocked using standard tools because of the configuration of lock washer 2044 and lock nut member 2006. An applied axial force on tabs 2022 facilitates bending or flexing tabs 2022 to be displaced in a downward direction. Tabs 2022 in a second orientation are offset from first orientation 2038 by an offset distance of sufficient magnitude to facilitate disengaging edge teeth 2024 from locking teeth 2026 of lock nut member 2006, thereby enabling lock nut member 2006 to freely rotate relative to lock washer 2044 and threaded member 2002.

In the exemplary embodiment, threaded member 2002, lock washer 2044, and lock nut member 2006 are fabricated from a metal, for example, and without limitation, steel, aluminum, titanium, or a superalloy. Alternatively, threaded member 2002, lock washer 2004, and lock nut member 2006 are fabricated from any material that enables fastener assembly 2000 to function as described herein, such as, without limitation, composite materials, resins, fiber reinforced resins, plastics, and fiber reinforced plastics.

Moreover, in the exemplary embodiment, lock washer 2044 (shown in FIG. 73), include base portion 2020 and tabs 2022 that are joined, i.e., permanently connected, such that lock washer 2044 are each a single piece. Specifically, lock washer 2044 may be stamped from sheets of precursor material, e.g., sheet metal. In the manufacturing process, lock washer 2044 are cut from the sheet and tabs 2022 are bent relative to base portion 2020 to provide the desired shape of lock washer 2044 without adding material. Accordingly, the shape and size of base portion 2020 and tabs 2022 allow lock washer 2044 to be stamped and reduce the time and cost required to manufacture lock washer 2044. In alternative embodiments, lock washer 2044 may be constructed in any manner that enables lock washer 2044 to function as described herein.

For example, a method of manufacturing fastener assembly 2000 (shown in FIG. 68) includes providing threaded member 2002 (shown in FIG. 68) and lock nut 2004 (shown in FIG. 70). An outline or footprint of base portion 2020 of lock washer 2044 is cut from a sheet of precursor material. In some embodiments, a plurality of lock washers 2004 are cut from a single sheet. In addition, any required openings and cuts are formed in lock washer 2044. For example, aperture 2016 and the outline of tabs 2022 are formed by cuts in the precursor sheet. The precursor sheet is substantially flat. To shape lock washer 2044, tabs 2022 are bent relative to base portion 2020 to a desired angle and position. A plurality of bends 2052 in tabs 2022 may be formed to provide the desired orientation of tabs 2022 and teeth 2024. In some embodiments, lock washer 2044 is formed by a single press stage, i.e., all bending and shaping of lock washer 2044 is performed simultaneously. In other embodiments, lock washer 2044 is formed using multiple stages of progressive die and each press stage partially shapes lock washer 2044. After the stamping process, lock washer 2044 is positionable on threaded member 2002 (shown in FIG. 68) and configured to engage lock nut 2004 (shown in FIG. 70). In alternative embodiments, fastener assembly 2000 (shown in FIG. 68) is formed in any manner that enables fastener assembly 2000 to function as described herein. For example, in some embodiments, lock washers 2044 is shaped by laser cutting, water jet cutting, and/or any other process for shaping a blank. In such embodiments, bends may be formed after the cutting or other shaping process is at least partially completed.

Figure 78:
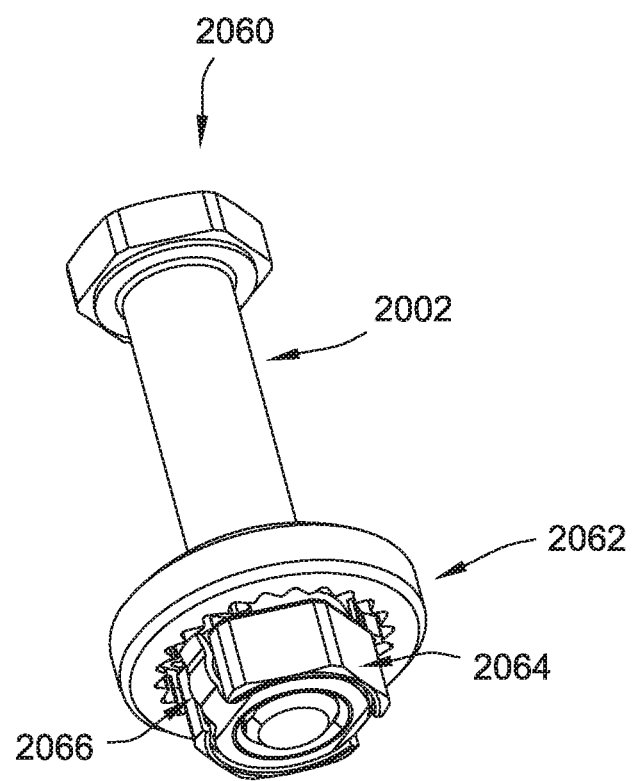
FIG. 78 is a perspective view of an exemplary embodiment of a fastener assembly constructed in accordance with the present disclosure, showing a nut, a lock member, a lock washer, and a threaded bolt of the fastener assembly.
Figure 79:
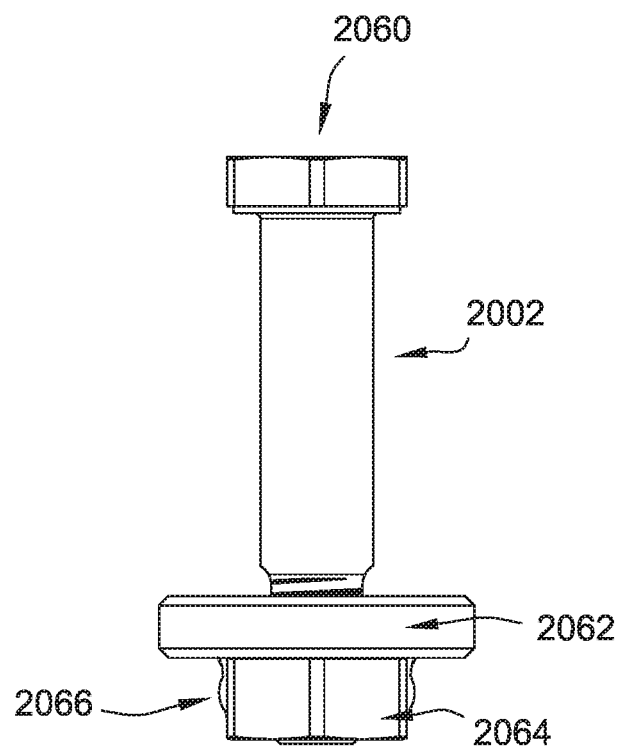
FIG. 79 is a side view of the fastener assembly shown in FIG. 78.
Figure 80:
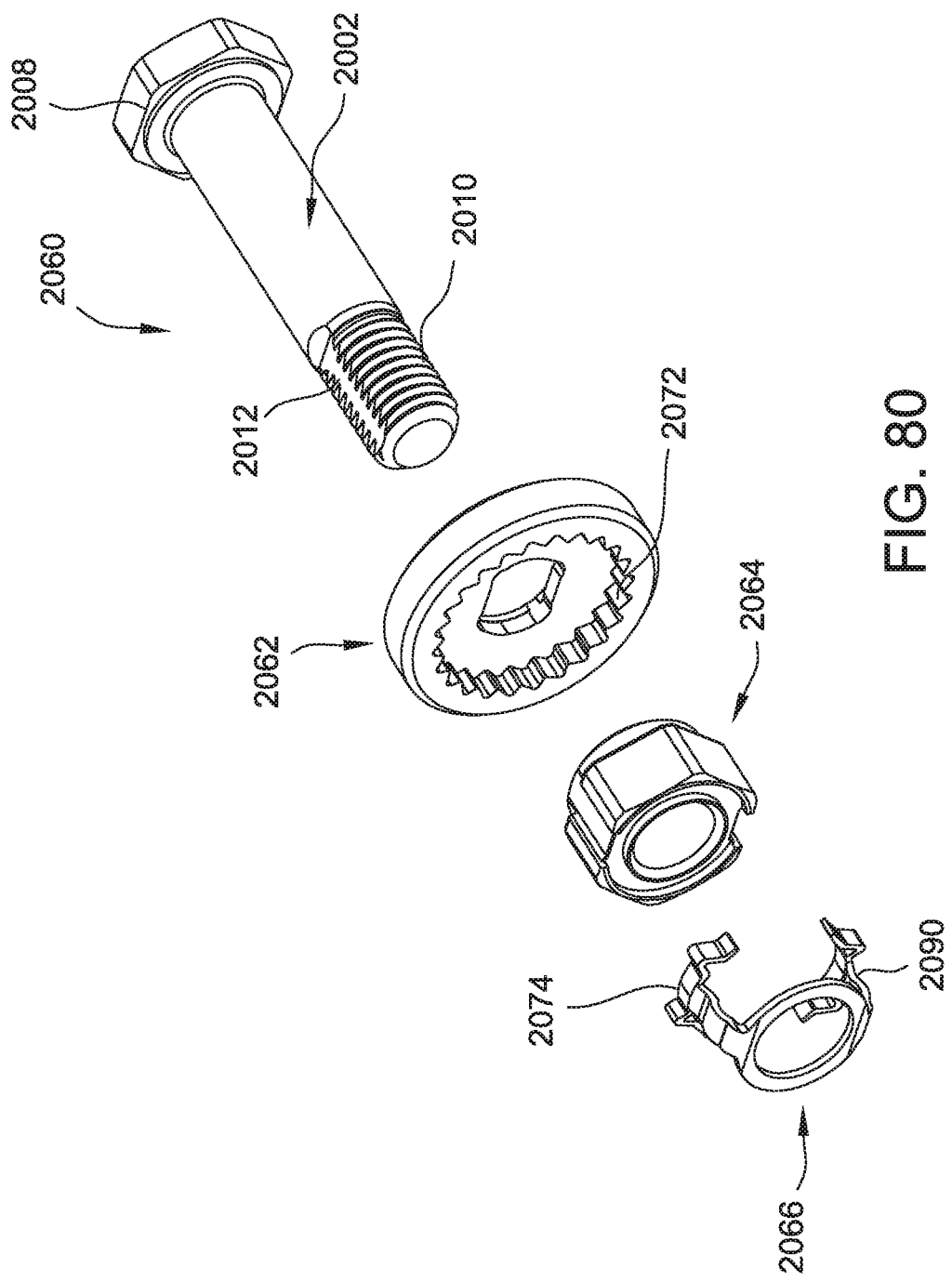
FIG. 80 is an exploded perspective view of the fastener assembly shown in FIG. 79.

FIG. 78 is a perspective view of another exemplary embodiment of a fastener assembly 2060. FIG. 79 is a side view of fastener assembly 2060. FIG. 80 is an exploded perspective view of fastener assembly 2060. In the exemplary embodiment, fastener assembly 2060 includes threaded member 2002, a lock washer 2062, a lock nut 2064, and a lock member 2066. Lock washer 2062 is configured to slidably couple to anti-rotation features 2012 of threaded body portion 2010 for axial movement along threaded body portion 2010. Anti-rotation features 2012 facilitate rotationally fixing lock washer 2062 relative to threaded member 2002. Lock washer 2062 includes a central axial aperture 2016 therethrough. Axial aperture 2016 is sized to facilitate freely sliding lock washer 2062 onto threaded body portion 2010 of threaded member 2002. As such, axial aperture 2016 has a diameter "$D_{WA}$" slightly greater than diameter "D" of threaded body portion 2010. Axial aperture 2016 also includes an anti-rotation structure 2018 configured to engage anti-rotation feature 2012 of threaded member 2002. It is contemplated that anti-rotation structure 2018 includes, for example, and without limitation, a finger, member, or any other component configured to engage anti-rotation feature 2012, for example, flats, notches, or grooves. In the exemplary embodiment, anti-rotation structure 2018 includes a pair of opposing flat inner surfaces sized and shaped to correspond to the pair of opposing longitudinally extending anti-rotation features 2012 of threaded body portion 2010. Anti-rotation features 2012 slidably couple with anti-rotation structures 2018 of lock washer 2062 to rotationally fix lock washer 2062 when threaded body portion 2010 is inserted in axial aperture 2016. As such, lock washer 2062 moves freely along threaded body portion 2010 in the axial direction.

Figure 81:
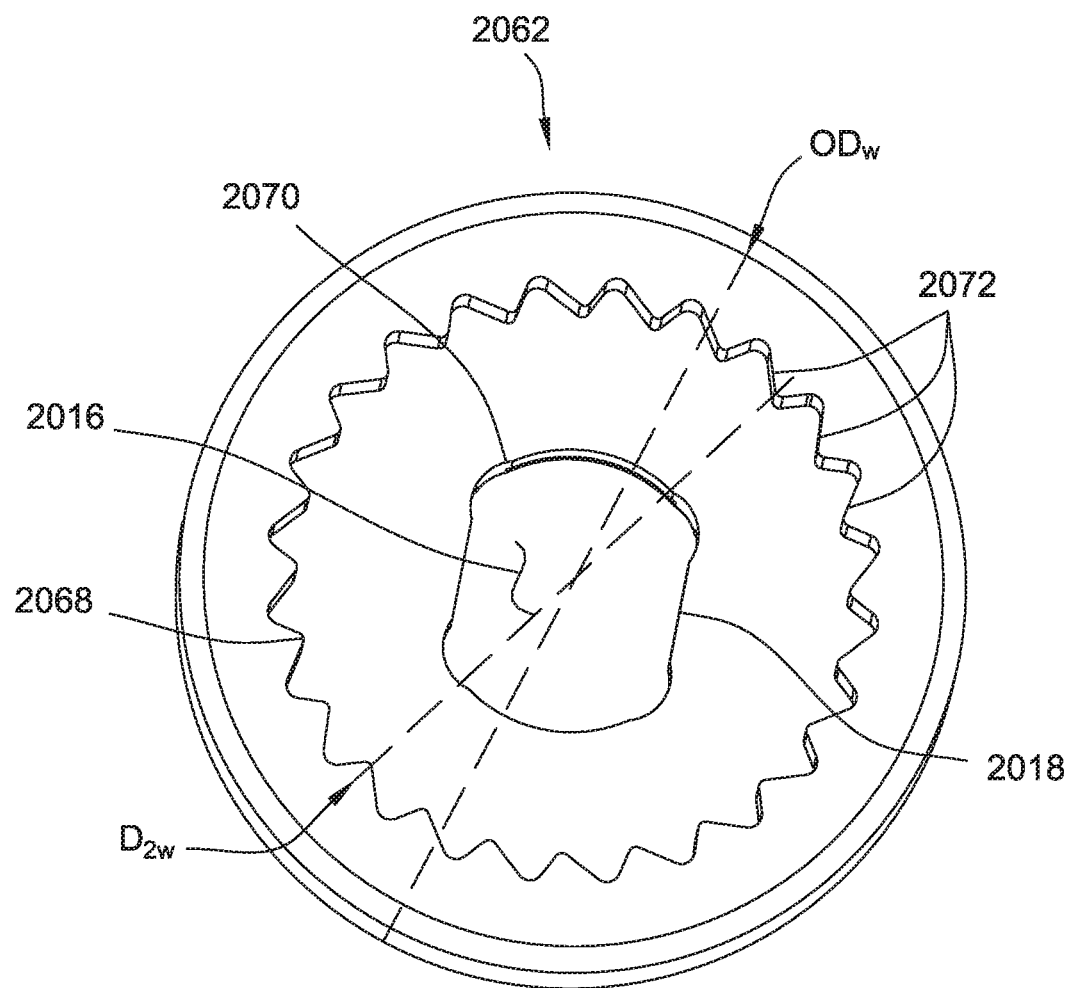
FIG. 81 is a bottom view of the lock washer of the fastener assembly shown in FIG. 78.
Figure 82:
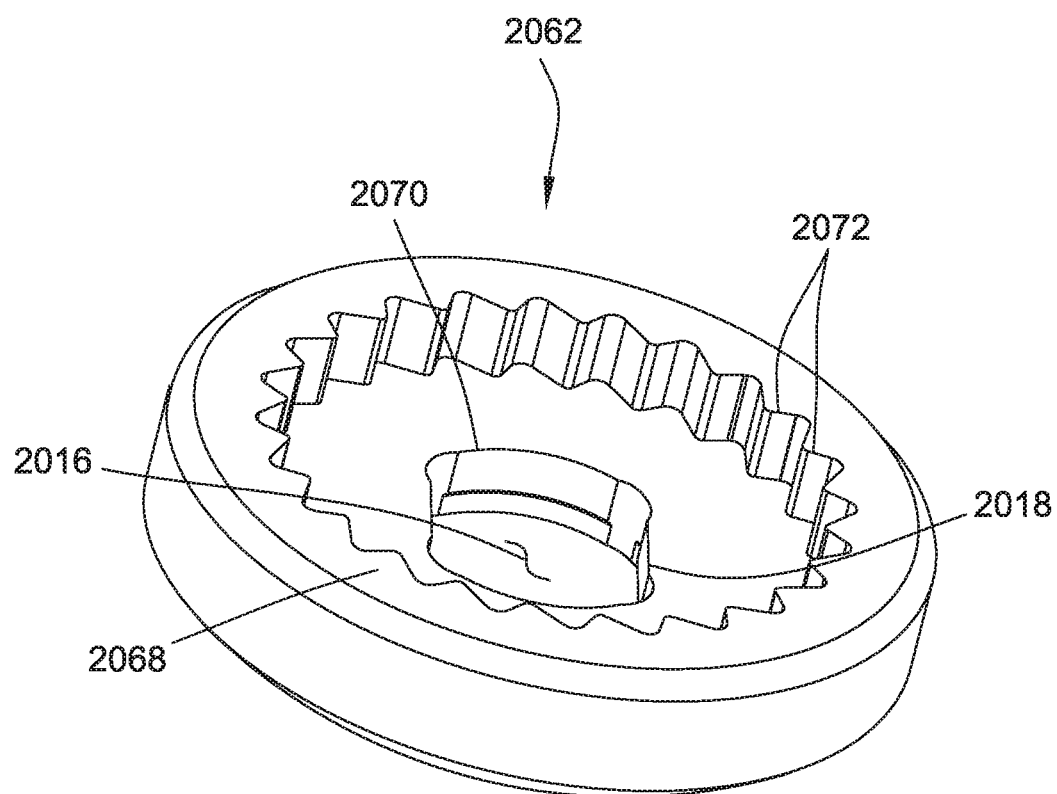
FIG. 82 is a perspective view of the lock washer shown in FIG. 78.

With reference to FIGS. 81 and 82, in the exemplary embodiment, lock washer 2062 includes an outer portion 2068 having a diameter or width "$OD_W$." Within outer portion 2068, for any number of smaller radial diameters, concentric with the outer diameter, is a recessed center portion 2070 of any depth of H. The circumference of recessed center portion 2070 is a plurality of internal teeth 2072. Internal teeth 2072 are sized and shaped to engage with tabs 2074 of lock member 2066 to aid in prevention of rotation of lock nut 2064. Recessed center portion 2070 is configured to receive an extrusion 2076 of lock nut 2064. In the exemplary embodiment, recessed center portion 2070 and extrusion 2076 are circular. In other embodiments, recess 2070 and extrusion 2076 are shapes other than circles. In alternative embodiments, lock washer 2062 has any configuration that enables fastener assembly 2060 (shown in FIG. 80) to function as described herein.

Figure 83:
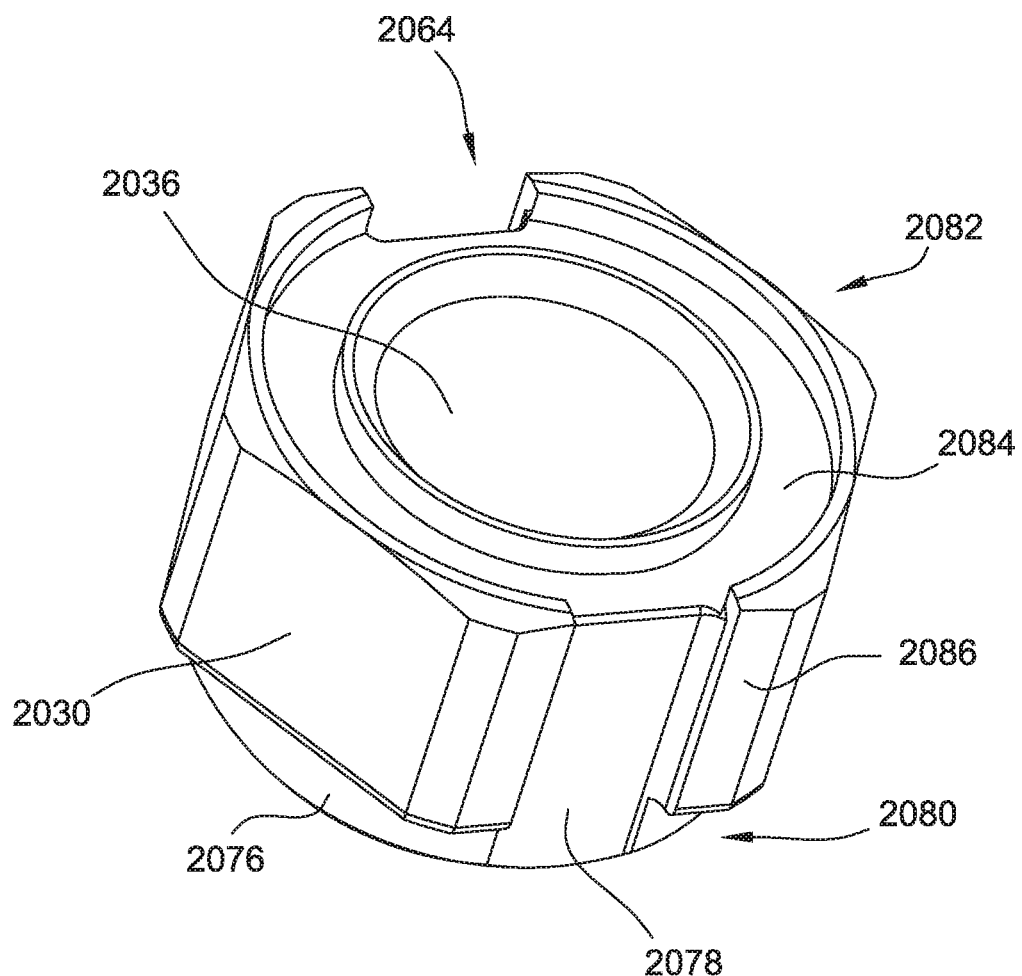
FIG. 83 is a perspective view of the nut of the fastener assembly shown in FIG. 78.
Figure 84:
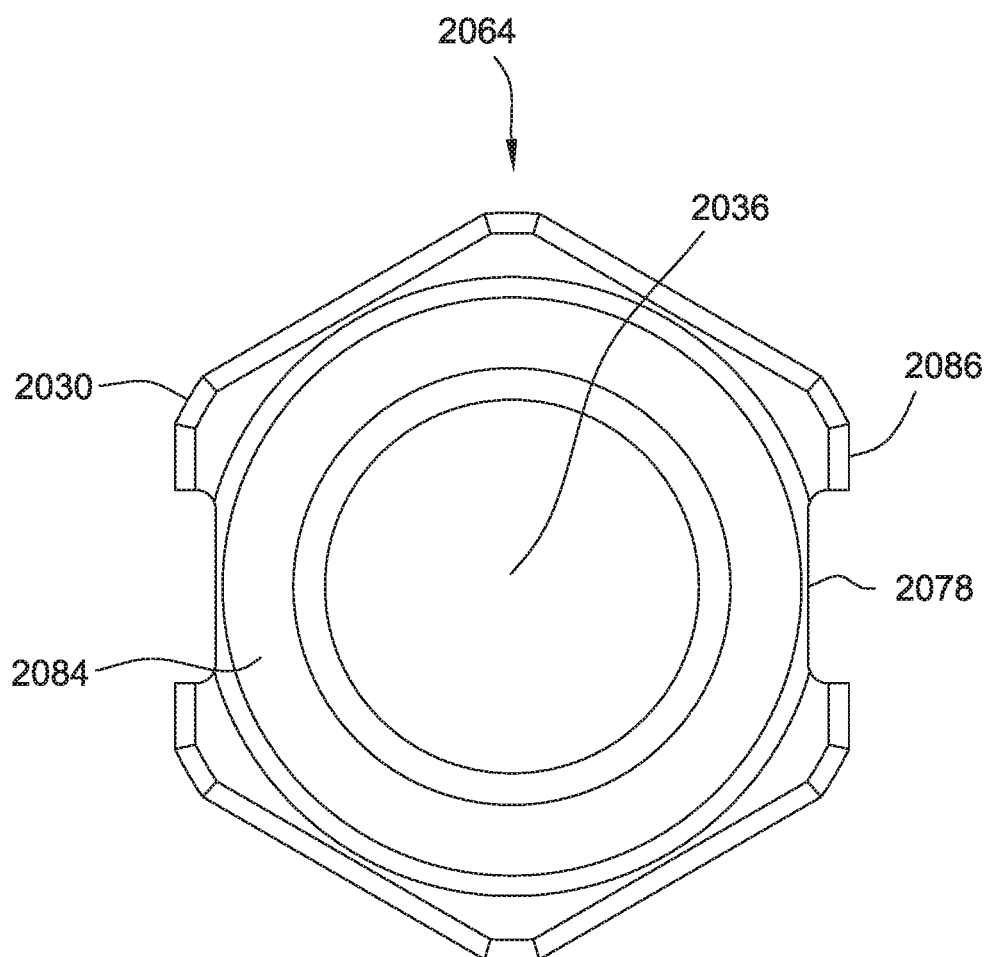
FIG. 84 is a bottom view of the nut shown in FIG. 83.
Figure 85:
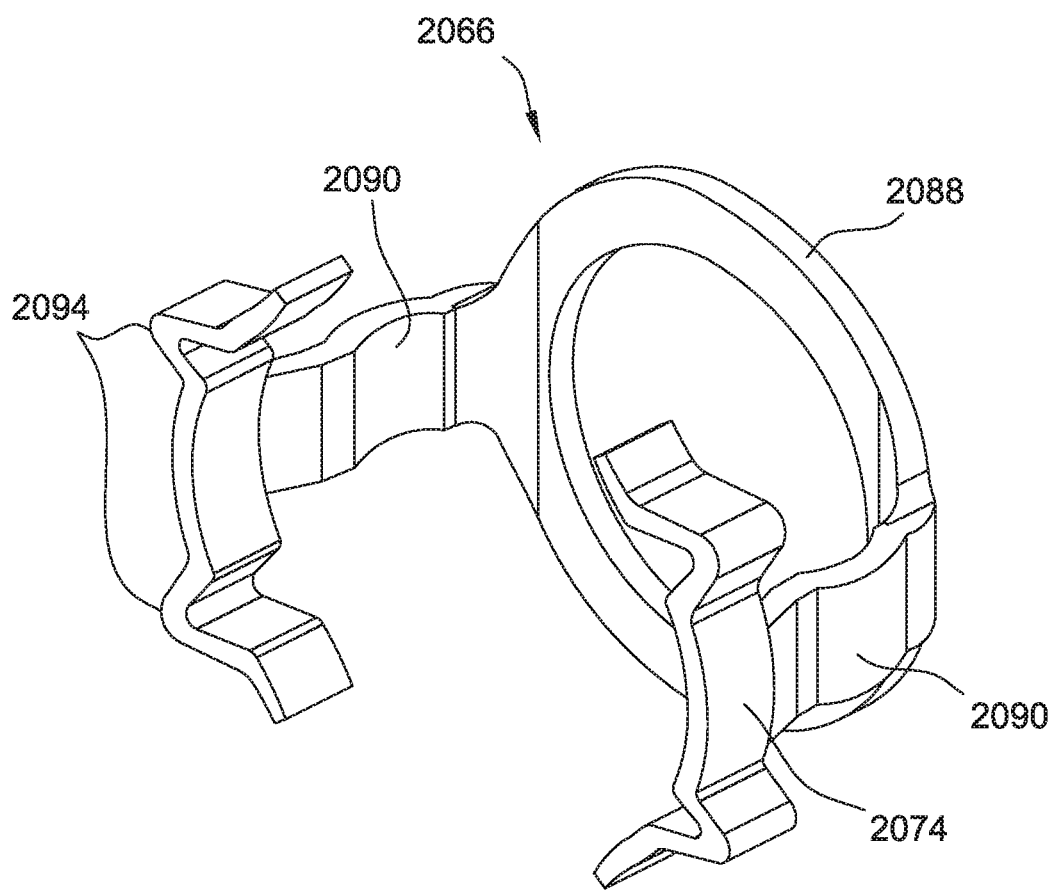
FIG. 85 is a lower perspective view of the lock member of the fastener assembly shown in FIG. 78.
Figure 86:
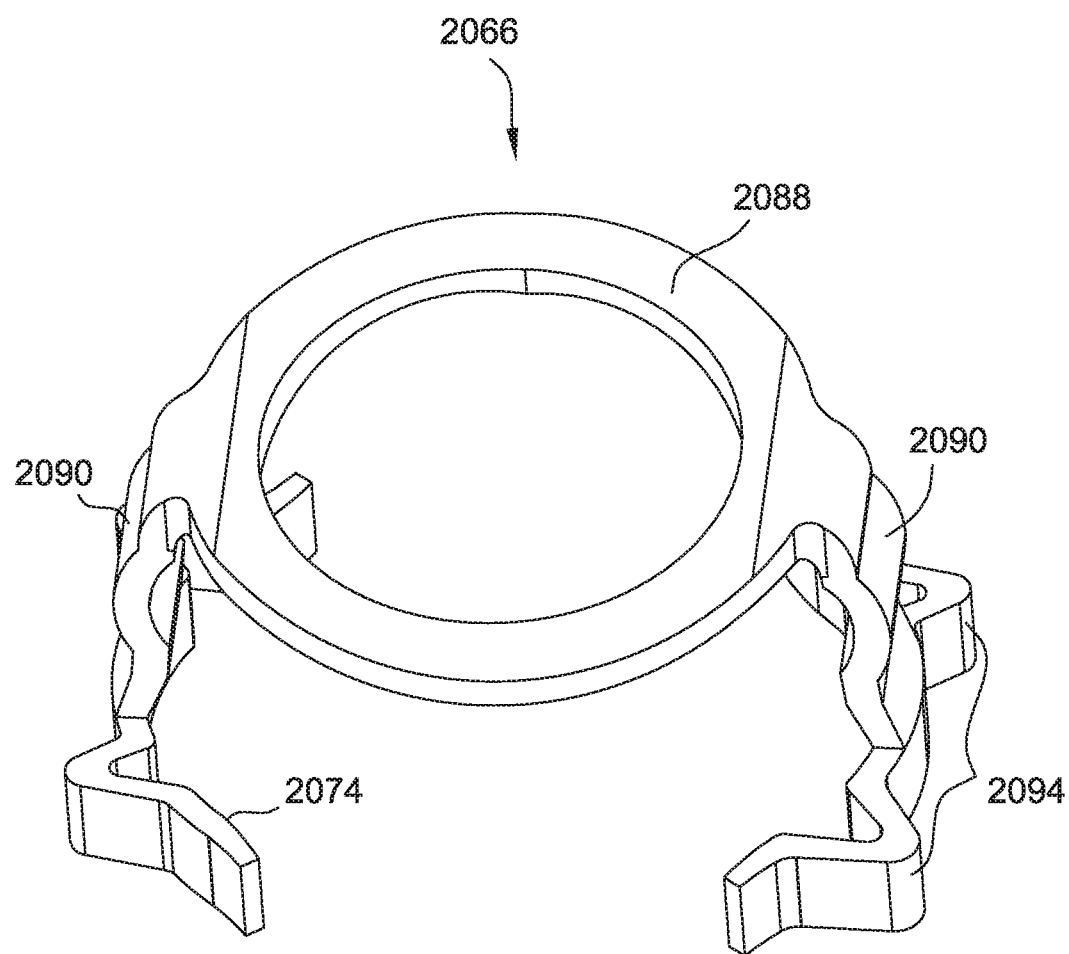
FIG. 86 is an upper perspective view of the lock member shown in FIG. 85.
Figure 87:
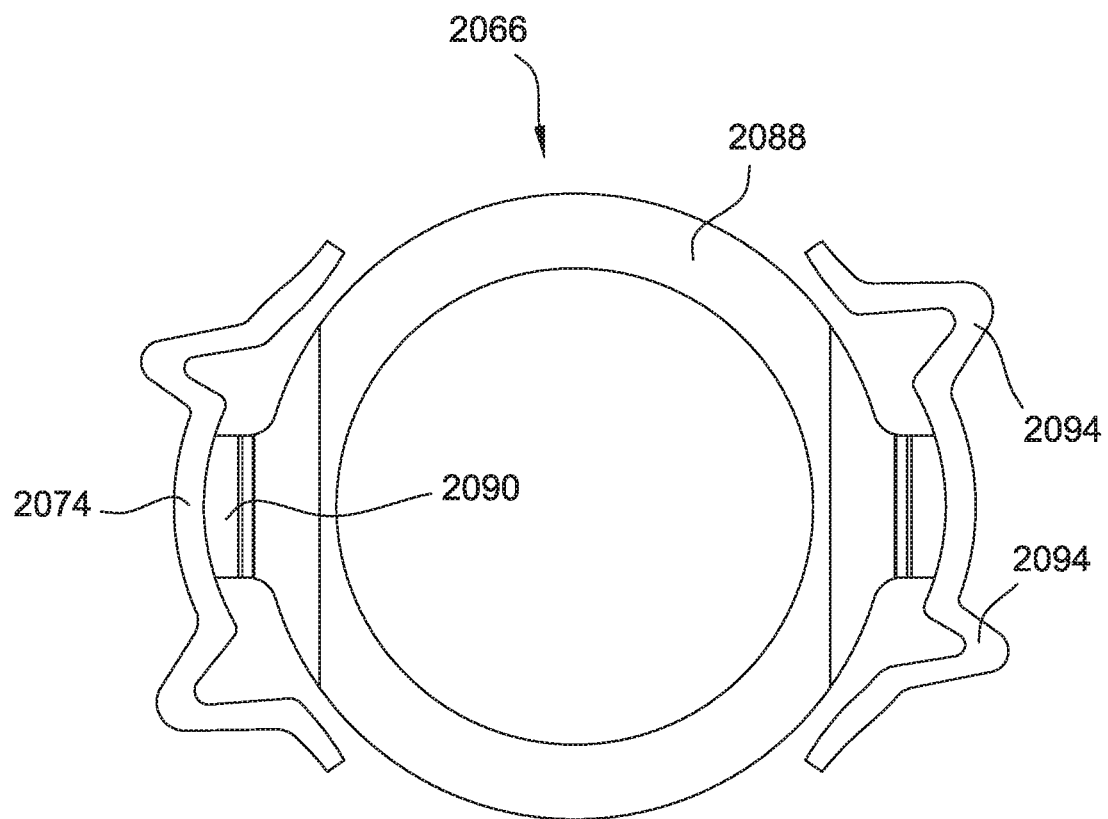
FIG. 87 is a bottom view of the lock member shown in FIG. 85.
Figure 88:
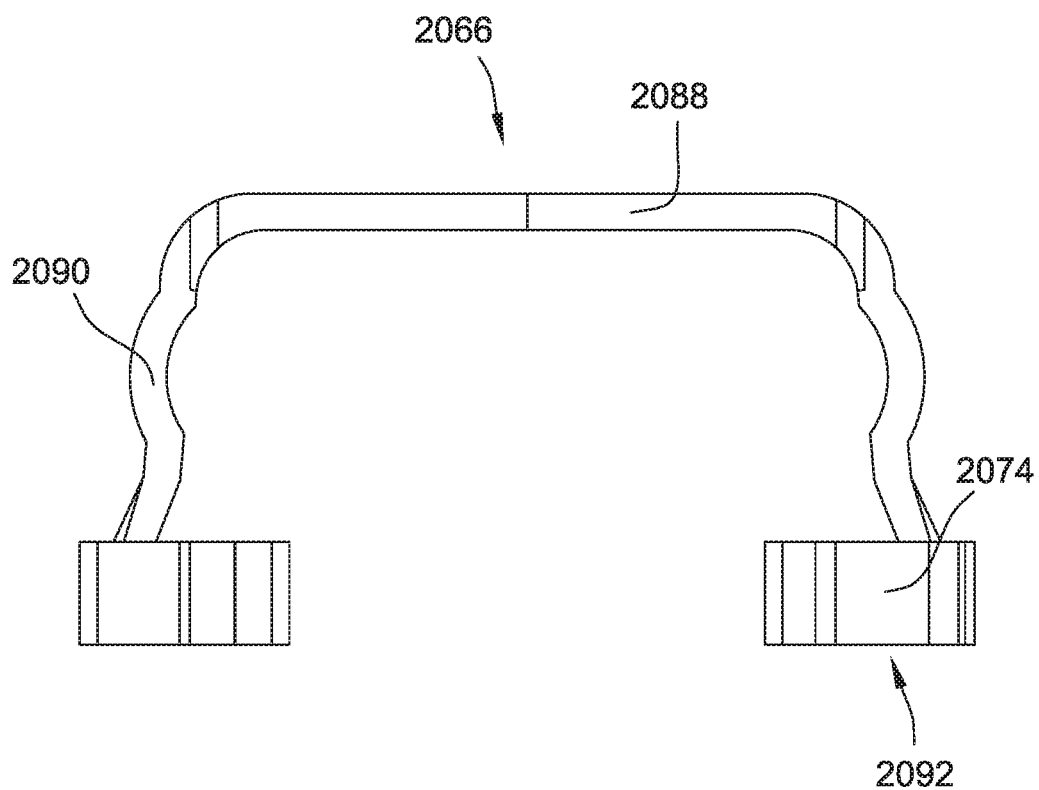
FIG. 88 is a side view of the lock member shown in FIG. 85.

With reference to FIGS. 83 and 84, lock nut 2064 includes a body 2030, a plurality of longitudinal side grooves 2078, a proximal end 2080 configured with an extrusion 2076 and a distal end 2082 configured with a groove 2084. In the exemplary embodiment, pluralities of side grooves 2084 are defined by a peripheral or bearing surface 2086 of lock nut 2064 and have depths H. In the exemplary embodiment, lock nut 2064 includes a pair of side grooves 2078 on opposed sides of body 2030 that extend axially from distal end 2082 to proximal end 2080. In addition, in the exemplary embodiment, body 2030 includes a threaded bore 2036 extending axially through lock nut 2064. Extrusion 2076 on proximal end 2080 of lock nut 2064 is configured to fit within recessed center portion 2070 on lock washer 2062. Groove 2084 on distal end 2082 is configured to receive a base 2088 of lock member 2066. Body 2030 is formed as a hexagonal-shaped body, although other configurations of body 2030 are contemplated. In alternative embodiments, lock nut 2064 has any configuration that enables fastener assembly 2060 (shown in FIG. 80) to function as described herein.

With reference to FIGS. 85-88, lock member 2066, includes a base 2088, a pair of arms 2090, and tabs 2074. Base 2088 of lock member 2066 is shaped to fit within groove 2084 on lock nut 2064. For example, both base 2088 and groove 2084 are annular and have the same diameter. Arms 2090 extend from base 2088 and have width H and length L. The dimension of arms 2090 are configured to fit within the side grooves 2078 of the lock nut 2064. Extending perpendicular to arms 2090 at a free end 2092 (shown in FIG. 88) of lock member 2066 are a plurality of tabs 2074. Each end of the tab 2074 is configured to include at least one detent 2094. Detents 2094 on each tab 2074 extend radially from arms 2090 and are configured to engage with internal teeth 2072 (shown in FIG. 82) of lock washer 2062 (shown in FIG. 81). Engaging extending detents 2094 with internal teeth 2072 and fitting arms 2090 within side grooves 2078 of lock nut 2064 facilitates rotationally fixing lock nut 2064 relative to lock washer 2062.

In the exemplary embodiment, lock member 2066 is formed as a single piece and is manufactured using a stamping process. Specifically, base 2088, arms 2090, and tabs 2074 are cut from a sheet of material and arms 2090 and tabs 2074 are bent to provide the desired shape of lock member 2066. In alternative embodiments, lock member 2066 is constructed in any manner that enables lock member 2066 to function as described herein.

For example, a method of manufacturing fastener assembly 2060 (shown in FIG. 78) includes providing threaded member 2002 (shown in FIG. 69), lock washer 2062 (shown in FIG. 81), and lock nut 2064 (shown in FIG. 83). An outline or footprint of lock member 2066 is cut from a sheet of precursor material. In some embodiments, a plurality of lock members 2066 are cut from a single sheet or strip. In addition, any required openings or cuts are formed in lock member 2066. For example, the outline of base 2088, arms 2090, and tabs 2074 are cut. To shape lock member 2066, arms 2090 are bent relative to base 2088 to a desired angle and position. A plurality of bends in arms 2090 may be formed to provide the desired orientation of arms 2090. In addition, tabs 2074 are bent relative to arms 2090 into a desired orientation. Also, tabs 2074 are crimped to provide detents 2094. In some embodiments, lock member 2066 is formed in a single press stage, i.e., all bending and shaping of lock member 2066 is performed simultaneously. In other embodiments, lock member 2066 is formed in a multiple stages of progressive die and each press partially shapes lock member 2066. After the stamping process, lock member 2066 is coupled to lock nut 2064 (shown in FIG. 83) such that lock nut 2066 and lock member 2066 are positionable on threaded member 2002 (shown in FIG. 69) and configured to engage lock washer 2062 (shown in FIG. 81). In alternative embodiments, fastener assembly 2060 (shown in FIG. 80) is formed in any manner that enables fastener assembly 2060 to function as described herein.

Figure 89:
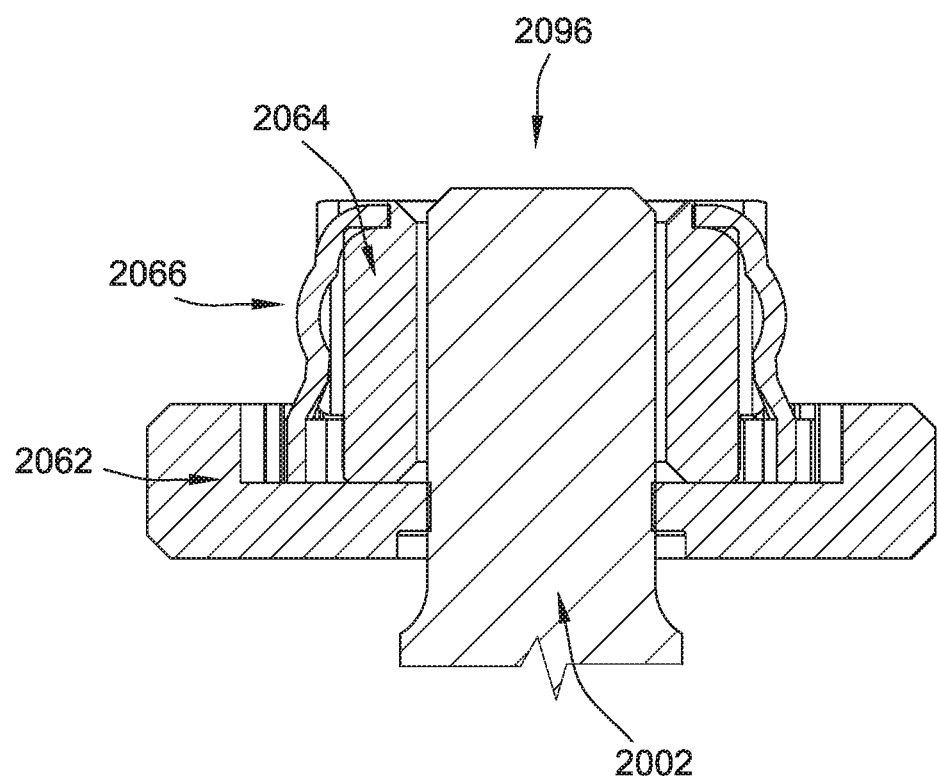
FIG. 89 is a sectional view of the fastener assembly shown in FIG. 78, including the washer engaged with the lock member and rotationally fixed with respect to the threaded bolt.
Figure 90:
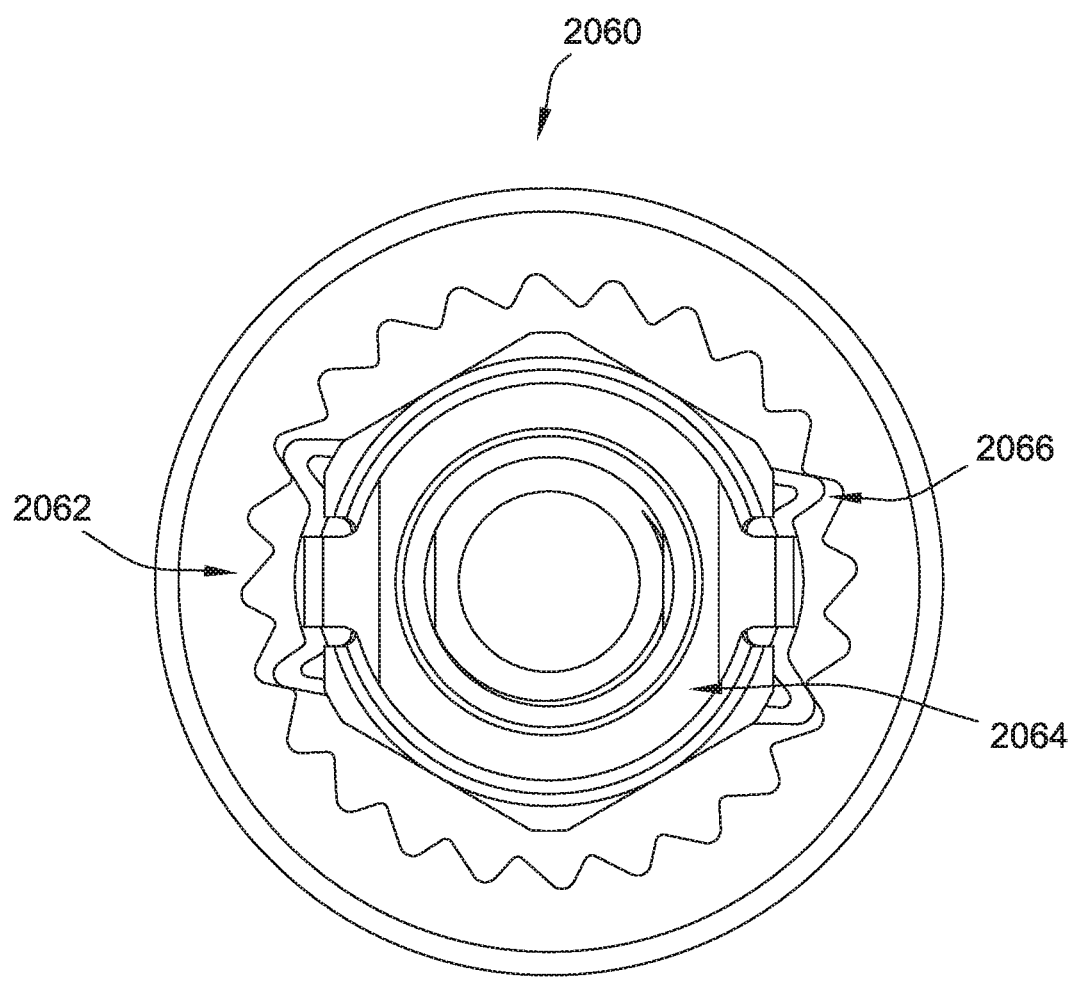
FIG. 90 is a bottom view of the fastener assembly shown in FIG. 78.

FIG. 89 is a sectional view of fastener assembly 2060 showing lock nut 2064 engaged with lock washer 2062 and lock member 2066 and rotationally fixed to threaded member 2002. Lock nut 2064 is configured to be threadably received by threaded member 2002 over threaded body portion 2010 and is rotationally free or rotationally fixed relative to threaded member 2002 depending upon whether lock nut 2064 is engaged with or disengaged from lock washer 2062. Extrusion 2076 on locking nut 2064 extends into recessed center portion 2070 of lock washer 2062. Arms 2090 of lock member 2066 are fit into side groves 2078 of lock nut 2064. Detents 2094 of lock member 2066 are inserted between the outer edge of extrusion 2076 of locking nut 2064 and internal teeth 2072 of lock washer 2062. Engaging detents 2094 with internal teeth 2072 and engaging arms 2090 with side grooves 2078 facilitates rotational fixation of lock nut 2064 with lock washer 2062. In addition, lock washer 2062 is rotationally fixed to threaded member 2002. Accordingly, lock nut 2064 is rotationally fixed relative to the threaded member 2002 in locked orientation 2096 of fastener assembly 2060.

In the exemplary embodiment, threaded member 2002, lock washer 2062, lock member 2066 and lock nut 2064 are fabricated from a metal, for example, and without limitation, steel, aluminum, titanium, or a superalloy. Alternatively, threaded member 2002, lock washer 2062, lock member 2066 and lock nut 2064 are fabricated from any material that enables fastener assembly 2060 to function as described herein, such as, without limitation, composite materials, resins, fiber reinforced resins, plastics, and fiber reinforced plastics.

In some embodiments, the lock washer may be formed as two or more separate pieces. For example, in some embodiments, the lock washer includes a base portion and an upper portion. The upper portion may be rigidly fixed to the base portion at a plurality of connection tabs or in any other suitable manner. The base portion and upper portion can be joined by clinching, welding and/or by rivets. At least one arm may extend from the upper portion and be configured to engage a lock nut and/or lock member. In addition, in some embodiments, the at least one arm includes at least one vertical bend in the vertical or axial direction such that edge teeth are in a different plane than base portion and/or the upper portion. In further embodiments, the arms may include a 45° bend. As a result, the lock washer provides a higher locking torque. In addition, the lock washer may have areas of differing thickness to provide increased strength or sturdiness such as in the base. Also, the different pieces may have different dimensions. For example, the base washer diameter can be larger without affecting the locking mechanism's diameter. In alternative embodiments, the arms may include any number of pieces that enable the lock washer to function as described herein.

In some embodiments, the fastener assemblies are assembled as a captive fastener assembly in which the threaded member, nut, lock member, and/or lock washer are coupled together and provided to a user as a single assembly. In such embodiments, the captive fastener assembly is ready for installation as a single unit without requiring additional components. Accordingly, the captive configuration simplifies installation and removal of the fastener assembly and reduces opportunities for damage by foreign objects.

The components as described herein provide locking and vibration resistant fastener assemblies. For example, as described in the embodiments herein, when the tool is removed from the associated fastener assembly, teeth on the lock nut again engage the locking apertures/teeth of the respective lock washer. When the teeth are engaged, the lock nut is positively locked in rotation due to the rotational locking relationship of the lock washer to the threaded member. When the teeth are disengaged from the locking apertures/teeth, the lock nut is a rotationally free running nut relative to the threaded member. As will be appreciated by those of skill in the art in view of the present disclosure, the arrangements shown in the figures facilitate preventing over deflection of the lock washers and/or lock members in response to the force "F" applied by tool.

Exemplary embodiments of systems and methods for rotationally locked fastener assemblies are described above. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

The fastening device technology described herein has unlimited application in industry and other uses. Particularly advantageous applications will involve use near motors or moving equipment in which severe vibration may cause loosening of traditional fasteners such as in automotive applications, aerospace applications, military applications, road and construction applications, oil and gas, and manufacturing machinery. The present fastening device technology is also well suited for medical applications such as attaching pedicle screws to spinal rods, attaching spinal plates and fracture plates, fixing artificial joints, like hips and knees, orthopedic and maxillofacial external fixator systems, and the like. In particular, those skilled in the art will readily appreciate that embodiments of the fastening device technology described herein can withstand high temperature applications, for example, they can withstand temperatures as high as the material they are fabricated from can tolerate, and are easily applied, removed and reused. In addition, it is contemplated that the tightening of a nut number on a bolt member can be blind. For example, instead of the head portions, flats defined on the bolt member can be held or otherwise fixed during tightening.

In addition, some embodiments described herein provide adjustable diameter locking and vibration resistant fastener assemblies. For example, as described in the embodiments herein, when a tool is removed from the associated fastener assembly, teeth on the lock member engage the notches of the respective lock washer. When the teeth are engaged, the lock nut is rotationally locked due to the rotational locking relationship of the lock washer to the lock member. When the tool is applied to the lock nut, the lock member is displaced radially inward to disengage the teeth from the notches. When the teeth are disengaged from the lock washer notches, the lock nut is rotationally free relative to the lock washer and the fitting body.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A fastener assembly comprising:
   a threaded member comprising a threaded body portion;
   a lock nut configured to threadably engage said threaded body portion;
   a first lock member including a plurality of radially extending ratchet teeth; and
   a second lock member comprising:
      a base portion defining an aperture extending therethrough, the aperture sized to receive said threaded body portion; and
      at least one tab extending axially from said base portion, said at least one tab having a proximal end joined to said base portion and a free end opposite said proximal end, wherein said second lock member further comprises a plurality of radially extending teeth on an inner side of said free end of said at least one tab, wherein said second lock member is positionable between a locked configuration in which said plurality of radially extending teeth are configured to engage said plurality of radially extending ratchet teeth and an unlocked configuration in which said plurality of radially extending teeth are spaced from said plurality of radially extending ratchet teeth, wherein said base portion and said at least one tab are a single piece.

2. The fastener assembly in accordance with claim 1, wherein said first lock member and said lock nut are integrally formed as a single piece.

3. The fastener assembly in accordance with claim 1, wherein said second lock member and said lock nut are integrally formed as a single piece.

4. The fastener assembly in accordance with claim 1, wherein said first lock member, said second lock member, and said lock nut are separate pieces.

5. The fastener assembly in accordance with claim 4, wherein said lock nut has a peripheral surface comprising an axially-extending slot defined therein, and wherein said second lock member is releasably coupled to said lock nut for rotation therewith, wherein said at least one tab at least partially engages said axially-extending slot.

6. The fastener assembly in accordance with claim 1, wherein said first lock member has an outer surface including said plurality of radially extending ratchet teeth, wherein said plurality of radially extending teeth of said second lock member extend toward said base portion and are configured to engage said plurality of radially extending teeth of said first lock member.

7. The fastener assembly in accordance with claim 1, wherein said second lock member is a lock washer, said base portion comprising at least one anti-rotation structure configured to rotationally fix said lock washer with respect to said threaded member.

8. The fastener assembly in accordance with claim 1, wherein said at least one tab comprises a pair of tabs positioned on circumferentially opposite sides of said base portion.

9. A method of assembling a locking mechanism for a fastener including a threaded body portion, said method comprising:
   providing a first lock member including a plurality of radially extending ratchet teeth, the first lock member defining a first aperture extending therethrough, the first aperture sized to receive the threaded body portion;
   forming a base portion of a second lock member, the base portion defining a second aperture extending therethrough, the second aperture sized to receive the threaded body portion;
   forming at least one tab of the second lock member, the at least one tab having a proximal end joined to the base portion and a free end opposite the proximal end, wherein a plurality of radially extending teeth are formed on an inner side of the free end of the at least one tab; and bending the at least one tab at an angle relative to the base portion such that the at least one tab extends axially from the base portion, wherein the second lock member is positionable between a locked configuration in which the plurality of radially extending teeth are configured to engage the plurality of radially extending ratchet teeth and an unlocked configuration in which the plurality of radially extending teeth are spaced from the plurality of radially extending ratchet teeth, wherein the base portion and the at least one tab are a single piece.

10. A locking mechanism for a fastener, said locking mechanism comprising:
   a lock nut having a peripheral surface defining an axially-extending slot;
   a lock member releasably coupled to said lock nut for rotation therewith, said lock member comprising at least one axially-extending tab and a radially-extending detent member on said at least one axially-extending tab, wherein said at least one axially-extending tab at least partially engages said axially-extending slot; and
   a lock washer comprising an axially-extending wall about a periphery of said lock washer, said axially-extending wall defining an inner cavity for receiving said radially-extending detent member of said lock member, the axially-extending wall including an inner surface defining a plurality of radially-extending notches configured to receive said radially-extending detent member.

11. The locking mechanism in accordance with claim 10, wherein said lock member is positionable between a locked configuration in which said radially-extending detent member is in a radially outward position, and an unlocked configuration in which said radially-extending detent member is in a radially inward position.

12. The locking mechanism in accordance with claim 10, wherein said lock member further comprises an annular body coupled to said axially-extending tab, said axially-extending tab comprising a proximal end coupled to said annular body and a free end that includes said radially-extending detent member.

13. The locking mechanism in accordance with claim 12, wherein said lock nut has a first end configured to contact said lock washer and a second end opposite said first end, wherein said lock member is releasably coupled to said lock nut such that said annular body is positioned on said first end and said at least one axially-extending tab extends from said first end to said second end.

14. The locking mechanism in accordance with claim 10, wherein said axially-extending tab comprises a plurality of axially-extending tabs.

15. A fastener assembly comprising:
   a threaded member comprising a threaded body portion;
   a lock nut configured to threadably engage said threaded body portion, said lock nut comprising a body having an outer surface with a plurality of radially extending ratchet teeth; and
   a lock washer comprising a base portion and at least one tab extending axially from said base portion, said base portion comprising an aperture extending therethrough, said base portion comprising at least one anti-rotation structure configured to rotationally fix said lock washer with respect to said threaded member, said at least one tab comprising a free end having a plurality of teeth, wherein said plurality of teeth extend toward said base portion and are configured to engage said plurality of radially extending teeth of said lock nut.

16. The fastener assembly in accordance with claim 15, wherein said at least one tab is positionable between a locked configuration in which said plurality of teeth of said at least one tab are configured to engage said plurality of radially extending ratchet teeth and an unlocked configuration in which said plurality of teeth of said at least one tab are spaced from said plurality of radially extending ratchet teeth.

17. The fastener assembly in accordance with claim 15, wherein said at least one tab comprises a plurality of tabs.

18. The fastener assembly in accordance with claim 15, wherein said at least one tab includes at least one bend.

19. The fastener assembly in accordance with claim 15, wherein said lock washer is a single piece.

* * * * *